United States Patent [19]

Doumaux, Jr. et al.

[11] Patent Number: 5,202,492
[45] Date of Patent: Apr. 13, 1993

[54] AMINES CATALYSIS USING METALLIC PHOSPHATE CONDENSATION CATALYSTS HAVING A CYCLIC STRUCTURE

[75] Inventors: Arthur R. Doumaux, Jr., Charleston; David J. Schreck, Cross Lanes, both of W. Va.

[73] Assignee: Union Carbide Chemicals & Plastics Technology Corporation, Danbury, Conn.

[21] Appl. No.: 390,706

[22] Filed: Aug. 8, 1989

[51] Int. Cl.$^5$ ............................................ C07C 209/00
[52] U.S. Cl. .................................... 564/480; 564/479
[58] Field of Search ................................ 564/480, 479

[56] References Cited

U.S. PATENT DOCUMENTS

| | | | |
|---|---|---|---|
| 2,073,671 | 4/1931 | Andrews | 260/127 |
| 2,467,205 | 4/1949 | Gresham et al. | 260/268 |
| 4,036,881 | 7/1977 | Brennan et al. | 260/583 P |
| 4,044,053 | 8/1977 | Brennan et al. | 260/583 P |
| 4,314,083 | 2/1982 | Ford et al. | 564/479 |
| 4,316,840 | 2/1982 | Ford et al. | 260/239 BC |
| 4,316,841 | 2/1982 | Ford et al. | 260/239 BC |
| 4,324,917 | 4/1982 | McConnell | 564/479 |
| 4,362,886 | 12/1982 | Ford et al. | 564/479 |
| 4,394,524 | 7/1983 | Ford et al. | 564/479 |
| 4,399,308 | 8/1983 | Ford et al. | 564/479 |
| 4,448,997 | 5/1984 | Brennan | 564/479 |
| 4,463,193 | 7/1984 | Johnson et al. | 564/479 |
| 4,503,253 | 3/1985 | Ford et al. | 564/479 |
| 4,521,600 | 6/1985 | Wells et al. | 544/352 |
| 4,524,143 | 6/1985 | Vanderpool | 502/208 |
| 4,540,822 | 9/1985 | Vanderpool | 564/479 |
| 4,547,591 | 10/1985 | Brennan et al. | 564/479 |
| 4,550,209 | 10/1985 | Unvert et al. | 564/479 |
| 4,552,961 | 11/1985 | Herdle | 544/402 |
| 4,555,582 | 11/1985 | Vanderpool | 564/479 |
| 4,560,798 | 12/1985 | Ford et al. | 564/503 |
| 4,578,517 | 3/1986 | Johnson et al. | 564/479 |
| 4,578,518 | 3/1986 | Vanderpool et al. | 564/479 |
| 4,578,519 | 3/1986 | Larken et al. | 564/479 |
| 4,584,405 | 4/1986 | Vanderpool | 564/479 |
| 4,584,406 | 4/1986 | Vanderpool et al. | 564/479 |
| 4,588,842 | 5/1986 | Vanderpool | 564/479 |
| 4,605,770 | 8/1986 | Ford et al. | 564/479 |
| 4,609,761 | 9/1986 | Watts, Jr. et al. | 564/479 |
| 4,612,397 | 9/1986 | Renken | 564/479 |
| 4,617,418 | 10/1986 | Ford et al. | 564/479 |
| 4,683,335 | 7/1987 | Knifton et al. | 564/480 |
| 4,698,427 | 10/1987 | Vanderpool | 544/404 |
| 4,720,588 | 1/1988 | Turcotte et al. | 564/479 |
| 4,806,517 | 2/1989 | Vanderpool et al. | 502/208 |

FOREIGN PATENT DOCUMENTS

| | | |
|---|---|---|
| 0228898 | 7/1987 | European Pat. Off. . |
| 0290960 | 11/1988 | European Pat. Off. . |
| 78945 | 5/1985 | Japan . |
| 236752 | 10/1986 | Japan . |
| 236753 | 10/1986 | Japan . |

Primary Examiner—C. Warren Ivy
Assistant Examiner—Raymond Covington
Attorney, Agent, or Firm—R. M. Allen

[57] ABSTRACT

This invention relates to a process for making amines by condensing an amino compound in the presence of a metallic phosphate condensation catalyst having a cyclic structure or an acyclic structure which is transformed into a cyclic structure during said process. This invention also relates to an alkyleneamines producers composition rich in triethylenetetramine (TETA), tetraethylenepentamine (TEPA) and pentaethylenehexamine (PEHA).

83 Claims, No Drawings

015
AMINES CATALYSIS USING METALLIC PHOSPHATE CONDENSATION CATALYSTS HAVING A CYCLIC STRUCTURE

RELATED APPLICATIONS

U.S. patent application Ser. No. 136,615, filed Dec. 22, 1987, commonly-assigned.

The following are related, commonly assigned applications, filed on an even date herewith: U.S. patent application Ser. No. (390,829), U.S. patent application Ser. No. (390,709); U.S. patent application Ser. No. (390,714); U.S. patent application Ser. No. (390,828); and U.S. patent application Ser. No. (390,708); all incorporated herein by reference.

BRIEF SUMMARY OF THE INVENTION

1. Technical Field

This invention relates to a process for making amines by condensing an amino compound in the presence of a metallic phosphate condensation catalyst having a cyclic structure or an acyclic structure which is transformed into a cyclic structure during said process.

This invention also relates to an alkyleneamines producers composition rich in higher polyalkylene polyamines such as triethylenetetramine (TETA), tetraethylenepentamine (TEPA) and pentaethylenehexamine (PEHA).

2. Background of the Invention

There is a substantial body of literature directed to the use of various acid catalysts to effect intramolecular and intermolecular condensation of amino compounds. U.S. Pat. No. 2,073,671 and U.S. Pat. No. 2,467,205 constitute early prior work on the use of acid condensation catalysts to condense amino compounds. U.S. Pat. No. 2,073,671 discusses, in a general fashion, the catalytic intermolecular condensation of alcohols and amines or ammonia using the same phosphate catalysts later favored by U.S. Pat. No. 2,467,205 for the intramolecular condensation of amines. The two patents are not in harmony over the use of other materials as catalysts. To illustrate this point, U.S. Pat. No. 2,073,671 states:

"Alumina, thoria, blue oxide of tungsten, titania, chromic oxide, blue oxide of molybdenum and zirconia have been mentioned in the literature for use as catalysts in carrying out these reactions but their effectiveness is so low that no practical application has been made of their use."

whereas U.S. Pat. No. 2,467,205 in describing the self condensation of ethylenediamine (EDA) under vapor phase conditions, to initially produce ethyleneamines, but after recycle, eventually enerates piperazine through multistep condensation reactions, followed by deamination, recommends "dehydration catalysts" which are thereafter characterized as "silica gel, titania gel, alumina, thoria, boron phosphate, aluminum phosphate, and the like."

U.S. Pat. No 2,073,671 describes the condensation catalyst in the following terms:

". . . a heated catalyst or contact mass containing phosphorus and especially one or more of the oxygen acids of phosphorus, their anhydrides, their polymers, and their salts; for example, orthophosphoric acid, metaphosphoric acid, pyrophosphoric acid, phosphorous pentoxide, dimetaphosphoric acid, trimetaphosphoric acid, primary ammonium phosphate, secondary ammonium phosphate, normal ammonium phosphate, ammonium metaphosphate, secondary ammonium pyrophosphate, normal ammonium pyrophosphate, aluminum phosphate, aluminum acid phosphate and mixtures of two or more of such materials."

whereas U.S. Pat. No. 2,467,205 describes one of the preferred catalysts as "basic aluminum phosphate".

U.S. Pat. No. 2,454,404 describes the "catalytic deamination of alkylene polyamines" by reacting diethylenetriamine (DETA) vapor over solid catalysts such as activated alumina, bauxite, certain aluminum silicates such as kaolin and oxides of thorium, titanium and zirconium.

U.S. Pat. Nos. 2,073,671 and 2,467,205 demonstrate a common experience in using aluminum phosphate as a condensation catalyst to produce aliphatic amines, and U.S. Pat. Nos. 2,454,404 and 2,467,205 contemplate the other solid catalysts for deamination of amines to make heterocyclic noncyclic amines. In general, the reaction conditions under which deamination to effect cyclization occurs are more severe than those employed for condensation to generate noncyclic molecules, all other factors being comparable.

U.S. Pat. Nos. 4,540,822, 4,584,406 and 4,588,842 depict the use of Group IVB metal oxides as supports for phosphorus catalysts used to effect the condensation of amino compounds with alkanolamines.

U.S. Pat. No. 4,683,335 describes the use of tungstophosphoric acid, molybdophosphoric acid or mixtures deposited on titania as catalysts for the condensation of amines and alkanolamines to make polyalkylenepolyamines.

U.S. Pat. Nos. 4,314,083, 4,316,840, 4,362,886 and 4,394,524 disclose the use of certain metal sulfates as useful catalysts for the condensation of alkanolamine and an amino compound. No distinction is made between the sulfur compounds in respect to catalytic efficacy. Sulfuric acid is as good as any metal sulfate, and all metal sulfates are treated as equivalents. At column 8 of U.S. Pat. No. 4,314,083, it is noted that boron sulfate "gave extremely high selectivity at a low level" of EDA. However, selectivity in general was shown to increase with an increase of EDA relative to MEA in the feed. The only specific metal sulfates disclosed in the patents are antimony sulfate, beryllium sulfate, iron sulfate and aluminum sulfate.

In the typical case of the manufacture of alkyleneamines, mixtures with other alkyleneamines (including a variety of polyalkylenepolyamines and cyclic alkylenepolyamines) are formed. The same holds true when the object of the process is to produce polyalkylenepolyamines whether acyclic or cyclic, in that a variety of amino compounds are also formed. Each of these cyclic and acyclic alkyleneamines can be isolated from the mixture.

The acid catalyzed condensation reaction involving the reaction of an alkanolamine with an amino compound in the presence of an acidic catalyst is believed to proceed through the mechanism of esterifying free surface hydroxyl groups on the acid catalyst with the alkanolamine and/or by protonating the alkanolamine in the presence of the acid catalyst, followed by loss of water and amine condensation of the ester or the hydrated species, as the case may be, to form the alkyleneamine.

Illustrative prior art directed primarily to the cyclic polyalkylenepolyamines (heterocyclic polyamines), but not necessarily limited to the aforementioned acid condensation reaction, are: U.S. Pat. Nos. 2,937,176, 2,977,363, 2,977,364, 2,985,658, 3,056,788, 3,231,573, 3,167,555, 3,242,183, 3,297,701, 3,172,891, 3,369,019, 3,342,820, 3,956,329, 4,017,494, 4,092,316, 4,182,864, 4,405,784 and 4,514,567; European Patent Applications 0 069 322, 0 111 928 and 0 158 319; East German Patent No. 206,896; Japanese Patent Publication No. 51-141895; and French Patent No. 1,381,243. The evolution of the art to the use of the acid catalyzed condensation reaction to generate acyclic alkyleneamines, particularly acyclic polyalkylenepolyamines, as the predominant products stemmed from the initial disclosure in U.S. Pat. No. 4,036,881, though earlier patent literature fairly well characterized such an effect without labeling it so, see U.S. Pat. No. 2,467,205, supra. The acid catalysts are phosphorus compounds and the reaction is carried out in the liquid phase. The trend in this catalyst direction was early set as demonstrated by U.S. Pat. Nos. 2,073,671 and 2,467,205, supra. A modification of this route includes the addition of ammonia to the reaction, see, for example, U.S. Pat. No. 4,394,524 and U.S. Pat. No. 4,463,193 for the purpose of converting alkanolamine such as MEA in situ to alkylene amine such as EDA by reaction with ammonia, and the EDA is in situ reacted with MEA according to the process of U.S. Pat. No. 4,036,881 to form alkyleneamines.

A summary of the prior art employing acid catalysts for making alkyleneamines is set forth in Table 1 below.

TABLE 1

| CITATION | CATALYST TYPE | REACTANTS |
| --- | --- | --- |
| U.S. Pat. No. 2,467,205 | Silica gel, titania gel, alumina, thoria, aluminum phosphate. Preferred catalyst is basic aluminum phosphate. | Vapor phase condensation of EDA over a fixed bed of the catalyst, multipass process shifts from polyethylene-polyamines with the first few cycles. |
| U.S. Pat. No. 4,036,881 | Phosphorus containing substances selected from the group consisting of acidic metal phosphates, phosphoric acid compounds and their anhydrides, phosphorus acid compounds and their anhydrides, alkyl or aryl phosphate esters, alkyl or aryl phosphite esters, alkyl or aryl substituted phosphorus and phosphoric acids wherein said alkyl groups have from 1 to about 8 carbon atoms and said aryl groups have from 6 to about 20 carbon atoms, alkali metal monosalts of phosphoric acid, the thioanalogs of the foregoing, and mixtures of the above. | Alkanolamine and alkyleneamine in liquid phase reaction. |
| U.S. Pat. No. 4,044,053 | Phosphorus containing substances selected from the group consisting of acidic metal phosphates, phosphoric acid compounds and their anhydrides, phosphorus acid compounds and their anhydrides, alkyl or aryl phosphate esters, alkyl or aryl phosphite esters, alkyl or aryl substituted phosphorous acids and phosphoric acids wherein said alkyl groups have from 1 to about 8 carbon atoms and said aryl groups have from 6 to about 20 carbon atoms, alkali metal mono-salts of phosphoric acid and mixtures of the above. | Alkanepolyols and alkyleneamine in liquid phase reaction. |
| U.S. Pat. No. 4,314,083 | Salt of a nitrogen or sulfur containing substance or the corresponding acid. | Alkanolamine and an alkyleneamine in liquid phase reaction. |
| U.S. Pat. No. 4,316,840 | Metal nitrates and sulfates including zirconium sulfate. | Reforming linear polyamines. |
| U.S. Pat. No. 4,316,841 | Phosphate, preferably boron phosphate. | Reforming linear polyamines. |
| U.S. Pat. No. 4,324,917 | Phosphorus-containing cation exchange resin. | Alkanolamine and an alkyleneamine in liquid phase reaction. |
| U.S. Pat. No. 4,362,886 | Arsenic, antimony or bismuth containing compounds. Antimony sulfate specifically disclosed. | Alkanolamie and an alkyleneamine in liquid phase reaction. |
| U.S. Pat. No. 4,399,308 | Lewis acid halide. | Alkanolamine and an alkyleneamine in liquid phase reaction. |
| U.S. Pat. No. 4,394,524 | Phosphorus-containing substance or salt of a sulfur-containing substance, or the corresponding acid. | Ammonia, alkanolamine and an alkyleneamine in liquid phase reaction. |
| U.S. Pat. No. 4,448,997 | Reacts alumina with phosphoric | EDA with MEA |

TABLE 1-continued

| CITATION | CATALYST TYPE | REACTANTS |
|---|---|---|
| | acid, adds ammonium hydroxide. | |
| U.S. Pat. No. 4,463,193 | Group IIIB metal acid phosphate. | Ammonia, alkanolamine and an alkyleneamine. |
| U.S. Pat. No. 4,503,253 | Supported phosphoric acid. | Ammonia, alkanolamine and an alkyleneamine. |
| U.S. Pat. No. 4,521,600 | Select hydrogen phosphates and pyrophosphates. | Alkanolamine and an alkyleneamine. |
| U.S. Pat. No. 4,524,143 | Phosphorus impregnated onto zirconium silicate support. | Alkanolamine and an alkyleneamine. |
| U.S. Pat. No. 4,540,822 | Phosphorus compound deposited on a Group IVB metal oxide support. | Alkanolamine and an alkyleneamine, regenerates the catalyst with $O_2$-containing gas. |
| U.S. Pat. No. 4,547,591 | Silica-alumina alone or in combination with an acidic phosphorus cocatalyst. | An ethyleneamine and an alkanolamine; ethyleneamines; or ammonia and an alkanolamine. |
| U.S. Pat. No. 4,550,209 | An intercalatively catalytically active tetravalent zirconium polymeric reaction product of an organo phosphonic acid or an ester thereof with a compound of tetravalent zirconium reactive therewith. | EDA and MEA. |
| U.S. Pat. No. 4,552,961 | Phosphorus amide compound. | Alkyleneamine and alkanolamine and/or alkylene glycol. |
| U.S. Pat. No. 4,555,582 | Phosphorus chemically bonded to a zirconium silicate support. | MEA and EDA. |
| U.S. Pat. No. 4,560,798 | Rare earth metal or strontium acid phosphate. | MEA. |
| U.S. Pat. No. 4,578,517 | Group IIIB metal acid phosphate. | Ammonia or p-/s-amine alkanolamine. |
| U.S. Pat. No. 4,578,518 | Thermally activated, calcined, pelleted titania containing titanium triphosphate. ". . . the titania that was used was . . . anatase." (Col. 9, lines 18–19). | MEA and EDA. |
| U.S. Pat. No. 4,578,519 | Thermally activated, calcined, pelleted titania with chemically bonded phosphorus derived from polyphosphoric acid. | MEA and EDA with optional recycle of DETA. |
| U.S. Pat. No. 4,584,405 | Activated carbon, optionally treated to incorporate phosphorus. Activated carbon may be washed with strong mineral acid to remove impurities followed by water wash. Optional treatment follows. | MEA and EDA. |
| U.S. Pat. No. 4,584,406 | Pelleted Group IVB metal oxide with chemically bonded phosphorus derived from phosphoryl chloride or bromide. | MEA and EDA. |
| U.S. Pat. No. 4,588,842 | Thermally activated pelleted Group IVB metal oxide with chemically bonded phosphorus. | MEA and EDA. |
| U.S. Pat. No. 4,605,770 | Group IIA or IIIB metal acid phosphate. | Alkanolamine and an alkyleneamine "in liquid phase". |
| U.S. Pat. No. 4,609,761 | Thermally activated pelleted titania with chemically bonded phosphorus. | MEA and EDA. |
| U.S. Pat. No. 4,612,397 | Thermally activated pelleted titania with chemically bonded phosphorus. | MEA and EDA. |
| U.S. Pat. No. 4,617,418 | Acid catalysts, mentions "beryllium sulfate". | Ammonia, alkanolamine and an alkyleneamine "under vapor phase conditions". |
| Japanese Patent Application #1983-185,871, Publication #1985-78,945 | Variety of phosphorus and metal phosphates including Group IVB phosphates. | Ammonia, alkanolamine and ethyleneamine, with ammonia/alkanolamine molar ratio greater than 11. |
| U.S. Pat. No. 4,683,335 | Tungstophosphoric acid, molybdophosphoric acid or mixtures deposited on titania. Examples 2–7 characterize titania surface areas of 51, 60 and 120 $m^2$/gm. | Claims reaction of MEA and EDA, but discloses self-condensation reaction of EDA and DETA. |
| Japanese Patent Application #1985-078,391, Publication | Group IVB metal oxide with bonded phosphorus. | Ammonia and MEA. |

TABLE 1-continued

| CITATION | CATALYST TYPE | REACTANTS |
| --- | --- | --- |
| #1986-236,752 Japanese Patent Application #1985-078,392, Publication #1986-236,753 | Group IVB metal oxide with bonded phosphorus. | Ammonia and MEA. |
| U.S. Pat. No. 4,698,427 | Titania having phosphorus thermally chemically bonded to the surface thereof in the form of phosphate bonds. | Diethanolamine and/or hydroxyethyldiethylene-triamine in EDA. |
| U.S. Pat. No. 4,806,517 | Pelleted Group IVB metal oxide with phosphorus thermally chemically bonded to the surface thereof. | MEA and EDA. |

The market demand for higher polyalkylene polyamines such as TETA, TEPA and PEHA has been progressively increasing in recent years. These higher polyalkyene polyamines are desirable co-products with DETA. It would be desirable to satisfy the existing demand from a cost standpoint by modifying slightly the commercial processes directed to the manufacture of DETA from the reaction of MEA and EDA or other suitable starting raw materials such as DETA and AEEA, to the production of TETA, TEPA and PEHA as major products.

It would be desirable to have continuously produced compositions, generated by the reaction of MEA and EDA or other suitable starting raw materials such as DETA and AEEA over a fixed bed of a condensation catalyst under commercial conditions, that are rich in TETA, TEPA and PEHA, and that are not disproporationately high in PIP and other cyclics.

It would be very beneficial to have a process which increases one's ability to generate the manufacture of desirable higher polyalkylene polyamine products such as TETA, TEPA and PEHA without generating large amounts of cyclic alkylenepolyamine products. In addition, it would also be desirable to have a process with raw material flexibility which provides the potential to control congener distribution, linear to cyclic selectivity and linear to branched selectivity of the higher polyalkylene polyamines products. As used herein, congener distribution refers to polyalkylene polyamines containing the same number of nitrogen atoms but not necessarily having the same molecular weight or structure.

The above features are provided by this invention.

SUMMARY OF THE INVENTION

This invention relates in general to a process of making amines which comprises condensing an amino compound in the presence of a metallic phosphate condensation catalyst having a cyclic structure or an acyclic structure which is transformed into a cyclic structure during said process. The metallic phosphate condensation catalysts used herein contain sufficient residual bound hydroxyl groups or other groupings which renders catalyst formation possible by loss of water or its chemical equivalent such as ammonium hydroxide.

More particularly, this invention relates to a process of making amines by the (i) intramolecular condensation of an amino compound to an amine having a lower molecular weight or (ii) the intermolecular condensation of an amino compound with one or more of another amino compound or a compound containing an alcoholic hydroxyl group using certain metallic phosphates having a cyclic structure or an acyclic structure which is transformed into a cyclic structure during said process as the condensation catalyst. A preferred process involves the manufacture of alkyleneamines, most desirably higher polyalkylene polyamines, by such condensation reactions utilizing sodium dihydrogen phosphate, disodium dihydrogen pyrophosphate or sodium trimetaphosphate as the condensation catalyst.

The invention further relates to a continuously generated alkyleneamines producers composition comprising, based on 100 percent of the weight of the composition and exclusive of any water and/or ammonia present, a) greater than about 3.0 weight percent of the combination of TETA and TEPA, b) greater than about 0.1 weight percent of TEPA, c) greater than about 3.0 weight percent of TETA, d) less than about 90.0 weight percent of DETA and/or EDA, e) less than about 90.0 weight percent of MEA and/or AEEA, f) less than about 12.5 weight percent of the combination of PIP and AEP, g) less than about 15.0 weight percent of other polyalkylene polyamines, h) a TETA+TAEA to PIP+AEP+PEEDA+DAEP+DPE weight ratio of greater than about 0.5, i) a TEPA+AETAEA to PIP+AEP+PEEDA+DAEP+DPE+AEPEEDA+iAEPEEDA AEDAEP+AEDPE+BPEA weight ratio of greater than about 0.5, j) a TETA to TAEA weight ratio of greater than about 2.0, and k) a TEPA to AETAEA weight ratio of greater than about 2.0.

As used herein, the term "amino compound" embraces ammonia and any compound containing nitrogen to which is bonded an active hydrogen. Also, as used herein, the term "oxide" embraces oxides, hydroxides and/or mixtures thereof.

For purposes of this invention, the chemical elements are identified in accordance with the Periodic Table of the Elements, CAS version, Handbook of Chemistry and Physics, 67th Ed., 1986–87, inside cover. Also, for purposes of this invention, Group IIIB metal oxides embraces the lanthanides and actinides.

DETAILED DESCRIPTION

The higher polyalkylene polyamines such as TETA, TEPA and PEHA are very useful commercial products for a variety of applications including fuel oil additives, corrosion inhibitors, fabric softeners, fungicides and others. As indicated above, there is lacking a commercial process for the manufacture of enhanced quantities of TETA, TEPA and PEHA especially as significant products of reaction. There is thus a need for the ability to commercially generate larger production quantities of TETA, TEPA and PEHA and that is the direction of this invention. The process of this invention provides for the reaction of MEA and DETA or other suitable starting raw materials such as EDA and AEEA to produce in a continuous manner a reaction product mixture, termed herein an "alkyleneamines producers composition", in which TETA, TEPA and PEHA are principal products of the reaction.

The process of this invention is distinctive insofar as it achieves the generation of high concentrations of TETA, TEPA and PEHA in a manner which can be suitably employed in a commercial process, particularly a continuous process, for the manufacture of alkyleneamines. In particular, the process of this invention allows the production of TETA, TEPA and PEHA in relatively high yields without generating large amounts of cyclic polyalkylene polyamine products. The process of this invention provides starting raw material flexibility thereby allowing the potential to control congener distribution, linear to cyclic selectivity and linear to branched selectivity of the higher polyalkylene polyamine products.

As indicated above, this invention relates to a process of making amines which comprises condensing an amino compound in the presence of a metallic phosphate condensation catalyst having a cyclic structure or an acyclic structure which is transformed into a cyclic structure during said process.

As also indicated above, this invention relates to a continuously generated alkyleneamines producers composition comprising, based on 100 percent of the weight of the composition and exclusive of any water and/or ammonia present, a) greater than about 3.0 weight percent of the combination of TETA and TEPA, b) greater than about 0.1 weight percent of TEPA, c) greater than about 3.0 weight percent of TETA, d) less than about 90.0 weight percent of DETA and/or EDA, e) less than about 90.0 weight percent of MEA and/or AEEA, f) less than about 12.5 weight percent of the combination of PIP and AEP, g) less than about 15.0 weight percent of other polyalkylene polyamines, h) a TETA+TAEA to PIP+AEP+PEEDA+DAEP+DPE weight ratio of greater than about 0.5, i) a TEPA+AETAEA to PIP+AEP+PEEDA+DAEP+DPE+AEPEEDA+iAEPEEDA+AEDAEP+AEDPE+BPEA weight ratio of greater than about 0.5, j) a TETA to TAEA weight ratio of greater than about 2.0, and k) a TEPA to AETAEA weight ratio of greater than about 2.0.

The alkyleneamines producers composition of this invention can be subjected to conventional separations techniques for recovering the individual components of the composition. Such techniques are well known in the art and include, for example, distillation.

This invention contemplates the catalyzed condensation by (i) intramolecular condensation of an amino compound to an amine having a lower molecular weight, and (ii) intermolecular condensation of an amino compound with one or more of another amino compound or a compound containing an alcohol hydroxyl group to an amine having a lower, same or higher molecular weight than the reactants, in the presence of a metallic phosphate condensation catalyst having a cyclic structure or an acyclic structure which is transformed into a cyclic structure during the process. The metallic phosphate condensation catalysts embraced within the scope of this invention can be cyclic or a mixture of cyclic and acyclic and comprise structural units of the formula:

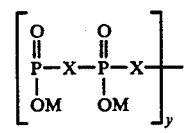

wherein M is the same or different and is a substantially insoluble cation, X is the same or different and is oxygen, nitrogen or sulfur, and y is a value of from 1 to about 20 or greater. The preferred metallic phosphate condensation catalysts have a cyclic structure and ionic character and/or ion exchange capacity.

While not wishing to be bound to any particular theory, it is believed that those metallic phosphates encompassed within the scope of this invention having a cyclic structure and possessing ionic character and/or ion exchange capacity exhibit desired catalytic activity and provide desired product selectivity. While the reaction mixture may initially include one or more metallic phosphates other than metallic phosphates having a cyclic structure and possessing ionic character and/or ion exchange capacity, it is believed to be desirable that such metallic phosphates having a cyclic structure and possessing ionic character and/or ion exchange capacity be formed in situ in order to provide desired catalytic activity and product selectivity. In such instances, catalyst preparation conditions or the reaction conditions should allow for the formation of metallic phosphates having a cyclic structure and possessing ionic character and/or ion exchange capacity. Mixtures of metallic phosphates having a cyclic structure and possessing ionic character and/or ion exchange capacity with metallic phosphates having other than a cyclic structure and other than ionic character and/or ion exchange capacity are believed to exhibit desired catalytic activity and provide desired product selectivity.

In accordance with this invention, the metallic phosphate condensation catalyst has a cyclic structure or an acyclic structure which is capable of being transformed into a cyclic structure during the process. The metallic phosphate condensation catalyst can include, for example, metallic orthophosphates ($PO_4^{-3}$), metallic pyrophosphates ($P_2O_7^{-4}$), metallic polyphosphates (including tripolyphosphates ($P_3O_{10}^{-5}$), tetrapolyphosphates ($P_4O_{13}^{-6}$), pentapolyphosphates ($P_5O_{16}^{-7}$), and higher polyphosphates), metallic metaphosphates (including trimetaphosphates ($P_3O_9^{-3}$), tetrametaphosphates ($P_4O_{12}^{-4}$) and other lower and higher metaphosphates) and metallic ultraphosphates (condensed phosphates containing more $P_2O_5$ than corresponds to the metaphosphate structure). Corresponding metallic metaphosphimates, metallic phosphoramidates and metallic amido- and imidophosphates of the above may also be used as condensation catalysts in accordance with this invention. Suitable metals which can be incorporated into the metallic phosphate condensation catalyst include, for example, Group IA metals, Group IIA metals, Group IIIB metals, Group IVB metals, Group VB metals, Group VIB metals, Group VIIB metals, Group VIII metals, Group IB metals, Group IIB metals, Group IIIA metals, Group IVA metals, Group VA metals, Group VIA metals and mixtures thereof.

Illustrative of metallic orthophosphate catalysts which may be utilized in this invention include, for example, $NaH_2PO_4$, $KH_2PO_4$, $RbH_2PO_4$, $LiH_2PO_4$, $MgHPO_4$, $CaHPO_4$, $YPO_4$, $CePO_4$, $LaPO_4$, $ThPO_4$, $MnPO_4$, $FePO_4$, $BPO_4$, $AlPO_4$, $BiPO_4$, $Mg(H_2PO_4)_2$, $Ba(H_2PO_4)_2$, $Mg(NH_4)_2PO_4$, $Ca(H_2PO_4)_2$, $La(H_2PO_4)_3$ and the like. Illustrative of metallic pyrophosphate catalysts which may be utilized in this invention include, for example, $Na_2H_2P_2O_7$, $K_2H_2P_2O_7$, $Ca_2P_2O_7$, $Mg_2P_2O_7$, $KMnP_2O_7$, $AgMnP_2O_7$, $BaMnP_2O_7$, $NaMnP_2O_7$, $KCrP_2O_7$, $NaCrP_2O_7$, $Na_4P_2O_7$, $K_4P_2O_7$, $Na_3HP_2O_7$, $NaH_3P_2O_7$, $SiP_2O_7$, $ZrP_2O_7$, $Na_6Fe_2(P_2O_7)_3$, $Na_8Fe_4(P_2O_7)_5$, $Na_6Cu(P_2O_7)_2$, $Na_{32}Cu_{14}(NH_4)_2P_2O_7$, $Ca_{32}Cu_{14}Na_4Cu_{18}(P_2O_7)_5$, $Na_2(NH_4)_2P_2O_7$, $Ca(NH_4)_2P_2O_7$, $Mgh_2P_2O_7$, $Mg(NH_4)_2P_2O_7$ and the like. Illustrative of metallic polyphosphate catalysts which may be utilized in this invention include, for example, $NaSr_2P_3O_{10}$, $NaCa_2P_3O_{10}$, $NaNi_2P_3O_{10}$, $Na_5P_3O_{10}$, $K_5P_3O_{10}$, $Na_3MgP_3O_{10}$, $Na_3CuP_3O_{10}$, $Cu_5(P_3O_{10})_2$, $Na_3ZnP_3O_{10}$, $Na_3CdP_3O_{10}$, $Na_6Pb(P_3O_{10})_2$, $Na_3CoP_3O_{10}$, $K_3CoP_3O_{10}$, $Na_3NiP_3O_{10}$, $K_2(NH_4)_3P_3O_{10}$, $Ca(NH_4)_2P_3O_{10}$, $La(NH_4)_2P_3O_{10}$, $NaMgH_2P_3O_{10}$ and the like. Illustrative of metallic metaphosphate catalysts which may be utilized in this invention include, for example, $Na_3P_3O_9$, $K_3P_3O_9$, $Ag_3P_3O_9$, $Na_4P_4O_{12}$, $K_4P_4O_{12}$, $Na_2HP_3O_9$, $Na_4Mg(P_3O_9)_2$, $NaSrP_3O_9$, $NaCaP_3O_9$, $NaBaP_3O_9$, $KBaP_3O_9$, $Ca_3(P_3O_9)_2$, $Ba(P_3O_9)_2$, $Na_2Ni_2(P_3O_9)_2$, $Na_4Ni(P_3O_9)_2$, $Na_4Co(P_3O_9)_2$, $Na_4Cd(P_3O_9)_2$ and the like. Illustrative of metallic ultraphosphate catalysts which may be utilized in this invention include, for example, $CaP_4O_{11}$, $Ca_2P_6O_{17}$, $Na_8P_{10}O_{29}$, $Na_6P_8O_{23}$, $Na_2CaP_6O_{17}$, $Na_2P_4O_{11}$, $NaBaP_7O_{18}$, $Na_2P_8O_{21}$, $K_4P_6O_{17}$ and the like. The metallic phosphate condensation catalysts having an acyclic structure used herein should be capable of being transformed into a cyclic structure under the reaction conditions. The preferred metallic phosphate condensation catalysts for use in this invention include Group IA metal metaphosphates, Group IA meal dihydrogen orthophosphates and Group IA metal dihydrogen pyrophosphates, more preferably $Na_3P_3O_9$, $NaH_2PO_4$ and $Na_2H_2P_2O_7$. Other suitable metallic phosphate condensation catalysts having a cyclic structure or an acyclic structure capable of being transformed into a cyclic structure during the process which are embraced within the scope of this invention are disclosed by Van Wazer, J. R., Phosphorus and Its Compounds, Vol. 1, Interscience Publishers, Inc., New York (1958).

As indicated above, metallic phosphate condensation catalysts having an acyclic structure are suitable for use in the process of this invention provided that the acyclic structure is transformed into a cyclic structure during the reaction. Suitable catalysts for use in the process of this invention include metallic phosphates having a cyclic structure, metallic phosphates having an acyclic structure which are transformed into a cyclic structure during the reaction and mixtures of metallic phosphates having a cyclic structure with metallic phosphates having an acyclic structure which may or may not transform into a cyclic structure during the reaction it is recognized that any combination of metallic phosphates may be used in the process of this invention provided at least one metallic phosphate having a cyclic structure is present during the reaction. It is also recognized that metallic phosphates having a cyclic structure can be formed under reaction conditions from any combination of metallic phosphates having an acyclic structure and/or cyclic structure or other reactants in the process.

The metallic phosphate condensation catalysts can be prepared by conventional methods known in the art. Sodium is believed to be one of a small group of cations effective for stabilizing six-membered cyclic metaphosphates at their temperatures of fusion (about 625° C.) without decomposition to linear and/or other phosphates including mixtures. The formation of cyclic and acyclic metallic phosphate structures appears to depend on the cation ionic size, the coordination number of the cation and the ionic or covalent nature of the metal-oxygen bond.

The level of activity of the metallic phosphate catalyst of the invention is that level which of itself makes the catalyst at least as active in the condensation of amines as, for example, is phosphoric acid on an equivalent basis. Preferably, supported metallic phosphate condensation catalysts should have a surface area greater than about 70 $m^2/gm$ to as high as about 260 $m^2/gm$ or greater depending upon which metal oxide described below that is employed. In the case of titanium oxides, the surface area should be greater than about 140 $m^2/gm$ to as high as about 260 $m^2/gm$, more preferably, greater than about 160 $m^2/gm$ to as high as about 260 $m^2/gm$, determined according to the single point $N_2$ method. In the case of zirconia oxides, the surface area should be greater than about 70 $m^2/gm$ to as high as about 150 $m^2/gm$, more preferably, greater than about 90 $m^2/gm$ to as high as about 135 $m^2/gm$, determined according to the single point $N_2$ method. It is appreciated that the metal oxides described below which can be used in association with the metallic phosphate condensation catalyst and the performance moderators described below can affect the surface area of the metallic phosphate condensation catalyst. While surface areas described above may be preferred, for purposes of this invention, the surface area of the metallic phosphate condensation catalyst should be sufficient to contribute to product selectivity, catalytic activity and/or mechanical or dimensional strength of the catalyst.

The metallic phosphate condensation catalysts useful in this invention can be associated with one or more metal oxides. Preferred metal oxides are amphoteric or slightly acidic or slightly basic. Illustrative of such metal oxides which may be utilized in association with the metallic phosphate condensation catalyst include, for example, one or more of the following: Group IA metal oxides, Group IIA metal oxides, Group IIIB metal oxides (including lanthanides and actinides), Group VB metal oxides, Group VIB metal oxides, Group VIIB metal oxides, Group VIII metal oxides, Group IB metal oxides, Group IIB metal oxides, Group IIIA metal oxides, Group IVA metal oxides, Group VA metal oxides, Group VIA metal oxides and Group IVB metal oxides or mixtures thereof. Preferred metal oxides which may be utilized in association with the metallic phosphate condensation catalyst include, for example, one or more oxides of beryllium, scandium, yttrium, terbium, dysprosium, holmium, erbium, thulium, ytterbium, lutetium, titanium, zirconium, hafnium, vanadium, niobium, tantalum, tungsten, iron, cobalt, zinc, silver, aluminum, gallium, indium, silicon, germanium, tin, lead, arsenic, antimony and bismuth.

Group IVA and IVB metal oxides such as silica, titanium dioxide and zirconium dioxide are preferred for use in this invention. For mixed metal oxides in which at least one of the metals is titanium, suitable metals in association with titanium may include, for example, one or more of the following: Group IIIB metals such as scandium, yttrium and lanthanum including the lanthanides, Group VB metals such as niobium and tantalum, Group VIB metals such as chromium, molybdenum and tungsten, Group VIII metals such as iron, cobalt and nickel, Group IIB metals such as zinc and cadmium, Group IIIA metals such as boron, aluminum, gallium and indium, Group IVA metals such as silicon, germanium, tin and lead, Group VA metals such as arsenic, antimony and bismuth, and Group IVB metals such as zirconium and hafnium. For mixed metal oxides in which at least one of the metals is zirconium, suitable metals in association with zirconium may include, for example, one or more of the following: Group IVA metals such as silicon, germanium, tin and lead, Group VB metals such as niobium and tantalum, and Group VIB metals such as chromium, molybdenum and tungsten. The virtue of these metal oxides is that they demonstrate higher mechanical strength than the metallic phosphate component per se and can contribute to product selectivity and catalytic activity.

Illustrative of mixed metal oxides which may be used in association with the metallic phosphate catalyst include, for example, $TiO_2$—$SiO_2$, $TiO_2$—$Al_2O_3$, $TiO_2$—$CdO$, $TiO_2$—$Bi_2O_3$, $TiO_2$—$Sb_2O_5$, $TiO_2$—$SnO_2$, $TiO_2$—$ZrO_2$, $TiO_2$—$BeO$, $TiO_2$—$MgO$, $TiO_2$—$CaO$, $TiO_2$—$SrO$, $TiO_2$—$ZnO$, $TiO_2$—$Ga_2O_3$, $TiO_2$—$Y_2O_3$, $TiO_2La_2O_3$, $TiO_2$—$MoO_3$, $TiO_2$—$Mn_2O_3$, $TiO_2$—$Fe_2O_3$, $TiO_2$—$Co_3O_4$, $TiO_2$—$WO_3$, $TiO_2$—$V_2O_5$, $TiO_2$—$Cr_2O_3$, $TiO_2$—$ThO_2$, $TiO_2$—$Na_2O$, $TiO_2$—$BaO$, $TiO_2$—$CaO$, $TiO_2$—$HfO_2$, $TiO_2$—$Li_2O$, $TiO_2$—$Nb_2O_5$, $TiO_2$—$Ta_2O_5$, $TiO_2$—$Gd_2O_3$, $TiO_2$—$Lu_2O_3$, $TiO_2$—$Yb_2O_3$, $TiO_2$—$CeO_2$, $TiO_2$—$Sc_2O_3$, $TiO_2$—$PbO$, $TiO_2$—$NiO$, $TiO_2$—$CuO$, $TiO_2$—$CoO$, $TiO_2$—$B_2O_3$, $ZrO_2$—$SiO_2$, $ZrO_2$—$Al_2O_3$, $ZrO_2$—$SnO$, $ZrO_2$—$PbO$, $ZrO_2$—$Nb_2O_5$, $ZrO_2$—$Ta_2O_5$, $ZrO_2$—$Cr_2O_3$, $ZrO_2$—$MoO_3$, $ZrO_2$—$WO_3$, $ZrO_2$-$TiO_2$, $ZrO_2$—$HfO_2$, $TiO_2$—$SiO_2$—$Al_2O_3$, $TiO_2$—$SiO_2$—$ZnO$, $TiO_2$—$SiO_2$—$ZrO_2$, $TiO_2$—$SiO_2$—$CuO$, $TiO_2$—$SiO_2$—$MgO$, $TiO_2$—$SiO_2$—$Fe_2O_3$, $TiO_2$—$SiO_2$—$B_2O_3$, $TiO_2$—$SiO_2$—$WO_3$, $TiO_2$—$SiO_2$—$Na_2O$, $TiO_2$—$SiO_2$—$MgO$, $TiO_2$—$SiO_2$—$La_2O_3$, $TiO_2$—$SiO_2$—$Nb_2O_5$, $TiO_2$—$SiO_2$—$Mn_2O_3$, $TiO_2$—$SiO_2$—$Co_3O_4$, $TiO_2$—$SiO_2$—$NiO$, $TiO_2SiO_2$—$PbO$, $TiO_2$—$SiO_2$—$Bi_2O_3$, $TiO_2$—$Al_2O_3$—$ZnO$, $TiO_2$—$Al_2O_3$—$ZrO_2$, $TiO_2$—$Al_2O_3$—$Fe_2O_3$, $TiO_2$—$Al_2O_3$—$WO_3$, $TiO_2$—$Al_2O_3$—$La_2O_3$, $TiO_2$—$Al_2O_3$—$Co_3O_4$, $ZrO_2$—$SiO_2$—$Al_2O_3$, $ZrO_2$—$SiO_2$—$SnO$, $ZrO_2$—$SiO_2$—$Nb_2O_5$, $ZrO_2$—$SiO_2$—$WO_3$, $ZrO_2$—$SiO_2$—$TiO_2$, $ZrO_2$—$SiO_2$—$MoO_3$, $ZrO_2$—$SiO_2$—$HfO_2$, $ZrO_2$—$SiO_2$—$Ta_2O_5$, $ZrO_2$—$Al_2O_3$—$SiO_2$, $ZrO_2$—$Al_2O_3$—$PbO$, $ZrO_2$—$Al_2O_3$—$NbO_2O_5$, $ZrO_2$—$Al_2O_3$—$WO_3$, $ZrO_2$—$Al_2O_3$—$TiO_2$, $ZrO_2$—$Al_2O_3$—$MoO_3$, $ZrO_2$—$HfO_2$—$Al_2O_3$, $ZrO_2$—$HfO_2$—$TiO_2$, and the like. Other suitable mixed metal oxide catalysts embraced within the scope of this invention are disclosed by Tanabe et al., Bulletin of the Chemical Society of Japan, Vol. 47(5), pp. 1064–1066 (1974).

The metal oxides described herein which can be used in association with the metallic phosphate catalyst may contribute to product selectivity and/or catalytic activity of the reaction and/or stability of the catalyst. The catalyst structure can comprise from about 0 to about 90 percent or greater by weight of the metal oxide, preferably from about 0 to about 75 percent by weight of the metal oxide, and more preferably from about 0 to about 50 percent by weight of the metal oxide, the remainder being the weight of the metallic phosphate catalyst. For mixed metal oxides containing titania, higher concentrations of titania can provide very desirable product selectivities including acyclic to cyclic selectivities and linear to branched selectivities of higher polyalkylene polyamine products. As discussed hereinafter, the metallic phosphate condensation catalyst of this invention may also contain support(s), binding agent(s) or other additives to stabilize or otherwise help in the manufacture of the catalyst.

Though the metallic phosphate condensation catalyst of the invention provides sufficient activity to effect the condensation reaction, certain combinations of reactants and/or product formation may be benefited by treating the catalyst with a catalyst moderator, hereinafter termed "performance moderator." Catalyst moderators are widely used to control the performance of catalysts in areas of selectivity to certain products and the repression of a catalyst's proclivity to generate a broad range of reaction products. A range of suitable materials may impact the metallic phosphate condensation catalysts of this invention in the variety of reaction products. The performance moderator may be any material which impacts the metallic phosphate condensation catalyst's selection of reaction products or which changes the proportion of any one or more of the reaction products which the metallic phosphate condensation catalyst generates at comparable processing conditions. In addition to contributing to product selectivity, the performance moderator may be any material which contributes to catalytic activity and/or catalyst stability (mechanical or dimensional strength).

An illustrative performance moderator is a mineral acid or a compound derived from a mineral acid. Suitable for use as performance moderators are one or more phosphoric acid or a salt of phosphoric acid, hydrogen fluoride, hydrofluoric acid or a fluoride salt, sulfuric acid or a salt of sulfuric acid, and the like. The moderator may also be organic esters of phosphoric acid or a salt of phosphoric acid, hydrogen fluoride organic complexes, hydrofluoric acid organic complexes or a fluoride salt organic complexes, organic esters of sulfuric acid or a salt of sulfuric acid, and the like. Suitable salts of phosphoric acid include sodium dihydrogen phosphate, disodium hydrogen phosphate, sodium phosphate and the like. Other illustrative performance moderators include the metal oxides described above which can be used in association with the metallic phosphate condensation catalyst and also metallic phosphates which may or may not have a cyclic structure. Certain of these metallic phosphate performance moderators may also be effective as catalysts for use in this invention.

The metal oxides described hereinabove which can be used in association with the metallic phosphate catalyst can also be used as performance moderators in accordance with this invention. The metal oxides can contribute to product selectivity, catalytic activity and/or catalyst stability (mechanical strength).

As indicated above, other performance moderators which can be used in accordance with this invention include metallic phosphates which may or may not have a cyclic structure. Corresponding metallic metaphosphimates, metallic phosphoramidates and metallic amido- and imidophosphates of the above may also be used as performance moderators in accordance with this invention. Such metallic phosphates can contribute to product selectivity, catalytic activity and/or catalyst stability (mechanical strength).

Other performance moderators which can be used in accordance with this invention include metallic polyphosphates which may or may not have a condensed structure. Suitable metallic polyphosphates having a condensed structure are disclosed in U.S. patent application Ser. No. (390,709), filed on an even date herewith and incorporated herein by reference. Corresponding metallic metaphosphimates, metallic phosphoramidates and metallic amido- and imidophosphates of the above may also be used as performance moderators in accordance with this invention. Illustrative metallic polyphosphates having a condensed structure include many of the metallic phosphates described above.

Group VIB metal-containing substances may be used as performance moderators in accordance with this invention. Suitable Group VIB metal-containing substances are disclosed in U.S. patent application Ser. No. (390,708), filed on an even date herewith and incorporated herein by reference. Illustrative of Group VIB metal-containing performance moderators include, for example, one or more oxides of tungsten, chromium, molybdenum or mixtures thereof.

A variety of conventional phosphorus-containing substances may be suitable for use as performance moderators in this invention. The conventional substances should be capable of functioning as a performance moderator. Illustrative of conventional phosphorus containing substances may include, for example, those disclosed in U.S. Pat. No 4,036,881, U.S. Pat. No. 4,806,517, U.S. Pat. No. 4,617,418, U.S. Pat. No. 4,720,588, U.S. Pat. No. 4,394,524, U.S. Pat. No. 4,540,822, U.S. Pat. No. 4,588,842, U.S. Pat. No. 4,605,770, U.S. Pat. No. 4,683,335, U.S. Pat. No. 4,316,841, U.S. Pat. No. 4,463,193, U.S. Pat. No. 4,503,253, U.S. Pat. No. 4,560,798 and U.S. Pat. No. 4,578,517.

Suitable conventional phosphorus-containing substances which may be employed as performance moderators in this invention include acidic metal phosphates, phosphoric acid compounds and their anhydrides, phosphorous acid compounds and their anhydrides, alkyl or aryl phosphate esters, alkyl or aryl phosphite esters, alkyl or aryl substituted phosphorous acids and phosphoric acids, alkali metal monosalts of phosphoric acid, the thioanalogs of the foregoing, and mixtures of any of the above.

The amount of the performance moderator of the mineral acid type used with the metallic phosphate catalyst of the invention is not narrowly critical. Generally, the amount does not exceed 25 weight percent of the weight of the catalyst. As a rule, it is desirable to use at least 0.01 weight percent of the weight of the catalyst. Preferably, the amount of performance moderator, when used, will range from about 0.2 to about 10 weight percent of the weight of the catalyst. Most preferably, the amount of performance moderator, when used, will range from about 0.5 to about 5 weight percent of the weight of the catalyst.

The amount of performance moderator other than the mineral acid type used with the metallic phosphate catalyst is not narrowly critical. Generally, the amount does not exceed 90 weight percent of the weight of the catalyst. The amount of performance moderator can range from about 0 to about 90 or greater weight percent of the weight of the catalyst, preferably from about 0 to about 75 weight percent of the weight of the catalyst, and more preferably from about 0 to about 50 weight percent of the weight of the catalyst. Most preferably, the amount of performance moderator, when used, will range from about 0.5 to about 25 weight percent of the weight of the catalyst.

This invention also embraces the use of vicinal di(hetero)alkylene organometalates in the preparation of amines. Suitable vicinal di(hetero)alkylene organometalates are disclosed in U.S. patent application Ser. No. 390,828, filed on an even date herewith and incorporated herein by reference.

The performance moderator can be provided to the metallic phosphate catalyst by conventional procedures known in the art. For example, the performance moderator can be provided to the catalyst by impregnating particles or monolithic structures comprising the metallic phosphate catalyst with liquid comprising the performance moderator. This is a well known procedure in the art for incorporating additives to a solid support material. The metallic phosphate catalyst of the invention may be utilized as solid powders or as fused, bonded or compressed solid pellets, or larger structures in association with the one or more metal oxides, or as coated, fused, bonded or compressed solid pellets, or larger structures, composited with one or more support materials, in association with one or more metal oxides. These solid structures may be treated with the performance moderator by mixing a liquid body of the performance moderator with the solid structure. For example, the metallic phosphate catalyst solids may be slurried in the performance moderator, drained, washed and suctioned to remove excess performance moderator, and then dried with heat to remove any volatiles accompanying the performance moderator. The drying temperature chosen will depend on the nature of the volatiles to be removed. Usually, the time/temperature for effecting drying will be below the conditions for effecting dehydration to remove bound water from the metal oxide in association with the metallic phosphate catalyst. Normally the drying temperature will be greater than about 120° C. and below about 600° C. depending on the thermal stability of the catalyst. The drying time will generally go down as the drying temperature rises and vice versus, and may extend from 5 seconds to about 24 hours.

Alternatively, the performance moderator can be provided to the catalyst at the time of preparing the metallic phosphate catalyst in association with one or more metal oxides. For example, one or more metal oxides may be condensed from their respective hydrolyzable monomers to the desired oxides to form oxide powders which can thereafter be blended and compressed with the metallic phosphate to form pellets and larger structures of the metal oxide-containing condensation catalyst of this invention. The one or more metal oxides which can be used in association with the metallic phosphate catalyst in accordance with this invention can be provided from metal salts which can be heated to form the metal oxide. It is appreciated that the performance moderator can be incorporated into the molecular bonding configuration of the metal oxide-containing condensation catalyst by conventional procedures known in the art.

The metallic phosphate condensation catalysts in association with one or more metal oxides prior to the optional treatment of the performance moderator may be prepared in a wide variety of ways. For example, one or more metal oxides may be provided as a partial condensate on a support, such as a silica or alpha, beta or gamma alumina, silicon carbide, and the like, and then condensed by heating to effect polymerization to the desired oxide form. The metal oxide(s) may be condensed from hydrolyzable monomers to the desired oxide, indeed, to form an oxide powder which can thereafter be compressed in the presence of a metallic phosphate to form pellets and larger structures of the metal oxide-containing condensation catalyst of the invention. A blend of the powder and metallic phosphate can be made into a shapeable paste which can be extruded and cut into pellets according to conventional procedures. The extrudate may thereafter be fired to cure the metallic phosphate and fix the structure. The cut extrudate may be blended with a support material such as those characterized above, and the blend fired to fuse the metal oxide-containing catalyst to the support.

In a preferred embodiment of this invention, a high surface area silica or titania can be slurried with an aqueous solution of sodium dihydrogen phosphate, disodium dihydrogen pyrophosphate or sodium trimetaphosphate, extruded, and calcined at a temperature of about 400° C.

A preferred catalyst structure comprises sodium dihydrogen phosphate, disodium dihydrogen pyrophosphate or sodium trimetaphosphate in association with a Group IVA or IVB metal oxide having a surface area of at least a 140 m²/gm which may or may not be bonded to a support material. The term "support," as used herein and in the claims, means a solid structure which does not adversely affect the catalytic properties of the catalyst and is at least as stable as the catalyst to the reaction medium. The support can function as an amine condensation catalyst independent of the metallic phosphate having a cyclic structure, although it may have lower catalytic activity to the reaction. The support may act in concert with the catalyst to moderate the reaction. Some supports may contribute to the selectivity of the reaction. The catalyst structure can comprise from about 2 to about 60 percent by weight or greater of the support, more preferably from about 10 to about 50 percent by weight of the support, the remainder being the weight of the metal oxide(s) and metallic phosphate. Included in the weight of the support is the weight of any binding agent such as phosphates, sulfates, silicates, fluorides, and the like, and any other additive provided to stabilize or otherwise help in the manufacture of the catalyst. The support may be particles as large or larger than the catalyst component and "glued" to the catalytic metallic phosphate and/or metal oxide by virtue of a binding medium.

The support may constitute a separate phase in the process of extruding the catalytic structure. In this embodiment, the support forming material, preferably as a paste is blended with a paste of the metallic phosphate and one or more metal oxides or a partial condensate thereof. The paste may comprise the oxide forms of the support and the metallic phosphate, each blended with water, and/or binding agents. The extrudate of the blend is passed through a multiorificed die and chopped into pellets of the desired sizes. The particles may be doughnut shaped, spherical, and the like. Then the particles are calcined to dry them and complete any condensation reaction in the support and/or the metal oxide-containing condensation catalyst.

The use of supports for the metallic phosphate condensation catalyst provides a number of significant advantages. It has been determined that some of the metallic phosphates are not as stable in the amines reaction media when utilized over an extended period of time. When the reaction is effected as a batch reaction, this matter is not a problem. However, when the reaction is effected with the metallic phosphate catalyst as part of a fixed bed in a tubular reactor, the preferred procedure for carrying out the invention, it is desirable to have the catalyst be more stable. When the catalyst is combined with the support, the catalyst has greater stability for the reaction medium, and therefore, it is better able to be used in a fixed bed of a continuous reactor. The supported catalysts suffer from none of the leaching problems that the catalyst per se may have or the problems that are associated with the prior art catalysts, such as acidic phosphorus compounds on silica.

The reactants used in the condensation process of the invention may be ammonia or organic compound containing —NH— and any compound possessing an alcoholic hydroxyl group, subject to the following: the intramolecular condensation of an amino compound produces an amine having a lower molecular weight, and the intermolecular condensation of an amino compound with one or more of another amino compound or a compound containing an alcoholic hydroxyl group produces an amine having a lower, same or higher molecular weight than the reactants.

Illustrative of suitable reactants in effecting the process of the invention, include by way of example:

Ammonia
MEA—monoethanolamine
EDA—ethylenediamine
MeEDA—methylethylenediamine
EtEDA—ethylethylenediamine
AEEA—N-(2-aminoethyl)ethanolamine
HEP—N-(2-hydroxyethyl)piperazine
DETA—diethylenetriamine
AEP—N-(2-aminoethyl)piperazine
TAEA—trisaminoethylamine
TETA—triethylenetetramine
TEPA—tetraethylenepentamine
PEHA—pentaethylenehexamine TETA Isomers TAEA—trisaminoethylamine
TETA—triethylenetetramine
DPE—dipiperazinoethane
DAEP—diaminoethylpiperazine
PEEDA—piperazinoethylethylenediamine TEPA Isomers AETAEA—aminoethyltrisaminoethylamine
TEPA—tetraethylenepentamine
AEDPE—aminoethyldipiperazinoethane
AEPEEDA—aminoethylpiperazinoethylethylenediamine
iAEPEEDA—isoaminoethylpiperazinoethylethylenediamine
AEDAEP—aminoethyldiaminoethylpiperazine
BPEA—bispiperazinoethylamine The foregoing also can represent the products of the reaction. For example, ammonia and MEA are frequently employed to produce EDA along with a variety of other amines, most of which are set forth above.

Glycol compounds can also be employed in the preparation of amines in accordance with this invention. For purposes of this invention, glycol compounds embrace diols and polyols. Illustrative of suitable glycol compounds include alkylene glycols such as ethylene glycol, propylene glycol, 1,3-propane diol or mixtures thereof.

The process may be effected in the liquid or vapor or supercritical liquid states or mixtures thereof though the actual reaction is believed to occur on the catalyst s solid surface in the absorbed state. In this context, the vapor phase reaction is intended to refer to the general vapor state of the reactants. Though the reaction conditions may range from subatmospheric to superatmospheric conditions, it is desirable to run the reaction from about 50 psig to about 3,000 psig, preferably from about 200 psig to about 2,000 psig.

The temperature of the reaction may be as low as about 125° C. to about 400° C. Preferably, the reaction temperature ranges from about 150° C. to about 350° C., and most preferably from about 225° C. to about 325° C.

The reaction may be effected by the incremental addition of one of the reactants to the other or by the joint addition of the reactants to the catalyst. The preferred process effects the reaction in a continuous manner over a fixed bed of the metallic phosphate catalyst in a tubular reactor. However, the reaction may be carried out by slurrying the catalyst in the reactants or in a batch mode in an autoclave. An inert such as nitrogen, methane and the like can be used in the reaction process The preferred process involves the formation of alkyleneamines from the intermolecular condensation of alkanolamines and alkyleneamines or the intramolecular condensation of alkyleneamines or alkanolamines. Illustrative of such reactions are the following reactant combinations:

| REACTANT | REACTANT | PRODUCTS |
| --- | --- | --- |
| Ammonia | Methanol | Monomethylamine Dimethylamine Trimethylamine |
| Ammonia | MEA | EDA, DETA, AEEA, TETA, TEPA, PIP |
| Ammonia | AEEA | DETA, PIP |
| MEA, Ammonia | EDA | EDA, AEEA, HEP, DETA, AEP, TETA, TEPA, PEHA, TETA Isomers: TAEA, TETA, DAEP, PEEDA, DPE TEPA, TEPA Isomers: AETAEA, AEPEEDA, AEDAEP, AEDPE, BPEA |
| MEA | EDA | AEEA, HEP, DETA, AEP, TETA, TEPA, PEHA, TETA Isomers: TAEA, TETA, DAEP, PEEDA, DPE TEPA, TEPA Isomers: AETAEA, AEPEEDA, AEDAEP, AEDPE, BPEA |
| EDA | AEEA | HEP, AEP, TETA, TEPA, PEHA, TETA Isomers: TAEA, TETA, DAEP, PEEDA, DPE TEPA, TEPA Isomers: AETAEA, AEPEEDA, AEDAEP, AEDPE, BPEA |
| DETA | AEEA | TEPA Isomers, AEP |
| EDA | EDA | DETA, TETA AND TEPA Isomers |

The process of the invention provides the ability to generate the manufacture of desirable higher polyalkylene polyamine products such as TETA, TEPA and PEHA without generating large amounts of cyclic alkylenepolyamine products such as PIP, AEP and HEP. The alkyleneamines producers composition of this invention has a TETA+TAEA to PIP+AEP+PEEDA+DAEP+DPE weight ratio of greater than about 0.5, a TETA to TAEA weight ratio of greater than about 2.0 and a TEPA to AETAEA weight ratio of greater than about 2.0.

The process of this invention provides the potential to control congener distribution, linear to cyclic selectivity and linear to branched selectivity of the higher polyalkylene polyamines.

It is appreciated that the metallic phosphate condensation catalysts of this invention may also be useful in the production of alkylamines. For example, an alcohol and at least one of ammonia, a primary amine, a secondary amine or a tertiary amine may be contacted in the presence of a metallic phosphate condensation catalyst having a cyclic structure or an acyclic structure which is transformed into a cyclic structure during the process under conditions effective to produce alkylamines.

This invention is further illustrated by certain of the following examples:

EXAMPLES

In the examples set forth in the tables below, the catalyst of choice was placed in one of three tubular reactors, each having an outside diameter of 1 inch and an overall length of 24 inches. The catalyst portion of the reactor was sufficient for accommodating 100 cubic centimeters of catalyst. The reactor was made of 316 stainless steel. As used herein, AB1 refers to a material obtained from Norton Company, Akron, Ohio, which is a mixture of sodium trimetaphosphate and sodium tripolyphosphate. As used in the tables below, acyclic (N4)/cyclic (<=N4) refers to the weight ratio of TETA+TAEA to PIP+AEP+PEEDA+DAEP+DPE. The catalysts employed are identified as follows:

| Designation | Composition | Physical Properties |
| --- | --- | --- |
| A | Titanium dioxide (anatase)/sodium trimetaphosphate; Ti:P atom ratio = 5.7:1 | Particle size: 1/16 inch cylindrical extrudates; Catalyst surface area: 133.3 m$^2$/gm; Pore volume N$_2$: 0.344 cc/gm; Pore area: 83.5 m$^2$/gm; Bulk density: 1.55 gm/cc. |
| B | Titanium dioxide (anatase)/sodium tripolyphosphate; Ti:P atom ratio = 5.7:1 | Particle size: 1/16 inch cylindrical extrudates; Catalyst surface area: 80.3 m$^2$/gm; Pore volume N$_2$: 0.236 cc/gm; Pore area: 54.2 m$^2$/gm; Bulk density: 1.72 gm/cc. |
| C | Titanium dioxide | Particle size: 1/16 |

| Designation | Composition | Physical Properties |
|---|---|---|
|  | (anatase)/AB1; Ti:P atom ratio = 5.7:1 | inch cylindrical extrudates; Catalyst surface area: 115.0 m²/gm; Pore volume N₂: 0.429 cc/gm; Pore area: 87.4 m²/gm; Bulk density: 1.39 gm/cc. |
| D | Titanium dioxide (anatase)/sodium pyrophosphate; Ti:P atom ratio = 5.7:1 | Particle size: 1/16 inch cylindrical extrudates; Catalyst surface area: 78.6 m²/gm; Pore volume N₂: 0.339 cc/gm; Pore area: 72.1 m²/gm; Bulk density: 1.59 gm/cc. |
| E | Titanium dioxide (anatase)/AB1/ boric acid (2 wt. %) | Particle size: 1/16 inch cylindrical extrudates; Catalyst surface area: 97.1 m²/gm; Pore volume N₂: 0.440 cc/gm; Pore area: 84.2 m²/gm; Bulk density: 1.32 gm/cc. |
| F | Titanium dioxide (anatase)/AB1/ ammonium tetra-fluoroborate (2 wt. %) | Particle size: 1/16 inch cylindrical extrudates; Catalyst surface area: 39.6 m²/gm; Pore volume N₂: 0.442 cc/gm; Pore area: 66.7 m²/gm; Bulk density: 1.34 gm/cc. |
| G | Titanium dioxide (anatase)/AB1/ sodium tetra-fluoroborate (8 wt. %) | Particle size: 1/16 inch cylindrical extrudates; Catalyst surface area: 44.1 m²/gm; Pore volume N₂: 0.432 cc/gm; Pore area: 69.1 m²/gm; Bulk density: 1.35 gm/cc. |
| H | Titanium dioxide (anatase)/AB1/ sodium tetra-fluoroborate (8 wt. %) | Particle size: 1/16 inch cylindrical extrudates; Catalyst surface area: 23.0 m²/gm; Pore volume N₂: 0.373 cc/gm; Pore area: 36.6 m²/gm; Bulk density: 1.57 gm/cc. |
| I | Titanium dioxide (anatase)/AB1/ sodium meta-tungstate (1 wt. %) | Particle size: 1/16 inch cylindrical extrudates; Catalyst surface area: 91.3 m²/gm; Pore volume N₂: 0.414 cc/gm; Pore area: 75.7 m²/gm; Bulk density: 1.40 gm/cc |
| J | Titanium dioxide (anatase)/AB1/ sodium meta-tungstate (2 wt. %) | Particle size: 1/16 inch cylindrical extrudates; Catalyst surface area: 101.2 m²/gm; Pore volume N₂: 0.442 cc/gm; Pore area: 94.2 m²/gm; Bulk density: 1.38 gm/cc. |
| K | Titanium dioxide (anatase)/AB1/ sodium meta-tungstate (4 wt. %) | Particle size: 1/16 inch cylindrical extrudates; Catalyst surface area: 100.2 m²/gm; Pore volume N₂: 0.429 cc/gm; Pore area: 90.0 m²/gm; Bulk density: 1.43 gm/cc. |
| L | Titanium dioxide (anatase)/AB1/ ammonium meta-tungstate (2 wt. % as WO₃) | Particle size: 1/16 inch cylindrical extrudates; Catalyst surface area: 97.9 m²/gm; Pore volume N₂: 0.431 cc/gm; Pore area: 79.4 m²/gm; Bulk density: 1.43 gm/cc. |
| M | Titanium dioxide (anatase)/AB1/ ammonium meta-tungstate (4 wt. % as WO₃) | Particle size: 1/16 inch cylindrical extrudates; Catalyst surface area: 91.8 m²/gm; Pore volume N₂: 0.402 cc/gm; Pore area: 69.2 m²/gm; Bulk density: 1.51 gm/cc. |
| N | Titanium dioxide (anatase)/AB1/ ammonium meta-tungstate (8 wt. % as WO₃) | Particle size: 1/16 inch cylindrical extrudates; Catalyst surface area: 78.1 m²/gm; Pore volume N₂: 0.403 cc/gm; Pore area: 74.0 m²/gm; Bulk density: 1.47 gm/cc. |
| O | Titanium dioxide (anatase)/AB1/ lanthanum oxide (2 wt. %) | Particle size: 1/16 inch cylindrical extrudates; Catalyst surface area: 102.8 m²/gm; Pore volume N₂: 0.409 cc/gm; Pore area: 65.3 m²/gm; Bulk density: 1.49 gm/cc. |
| P | Titanium dioxide (anatase)/AB1/ lanthanum oxide (4 wt. %) | Particle size: 1/16 inch cylindrical extrudates; Catalyst surface area: 102.6 m²/gm; Pore volume N₂: 0.418 cc/gm; Pore area: 85.4 m²/gm; Bulk density: 1.41 gm/cc. |
| Q | Titanium dioxide (anatase)/AB1/ niobium oxide (2 wt. %) | Particle size: 1/16 inch cylindrical extrudates; Catalyst surface area: 102.8 m²/gm; Pore volume N₂: 0.435 cc/gm; Pore area: 85.5 m²/gm; Bulk density: 1.35 gm/cc. |
| R | Titanium dioxide (anatase)/AB1/ sodium bicarbonate (2 wt. %) | Particle size: 1/16 inch cylindrical extrudates; Catalyst surface area: 99.5 m²/gm; Pore volume N₂: 0.417 cc/gm; Pore area: 76.4 m²/gm; Bulk density: 1.41 gm/cc. |
| S | Titanium dioxide (anatase)/AB1/ vanadium oxide (2 wt. %) | Particle size: 1/16 inch cylindrical extrudates; Catalyst surface area: 88.7 m²/gm; Pore volume N₂: 0.411 cc/gm; Pore area: 63.9 m²/gm; Bulk density: 1.44 gm/cc. |
| T | Titanium dioxide (anatase)/SiO₂/ Al₂O₃/sodium trimetaphosphate (10 wt. %) | Particle size: 1/16 inch cylindrical extrudates; Catalyst surface area: 129.9 m²/gm; Pore volume N₂: 0.321 cc/gm; Pore area: 163 m²/gm; Bulk density: 1.59 gm/cc. |
| U | Titanium dioxide | Particle size: 1/16 |

| Designation | Composition | Physical Properties |
|---|---|---|
| | (anatase)/SiO$_2$/ B$_2$O$_3$/sodium trimetaphosphate (10 wt %) | inch cylindrical extrudates; Catalyst surface area: 159.5 m$^2$/gm; Pore volume N$_2$: 0.312 cc/gm; Pore area: 129.8 m$^2$/gm, Bulk density: 1.54 gm/cc. |
| V | Titanium dioxide (anatase)/SiO$_2$/ sodium trimeta-phosphate (10 wt %) | Particle size: 1/16 inch cylindrical extrudates; Catalyst surface area: 136.5 m$^2$/gm; Pore volume N$_2$: 0.399 cc/gm; Pore area: 162.5 m$^2$/gm; Bulk density: 1.48 gm/cc. |
| W | Titanium dioxide/ AB1 | Particle size: 1/16 inch cylindrical extrudates; Catalyst surface area: 4.40 m$^2$/gm; Pore volume N$_2$: 0.184 cc/gm; Pore area: 19.2 m$^2$/gm; Bulk density: 2.10 gm/cc. |
| X | Titanium dioxide (anatase)/AB1 | Particle size: 1/16 inch cylindrical extrudates; Catalyst surface area: 102.0 m$^2$/gm; Pore volume N$_2$: 0.406 cc/gm; Pore area: 68.6 m$^2$/gm; Bulk density: 1.43 gm/cc. |
| Y | Magnesium oxide/ AB1 | Particle size: 1/16 inch cylindrical extrudates; Catalyst surface area: 18.1 m$^2$/gm; Pore volume N$_2$: 0.298 cc/gm; Pore area: 52.9 m$^2$/gm; Bulk density: 1.78 gm/cc. |
| Z | Silicon dioxide/ AB1 | Particle size: 1/16 inch cylindrical extrudates; Catalyst surface area: 33.7 m$^2$/gm; Pore volume N$_2$: 0.496 cc/gm; Pore area: 81.0 m$^2$/gm; Bulk density: 1.06 gm/cc. |
| AA | Aluminum oxide/ lanthanum meta-phosphate | Particle size: 1/16 inch cylindrical extrudates; Catalyst surface area: 86.0 m$^2$/gm; Pore volume N$_2$: 0.327 cc/gm; Pore area: 129.5 m$^2$/gm; Bulk density: 1.57 gm/cc. |
| BB | Silicon dioxide/ lanthanum meta-phosphate | Particle size: 1/16 inch cylindrical extrudates; Catalyst surface area: 38.7 m$^2$/gm; Pore volume N$_2$: 0.656 cc/gm; Pore area: 90.5 m$^2$/gm; Bulk density: 0.99 gm/cc. |
| CC | Titanium dioxide (anatase)/AB1/ZnO (2 wt. %) | Particle size: 1/16 inch cylindrical extrudates; Catalyst surface area: 90.4 m$^2$/gm; Pore volume N$_2$: 0.427 cc/gm; Pore area: 74.5 m$^2$/gm; Bulk density: 1.49 gm/cc. |
| DD | Titanium dioxide (anatase)/AB1/ZnO (4 wt. %) | Particle size: 1/16 inch cylindrical extrudates; Catalyst surface area: 78.3 m$^2$/gm; Pore volume N$_2$: 0.412 cc/gm; Pore area: 75.1 m$^2$/gm; Bulk density: 1.42 gm/cc. |
| EE | Titanium dioxide (anatase)/AB1/ Nb$_2$O$_5$ (4 wt. %) | Particle size: 1/16 inch cylindrical extrudates; Catalyst surface area: 102.2 m$^2$/gm; Pore volume N$_2$: 0.407 cc/gm; Pore area: 75.4 m$^2$/gm; Bulk density: 1.44 gm/cc. |
| FF | Titanium dioxide (anatase)/AB1/ NaBF$_4$ (8 wt. %) | Particle size: 1/16 inch cylindrical extrudates; Catalyst surface area: 22.5 m$^2$/gm; Pore volume N$_2$: 0.421 cc/gm; Pore area: 55.8 m$^2$/gm; Bulk density: 1.38 gm/cc. |
| GG | Titanium dioxide (anatase)/sodium dihydrogen phosphate; Ti:P atom ratio = 5.7:1 | Particle size: 1/16 inch cylindrical extrudates; Catalyst surface area: 117.1 m$^2$/gm; Pore volume N$_2$: 0.321 cc/gm; Pore area: 85.7 m$^2$/gm; Bulk density: 1.64 gm/cc. |
| HH | Titanium dioxide (anatase)/disodium dihydrogen pyro-phosphate; Ti:P atom ratio = 5.7:1 | Particle size: 1/16 inch cylindrical extrudates; Catalyst surface area: 133.5 m$^2$/gm; Pore N$_2$: 0.291 cc/gm; Pore area: 89.6 m$^2$/gm; Bulk denisity: 1.66 gm/cc. |
| II | Titanium dioxide (anatase)/disodium hydrogen phosphate; Ti:P atom ratio = 5.7:1 | Particle size: 1/16 inch cylindrical extrudates; Catalyst surface area: 117/4 m$^2$/gm; Pore volume N$_2$: 0.346 cc/gm; Pore area 86.5 m$^2$/gm; Bulk density: 1.53 gm/cc. |
| JJ | Titanium dioxide (anatase)/sodium phosphate; Ti:P atom ratio = 5.7:1 | Particle size: 1/16 inch cylindrical extrudates; Catalyst surface area: 88.4 m$^2$/gm; Pore volume N$_2$: 0.365 cc/gm; Pore area: 76.90 m$^2$/gm; Bulk density: 1.48 gm/cc. |

For each run the tubular reaction system was brought up to the designated conditions. The ammonia feed was established first, then the DETA-MEA feed. After a sufficient line out period, a two hour timed run was conducted and a sample taken. The temperature was then adjusted for the next experiment. The above procedure was repeated for each of the examples.

The catalysts employed in the examples hereinafter were prepared as follows:

Catalyst A: Obtained from Norton Company, Akron, Ohio

Catalyst B: Obtained from Norton Company, Akron, Ohio.

Catalyst C: Obtained from Norton Company, Akron, Ohio.

Catalyst D: Obtained from Norton Company, Akron, Ohio.

Catalyst E: Catalyst C pellets (140 grams) were added to a solution of boric acid (5.07 grams) in methanol (94.2 grams). The methanol was removed using a Buchi rotary evaporator. The catalyst was dried at a temperature of 100° C. for a period of 1 hour and then calcined at a temperature of 400° C. for a period of 16 hours.

Catalyst F: Catalyst C pellets (140 grams) were added to a solution of ammonium tetrafluoroborate (2.86 grams) in water Enough solution was prepared to completely wet the pellets. The resulting slurry was allowed to stand for a period of 1 hour at room temperature. The catalyst was dried at a temperature of 100° C. for a period of 1 hour and then calcined at a temperature of 400° C. for a period of 16 hours.

Catalyst G: Catalyst C pellets (140.1 grams) were added to a solution of sodium tetrafluoroborate (8.58 grams) in sufficient water to completely wet the pellets. The catalyst was dried at a temperature of 100° C. for a period 1 hour and then calcined at a temperature of 400° C. for a period of 16 hours.

Catalyst H: Catalyst C pellets (140.1 grams) were added to a solution of sodium tetrafluoroborate (8.58 grams) in sufficient water to completely wet the pellets. The catalyst was dried at a temperature of 100° C. for a period of 1 hour and then calcined at a temperature of 400° C. for a period of 16 hours.

Catalyst I: Catalyst C pellets (140.2 grams) were added to a solution of sodium metatungstate (1.43 grams) in sufficient water to completely wet the pellets. The catalyst was dried at a temperature of 100° C. for a period of 1 hour and then calcined at a temperature of 400° C. for a period of 16 hours.

Catalyst J: Catalyst C pellets (140.2 grams) were added to a solution of sodium metatungstate (2.86 grams) in sufficient water to completely wet the pellets. The catalyst was dried at a temperature of 100° C. for a period of 1 hour and then calcined at a temperature of 400° C. for a period of 16 hours.

Catalyst K: Catalyst C pellets (140.1 grams) were added to a solution of sodium metatungstate (5.71 grams) in sufficient water to completely wet the pellets. The catalyst was dried at a temperature of 100° C. for a period of 1 hour and then calcined at a temperature of 400° C. for a period of 16 hours.

Catalyst L: Catalyst C pellets (140.1 grams) were added to a solution of ammonium metatungstate (3.12 grams) in sufficient water to completely wet the pellets. The catalyst was dried at a temperature of 100° C. for a period of 1 hour and then calcined at a temperature of 400° C. for a period of 16 hours.

Catalyst M: Catalyst C pellets (140 grams) were added to a solution of ammonium metatungstate (6.24 grams) in sufficient water to completely wet the pellets. The catalyst was dried at a temperature of 100° C. for a period of 1 hour and then calcined at a temperature of 400° C. for a period of 16 hours.

Catalyst N: Catalyst C pellets (140 1 grams) were added to a solution of ammonium metatungstate (12.48 grams) in sufficient water to completely wet the pellets. The catalyst was dried at a temperature of 100° C. for a period of 1 hour and then calcined at a temperature of 400° C. for a period of 16 hours.

Catalyst O: Catalyst C pellets (140.1 rams) were added to a solution of lanthanum nitrate hexahydrate (7.59 grams) in sufficient water to completely wet the pellets. The catalyst was dried at a temperature of 100° C. for a period of 1 hour and then calcined at a temperature of 400° C. for a period of 16 hours.

Catalyst P: Catalyst C pellets (143.1 grams) were added to a solution of lanthanum nitrate hexahydrate (15.18 grams) in sufficient water to completely wet the pellets. The catalyst was dried at a temperature of 100° C. for a period of 1 hour and then calcined at a temperature of 400° C. for a period of 16 hours.

Catalyst Q: Catalyst C pellets (140 grams) were added to a solution of niobium pentethoxide (6.84 grams) in toluene (66 grams). Enough solution was added to completely immerse the pellets. The resulting slurry was stripped on a Buchi rotary evaporator. The catalyst was then calcined at a temperature of 400° C. for a period of 16 hours.

Catalyst R: Catalyst C pellets (140.4 grams) were added to a solution of sodium bicarbonate (3.87 grams) in sufficient water to completely wet the pellets. The catalyst was dried at a temperature of 100° C. for a period of 1 hour and then calcined at a temperature of 400° C. for a period of 16 hours.

Catalyst S: Catalyst C pellets (143.5 grams) were added to a solution of vanadium triisopropoxide (7.63 grams) in toluene (66.74 grams). Enough solution was added to completely wet the pellets. The resulting slurry was stripped under reduced pressure The catalyst was then calcined at a temperature of 400° C. for a period of 16 hours.

Catalyst T: Sodium trimetaphosphate (14.0 grams) was dissolved in a sufficient amount of water (82.7 grams) to wet the $TiO_2/SiO_2/Al_2O_3$ support (140 grams). After impregnation for a period of 1 hour at room temperature, the catalyst was dried at a temperature of 100° C. for a period of 1 hour and then calcined at a temperature of 400° C. for a period of 16 hours.

Catalyst U: Sodium trimetaphosphate (14.13 grams) was dissolved in water (56.0 grams) and isopropanol (87.0 grams). The $TiO_2/SiO_2$ support (140 grams) was impregnated with the solution. The catalyst was dried at a temperature of 100° C. for a period of 1 hour and then calcined at a temperature of 400° C. for a period of 16 hours.

Catalyst V: Sodium trimetaphosphate (14.05 grams) was dissolved in a sufficient amount of water (85.92 grams) to wet the $TiO_2/SiO_2$ support (140 grams). After impregnation for a period of 1 hour at room temperature, the catalyst was dried at a temperature of 100° C. for a period of 1 hour and then calcined at a temperature of 400° C. for a period of 16 hours.

Catalyst W: Obtained from Norton Company. Akron, Ohio.

Catalsyt X: Obtained from Norton Company, Akron, Ohio.

Catalyst Y: Obtained from Norton Company, Akron, Ohio.

Catalyst Z: Obtained from Norton Company, Akron, Ohio.

Catalsyt AA: Obtained from Norton Company, Akron, Ohio.

Catalyst BB: Obtained from Norton Company, Akron, Ohio.

Catalyst CC: Catalyst C pellets (140.5 grams) were added to a solution of zinc nitrate hexahydrate (10.45 grams) in sufficient water to completely wet the pellets.

The catalyst was dried at a temperature of 100° C. for a period of 1 hour and then calcined at a temperature of 400° C. for a period of 16 hours.

Catalyst DD: Catalyst C pellets (140.78 grams) were added to a solution of zinc nitrate hexahydrate (20.88 grams) in sufficient water to completely wet the pellets. The catalyst was dried at a temperature of 100° C. for a period of 1 hour and then calcined at a temperature of 400° C. for a period of 16 hours.

Catalyst EE: Catalyst C pellets (140.1 grams) were added to a solution of niobium pentethoxide (13.68 grams) in toluene (66.2 grams). Enough solution was added to completely immerse the pellets. The resulting slurry was allowed to stand for a period of 1 hour. The catalyst was dried at a temperature of 100° C. for a period of 1 hour and then calcined at a temperature of 400° C. for a period of 16 hours.

Catalyst FF: Catalyst C pellets (140.15 grams) were added to a solution of sodium tetrafluoroborate (8.58 grams) in sufficient water to completely wet the pellets. The catalyst was dried at a temperature of 100° C. for a period of 1 hour and then calcined at a temperature of 400° C. for a period of 16 hours.

Catalyst GG: Obtained from Norton Company, Akron, Ohio.

Catalyst HH: Obtained from Norton Company, Akron, Ohio.

Catalyst II: Obtained from Norton Company, Akron, Ohio.

Catalyst JJ: Obtained from Norton Company, Akron, Ohio.

TABLE I

| Example No. | 1 | 2 | 3 | 4 | 5 | 6 | 7 | 8 | 9 |
|---|---|---|---|---|---|---|---|---|---|
| Catalyst Type | A | A | A | A | A | A | A | A | A |
| Catalyst weight, gm | 78.74 | 78.74 | 78.74 | 78.74 | 78.74 | 78.74 | 78.74 | 78.74 | 78.74 |
| Pressure, psig | 606 | 603 | 603 | 602 | 603 | 603 | 603 | 598 | 603 |
| Temperature, °C. | 270 | 270 | 280 | 269 | 259 | 280 | 280 | 270.1 | 270 |
| Time on organics, hrs. | 4.5 | 4.5 | 28.5 | 51.5 | 71.5 | 76.5 | 100.5 | 120 | 167.5 |
| Duration of run, hrs. | 2 | 2 | 2 | 2 | 2 | 2 | 2 | 2 | 2 |
| MEA SV, gmol/hr/kgcat | 3.46 | 3.84 | 3.94 | 3.87 | 3.77 | 3.63 | 3.78 | 3.83 | 3.81 |
| DETA/MEA mole ratio | 1.00 | 1.00 | 1.00 | 1.00 | 1.00 | 1.00 | 1.00 | 1.00 | 1.00 |
| $NH_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 0.874 | 1.232 | 1.585 | 0.847 | 0.433 | 1.400 | 1.565 | 0.773 | 0.551 |
| MEA | 12.473 | 11.945 | 7.517 | 13.370 | 17.877 | 6.436 | 7.199 | 12.823 | 16.111 |
| PIP | 0.965 | 1.116 | 1.414 | 1.070 | 0.651 | 1.400 | 1.451 | 1.028 | 0.807 |
| DETA | 39.228 | 39.867 | 35.453 | 41.854 | 47.014 | 35.668 | 35.534 | 41.213 | 44.005 |
| AEEA | 1.227 | 1.108 | 0.479 | 1.371 | 2.399 | 0.486 | 0.502 | 1.388 | 1.922 |
| AEP | 1.183 | 1.533 | 1.814 | 1.158 | 0.708 | 1.977 | 1.886 | 1.126 | 0.824 |
| HEP | 0.000 | 0.000 | 0.000 | 0.000 | 0.000 | 0.000 | 0.000 | 0.000 | 0.000 |
| TAEA | 2.760 | 2.694 | 2.611 | 2.646 | 2.564 | 2.683 | 2.567 | 2.662 | 2.560 |
| 1-TETA | 12.867 | 13.297 | 13.364 | 12.613 | 12.062 | 14.170 | 13.658 | 12.943 | 12.257 |
| DAEP | 0.519 | 0.744 | 0.968 | 0.425 | 0.180 | 1.018 | 0.985 | 0.432 | 0.232 |
| PEEDA | 0.110 | 0.111 | 0.154 | 0.082 | 0.152 | 0.059 | 0.710 | 0.336 | 0.206 |
| DPE | 0.118 | 0.120 | 0.127 | 0.085 | 0.097 | 0.087 | 0.322 | 0.227 | 0.120 |
| AE-TAEA | 4.110 | 3.926 | 4.516 | 3.704 | 2.640 | 4.497 | 4.572 | 3.788 | 3.014 |
| 1-TEPA | 7.436 | 7.679 | 8.979 | 7.093 | 5.411 | 8.403 | 9.298 | 7.467 | 6.239 |
| AE-DAEP | 0.140 | 0.117 | 0.182 | 0.100 | 0.097 | 0.000 | 0.808 | 0.390 | 0.275 |
| AE-PEEDA | 0.099 | 0.100 | 0.129 | 0.096 | 0.000 | 0.720 | 0.173 | 0.127 | 0.099 |
| iAE-PEEDA | 0.000 | 0.000 | 0.000 | 0.000 | 0.000 | 0.000 | 0.000 | 0.000 | 0.000 |
| AE-DPE | 0.304 | 0.169 | 0.301 | 0.160 | 0.065 | 0.160 | 1.020 | 0.739 | 0.467 |
| BPEA | 0.639 | 0.578 | 0.844 | 0.573 | 0.045 | 0.211 | 1.060 | 0.835 | 0.435 |
| Others | 8.068 | 6.841 | 11.264 | 5.414 | 2.775 | 11.735 | 8.190 | 6.222 | 3.695 |
| MEA conversion, % | 66.60 | 68.06 | 79.87 | 63.84 | 52.17 | 82.68 | 80.79 | 66.20 | 56.64 |
| DETA conversion, % | 37.56 | 36.64 | 43.59 | 32.72 | 25.25 | 42.94 | 43.64 | 35.44 | 29.62 |
| Acyclic(N4), wt. % | 95.43 | 94.25 | 92.75 | 96.27 | 97.15 | 93.54 | 88.94 | 94.00 | 96.37 |
| Acyclic(N5), wt. % | 90.71 | 92.25 | 90.26 | 92.08 | 97.50 | 92.20 | 81.92 | 84.33 | 87.88 |
| $\Sigma(N5)/\Sigma(N4)$, weight ratio | 0.78 | 0.74 | 0.87 | 0.74 | 0.55 | 0.78 | 0.93 | 0.80 | 0.68 |
| Acyclic(N4)/cyclic(<=N4), weight ratio | 5.40 | 4.41 | 3.57 | 5.41 | 8.18 | 3.71 | 3.03 | 4.96 | 6.77 |

| Example No. | 10 | 11 | 12 | 13 | 14 | 15 | 16 | 17 | 18 |
|---|---|---|---|---|---|---|---|---|---|
| Catalyst Type | A | A | A | A | A | A | A | A | A |
| Catalyst weight, gm | 78.74 | 78.74 | 78.74 | 78.74 | 78.74 | 78.74 | 78.74 | 78.74 | 78.74 |
| Pressure, psig | 603 | 604 | 603 | 604 | 603 | 603 | 603 | 604 | 604 |
| Temperature, °C. | 280 | 259 | 269 | 260 | 280 | 270 | 280 | 270 | 270 |
| Time on organics, hrs. | 172.5 | 191.5 | 196.5 | 214.5 | 219.5 | 238.5 | 243.5 | 262.5 | 266 |
| Duration of run, hrs. | 2 | 2 | 2 | 2 | 2 | 2 | 2 | 2 | 2 |
| MEA SV, gmol/hr/kgcat | 3.71 | 3.89 | 3.89 | 3.81 | 3.78 | 3.79 | 3.51 | 3.51 | 3.71 |
| DETA/MEA mole ratio | 1.00 | 1.00 | 1.00 | 1.00 | 1.00 | 1.00 | 1.00 | 1.00 | 1.00 |
| $NH_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 1.445 | 0.461 | 0.791 | 0.658 | 1.456 | 0.910 | 1.122 | 1.072 | 1.017 |
| MEA | 5.976 | 18.787 | 12.858 | 18.141 | 6.956 | 13.064 | 13.239 | 11.990 | 12.608 |
| PIP | 1.387 | 0.691 | 1.023 | 0.811 | 1.416 | 1.148 | 1.024 | 1.234 | 1.186 |
| DETA | 33.430 | 47.586 | 40.957 | 45.580 | 35.955 | 41.603 | 42.624 | 40.482 | 40.928 |
| AEEA | 0.443 | 2.282 | 1.404 | 1.879 | 0.493 | 1.322 | 1.350 | 1.216 | 1.269 |
| AEP | 1.827 | 0.682 | 1.103 | 0.881 | 1.832 | 1.184 | 1.192 | 1.267 | 1.191 |
| HEP | 0.000 | 0.000 | 0.000 | 0.000 | 0.000 | 0.000 | 0.000 | 0.000 | 0.000 |
| TAEA | 2.553 | 2.310 | 2.681 | 2.359 | 2.571 | 2.654 | 2.361 | 2.647 | 2.627 |
| 1-TETA | 13.506 | 10.647 | 12.732 | 10.997 | 13.341 | 12.720 | 11.438 | 12.833 | 12.755 |
| DAEP | 1.004 | 0.173 | 0.386 | 0.275 | 0.888 | 0.410 | 0.490 | 0.472 | 0.422 |
| PEEDA | 0.710 | 0.146 | 0.310 | 0.222 | 0.654 | 0.336 | 0.382 | 0.369 | 0.339 |

TABLE I-continued

| | | | | | | | | | |
|---|---|---|---|---|---|---|---|---|---|
| DPE | 0.335 | 0.085 | 0.184 | 0.086 | 0.309 | 0.196 | 0.271 | 0.070 | 0.135 |
| AE-TAEA | 4.645 | 2.372 | 3.629 | 2.706 | 4.368 | 3.735 | 3.951 | 3.951 | 3.751 |
| 1-TEPA | 9.538 | 4.500 | 6.990 | 5.378 | 8.945 | 7.412 | 6.576 | 7.610 | 7.246 |
| AE-DAEP | 0.848 | 0.213 | 0.276 | 0.183 | 0.700 | 0.300 | 0.385 | 0.331 | 0.291 |
| AE-PEEDA | 0.185 | 0.000 | 0.057 | 0.056 | 0.084 | 0.065 | 0.085 | 0.035 | 0.028 |
| iAE-PEEDA | 0.000 | 0.000 | 0.000 | 0.000 | 0.000 | 0.000 | 0.000 | 0.000 | 0.000 |
| AE-DPE | 1.089 | 0.315 | 0.667 | 0.434 | 1.016 | 0.698 | 0.091 | 0.064 | 0.062 |
| BPEA | 1.026 | 0.247 | 0.634 | 0.403 | 0.932 | 0.638 | 0.093 | 0.594 | 0.053 |
| Others | 9.232 | 1.904 | 3.598 | 2.311 | 6.162 | 3.686 | 6.348 | 5.045 | 5.231 |
| MEA conversion, % | 83.70 | 48.64 | 64.40 | 50.59 | 80.69 | 64.55 | 64.31 | 67.22 | 65.36 |
| DETA conversion, % | 45.82 | 22.68 | 32.60 | 26.22 | 40.67 | 32.91 | 31.71 | 34.22 | 33.16 |
| Acyclic(N4), wt. % | 88.68 | 96.98 | 94.60 | 95.81 | 89.58 | 94.23 | 92.35 | 94.45 | 94.49 |
| Acyclic(N5), wt. % | 81.83 | 89.87 | 86.66 | 88.25 | 82.97 | 86.76 | 94.15 | 91.86 | 96.21 |
| $\Sigma$(N5)/$\Sigma$(N4), weight ratio | 0.96 | 0.57 | 0.75 | 0.66 | 0.90 | 0.79 | 0.75 | 0.77 | 0.70 |
| Acyclic(N4)/cyclic($<=$N4), weight ratio | 3.05 | 7.29 | 5.13 | 5.86 | 3.12 | 4.70 | 4.11 | 4.54 | 4.70 |

TABLE II

| Example No. | 19 | 20 | 21 | 22 | 23 | 24 | 25 | 26 | 27 |
|---|---|---|---|---|---|---|---|---|---|
| Catalyst Type | B | B | B | B | B | B | B | B | B |
| Catalyst weight, gm | 84.66 | 84.66 | 84.66 | 84.66 | 84.66 | 84.66 | 84.66 | 84.66 | 84.66 |
| Pressure, psig | 598 | 598 | 598 | 598 | 598 | 599 | 599 | 598 | 603 |
| Temperature, °C. | 270 | 270 | 280 | 259 | 269 | 259 | 280 | 280 | 270.1 |
| Time on organics, hrs. | 4.5 | 23.5 | 28.5 | 47.5 | 51.5 | 71.5 | 76.5 | 100.5 | 120 |
| Duration of run, hrs. | 2 | 2 | 2 | 2 | 2 | 2 | 2 | 2 | 2 |
| MEA SV, gmol/hr/kgcat | 2.95 | 2.82 | 2.91 | 2.90 | 2.89 | 2.81 | 2.72 | 2.85 | 2.92 |
| DETA/MEA mole ratio | 1.00 | 1.00 | 1.00 | 1.00 | 1.00 | 1.00 | 1.00 | 1.00 | 1.00 |
| NH3/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 0.387 | 0.451 | 0.942 | 0.263 | 0.472 | 0.251 | 0.768 | 0.805 | 0.481 |
| MEA | 18.211 | 18.550 | 12.561 | 24.117 | 18.908 | 22.270 | 11.181 | 11.851 | 17.815 |
| PIP | 0.711 | 0.768 | 1.105 | 0.411 | 0.731 | 0.450 | 1.013 | 1.082 | 0.763 |
| DETA | 45.762 | 47.529 | 39.025 | 52.023 | 46.902 | 51.519 | 38.122 | 38.925 | 46.516 |
| AEEA | 1.902 | 2.077 | 1.192 | 2.582 | 2.111 | 2.804 | 1.247 | 1.088 | 2.005 |
| AEP | 0.846 | 0.787 | 1.214 | 0.446 | 0.718 | 0.519 | 1.229 | 1.254 | 0.767 |
| HEP | 0.000 | 0.000 | 0.000 | 0.000 | 0.000 | 0.000 | 0.000 | 0.000 | 0.000 |
| TAEA | 2.031 | 2.252 | 2.423 | 1.674 | 2.273 | 2.036 | 2.764 | 2.429 | 2.345 |
| 1-TETA | 10.921 | 11.106 | 12.012 | 8.125 | 11.140 | 9.812 | 13.613 | 12.691 | 11.657 |
| DAEP | 0.186 | 0.202 | 0.477 | 0.080 | 0.175 | 0.097 | 0.523 | 0.523 | 0.191 |
| PEEDA | 0.159 | 0.178 | 0.147 | 0.057 | 0.157 | 0.084 | 0.424 | 0.443 | 0.174 |
| DPE | 0.084 | 0.096 | 0.095 | 0.052 | 0.114 | 0.086 | 0.094 | 0.303 | 0.105 |
| AE-TAEA | 2.341 | 2.390 | 3.575 | 1.205 | 2.444 | 1.558 | 4.042 | 3.853 | 2.650 |
| 1-TEPA | 3.918 | 5.171 | 7.286 | 2.186 | 6.082 | 3.822 | 8.123 | 8.109 | 6.868 |
| AE-DAEP | 0.366 | 0.189 | 0.131 | 0.129 | 0.081 | 0.000 | 0.417 | 0.508 | 0.093 |
| AE-PEEDA | 0.080 | 0.079 | 0.101 | 0.068 | 0.000 | 0.000 | 0.113 | 0.139 | 0.000 |
| iAE-PEEDA | 0.000 | 0.000 | 0.000 | 0.000 | 0.000 | 0.000 | 0.000 | 0.000 | 0.000 |
| AE-DPE | 0.403 | 0.061 | 0.264 | 0.051 | 0.078 | 0.066 | 0.220 | 0.797 | 0.055 |
| BPEA | 0.328 | 0.276 | 0.649 | 0.076 | 0.291 | 0.128 | 0.215 | 0.930 | 0.371 |
| Others | 6.126 | 2.669 | 9.532 | 1.845 | 2.513 | 1.388 | 8.524 | 7.390 | 2.594 |
| MEA conversion, % | 51.16 | 50.15 | 66.20 | 34.36 | 49.36 | 40.71 | 70.01 | 68.44 | 52.59 |
| DETA conversion, % | 27.06 | 24.09 | 37.59 | 15.85 | 25.35 | 18.49 | 39.22 | 38.40 | 26.43 |
| Acyclic(N4), wt. % | 96.80 | 96.56 | 95.26 | 98.11 | 96.78 | 97.79 | 94.03 | 92.26 | 96.75 |
| Acyclic(N5), wt. % | 84.17 | 92.59 | 90.47 | 91.27 | 94.99 | 96.53 | 92.65 | 83.44 | 94.83 |
| $\Sigma$(N5)/$\Sigma$(N4), weight ratio | 0.56 | 0.59 | 0.79 | 0.37 | 0.65 | 0.46 | 0.75 | 0.87 | 0.69 |
| Acyclic(N4)/cyclic($<=$N4), weight ratio | 6.52 | 6.58 | 4.75 | 9.37 | 7.08 | 9.58 | 4.99 | 4.20 | 7.00 |

| Example No. | 28 | 29 | 30 | 31 | 32 | 33 | 34 | 35 | 36 | 37 |
|---|---|---|---|---|---|---|---|---|---|---|
| Catalyst Type | B | B | B | B | B | B | B | B | B | B |
| Catalyst weight, gm | 84.66 | 84.66 | 84.66 | 84.66 | 84.66 | 84.66 | 84.66 | 84.66 | 84.66 | 84.66 |
| Pressure, psig | 598 | 598 | 598 | 598 | 598 | 599 | 599 | 604 | 604 | 604 |
| Temperature, °C. | 270 | 280 | 259 | 269 | 260 | 280 | 270 | 280 | 270 | 270 |
| Time on organics, hrs. | 167.5 | 172.5 | 191.5 | 196.5 | 214.5 | 219.5 | 238.5 | 243.5 | 262.5 | 266 |
| Duration of run, hrs. | 2 | 2 | 2 | 2 | 2 | 2 | 2 | 2 | 2 | 2 |
| MEA SV, gmol/hr/kgcat | 2.92 | 2.51 | 2.94 | 2.91 | 3.37 | 2.82 | 2.90 | 2.83 | 2.69 | 2.83 |
| DETA/MEA mole ratio | 1.00 | 1.00 | 1.00 | 1.00 | 1.00 | 1.00 | 1.00 | 1.00 | 1.00 | 1.00 |
| NH3/MEA mole ratio | 5.97 | 5.97 | 5.97 | 5.97 | 5.97 | 5.97 | 5.97 | 5.97 | 5.97 | 5.97 |
| Crude product composition, wt. % | | | | | | | | | | |
| EDA | 0.768 | 0.935 | 0.259 | 0.554 | 0.303 | 0.984 | 0.731 | 1.166 | 0.772 | 0.727 |
| MEA | 11.617 | 9.895 | 22.504 | 16.654 | 25.518 | 10.278 | 15.594 | 9.688 | 14.486 | 15.223 |
| PIP | 1.012 | 1.112 | 0.501 | 0.801 | 0.351 | 1.163 | 0.969 | 1.258 | 0.984 | 0.967 |
| DETA | 38.660 | 37.291 | 50.906 | 44.882 | 53.431 | 38.532 | 43.211 | 37.652 | 42.240 | 43.621 |
| AEEA | 1.321 | 0.909 | 2.608 | 1.955 | 2.502 | 0.852 | 1.707 | 0.755 | 1.601 | 1.652 |
| AEP | 1.097 | 1.308 | 0.480 | 0.827 | 0.406 | 1.361 | 1.004 | 1.440 | 1.010 | 0.980 |
| HEP | 0.000 | 0.000 | 0.000 | 0.000 | 0.000 | 0.000 | 0.000 | 0.000 | 0.000 | 0.000 |
| TAEA | 2.638 | 2.623 | 2.028 | 2.607 | 1.424 | 2.641 | 2.659 | 2.671 | 2.744 | 2.666 |
| 1-TETA | 12.643 | 12.534 | 9.067 | 11.734 | 6.423 | 12.393 | 11.936 | 12.701 | 12.439 | 12.081 |
| DAEP | 0.461 | 0.560 | 0.119 | 0.241 | 0.079 | 0.538 | 0.298 | 0.622 | 0.320 | 0.282 |
| PEEDA | 0.353 | 0.455 | 0.081 | 0.211 | 0.068 | 0.431 | 0.263 | 0.498 | 0.276 | 0.248 |

TABLE II-continued

| | | | | | | | | | | |
|---|---|---|---|---|---|---|---|---|---|---|
| DPE | 0.353 | 0.332 | 0.103 | 0.133 | 0.127 | 0.308 | 0.161 | 0.109 | 0.118 | 0.100 |
| AE-TAEA | 3.917 | 4.248 | 1.719 | 2.992 | 1.105 | 4.215 | 3.423 | 4.647 | 3.605 | 3.411 |
| 1-TEPA | 8.051 | 8.471 | 3.147 | 5.870 | 1.995 | 8.144 | 6.762 | 8.696 | 6.609 | 6.249 |
| AE-DAEP | 0.479 | 0.536 | 0.073 | 0.161 | 0.074 | 0.499 | 0.236 | 0.581 | 0.204 | 0.181 |
| AE-PEEDA | 0.163 | 0.150 | 0.064 | 0.000 | 0.053 | 0.132 | 0.054 | 0.123 | 0.034 | 0.030 |
| iAE-PEEDA | 0.000 | 0.000 | 0.000 | 0.000 | 0.000 | 0.000 | 0.000 | 0.000 | 0.000 | 0.000 |
| AE-DPE | 0.793 | 0.918 | 0.151 | 0.456 | 0.092 | 0.892 | 0.536 | 0.306 | 0.061 | 0.063 |
| BPEA | 0.949 | 1.033 | 0.115 | 0.459 | 0.108 | 0.885 | 0.576 | 0.724 | 0.059 | 0.402 |
| Others | 7.450 | 7.630 | 1.713 | 2.553 | 2.042 | 6.020 | 3.491 | 7.953 | 4.671 | 3.839 |
| MEA conversion, % | 68.95 | 73.17 | 39.26 | 54.71 | 30.82 | 71.85 | 58.06 | 73.87 | 60.45 | 58.58 |
| DETA conversion, % | 38.60 | 39.91 | 18.34 | 27.46 | 13.91 | 37.28 | 30.93 | 39.64 | 31.46 | 29.46 |
| Acyclic(N4), wt. % | 92.90 | 91.84 | 97.34 | 96.08 | 96.64 | 92.17 | 95.29 | 92.60 | 95.51 | 95.90 |
| Acyclic(N5), wt. % | 83.45 | 82.83 | 92.34 | 89.17 | 90.46 | 83.69 | 87.90 | 88.50 | 96.63 | 93.47 |
| Σ(N5)/Σ(N4), weight ratio | 0.88 | 0.93 | 0.46 | 0.67 | 0.42 | 0.91 | 0.76 | 0.91 | 0.67 | 0.67 |
| Acyclic(N4)/cyclic(<=N4), weight ratio | 4.66 | 4.02 | 8.64 | 6.48 | 7.62 | 3.95 | 5.42 | 3.91 | 5.61 | 5.72 |

TABLE III

| Example No. | 38 | 39 | 40 | 41 | 42 | 43 | 44 | 45 | 46 |
|---|---|---|---|---|---|---|---|---|---|
| Catalyst Type | C | C | C | C | C | C | C | C | C |
| Catalyst weight, gm | 75 | 75 | 75 | 75 | 75 | 75 | 75 | 75 | 75 |
| Pressure, psig | 607.5 | 600 | 600 | 600 | 600 | 600 | 600 | 600 | 600 |
| Temperature, °C. | 267.9 | 267.8 | 277.8 | 259.9 | 270.1 | 259.9 | 280.1 | 269.6 | 269 |
| Time on organics, hrs. | 5 | 7.5 | 26 | 31.5 | 50 | 55.5 | 74 | 78 | 80 |
| Duration of run, hrs. | 1 | 1 | 2 | 2 | 2 | 2 | 2 | 2 | 1.5 |
| MEA SV, gmol/hr/kgcat | 8.48 | 8.57 | 4.17 | 3.96 | 3.90 | 4.22 | 4.15 | 4.01 | 3.97 |
| DETA/MEA mole ratio | 1.00 | 1.00 | 1.00 | 1.00 | 1.00 | 1.00 | 1.00 | 1.00 | 1.00 |
| NH3/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 0.673 | 0.822 | 1.742 | 0.612 | 1.367 | 0.688 | 2.430 | 1.370 | 1.341 |
| MEA | 33.641 | 24.246 | 13.234 | 26.804 | 16.396 | 24.443 | 8.046 | 15.672 | 15.462 |
| PIP | 0.585 | 1.113 | 0.000 | 0.823 | 1.584 | 0.886 | 1.994 | 1.506 | 1.484 |
| DETA | 51.838 | 49.325 | 40.936 | 52.117 | 49.168 | 51.098 | 40.046 | 47.408 | 47.941 |
| AEEA | 2.205 | 0.926 | 0.312 | 1.512 | 0.754 | 1.506 | 0.202 | 0.925 | 0.850 |
| AEP | 0.502 | 0.953 | 1.969 | 0.613 | 1.431 | 0.666 | 2.287 | 1.330 | 1.326 |
| HEP | 0.000 | 0.000 | 0.000 | 0.000 | 0.000 | 0.000 | 0.000 | 0.000 | 0.000 |
| TAEA | 0.488 | 2.104 | 2.220 | 1.660 | 2.270 | 1.751 | 2.342 | 2.219 | 2.195 |
| 1-TETA | 4.586 | 9.252 | 11.293 | 7.569 | 10.817 | 7.792 | 12.031 | 10.555 | 10.356 |
| DAEP | 0.000 | 0.167 | 0.922 | 0.114 | 0.307 | 0.112 | 1.101 | 0.290 | 0.271 |
| PEEDA | 0.000 | 0.113 | 0.678 | 0.000 | 0.217 | 0.075 | 0.791 | 0.209 | 0.196 |
| DPE | 0.000 | 0.000 | 0.205 | 0.000 | 0.000 | 0.000 | 0.096 | 0.000 | 0.000 |
| AE-TAEA | 0.234 | 1.259 | 3.575 | 0.885 | 2.431 | 1.011 | 3.561 | 2.057 | 2.091 |
| 1-TEPA | 0.541 | 2.471 | 6.977 | 1.667 | 5.274 | 1.895 | 7.683 | 4.176 | 3.991 |
| AE-DAEP | 0.000 | 0.000 | 0.676 | 0.000 | 0.134 | 0.000 | 0.783 | 0.149 | 0.124 |
| AE-PEEDA | 0.000 | 0.000 | 0.710 | 0.000 | 0.089 | 0.000 | 0.718 | 0.000 | 0.000 |
| iAE-PEEDA | 0.000 | 0.000 | 0.000 | 0.000 | 0.000 | 0.000 | 0.000 | 0.000 | 0.000 |
| AE-DPE | 0.000 | 0.000 | 0.882 | 0.000 | 0.270 | 0.091 | 1.072 | 0.423 | 0.395 |
| BPEA | 0.000 | 0.000 | 0.729 | 0.000 | 0.340 | 0.077 | 0.874 | 0.385 | 0.362 |
| Others | 0.455 | 0.399 | 3.890 | 0.125 | 1.112 | 0.488 | 5.301 | 1.685 | 1.506 |
| MEA conversion, % | 6.59 | 32.47 | 63.69 | 25.82 | 54.29 | 31.29 | 78.37 | 56.01 | 56.32 |
| DETA conversion, % | 14.45 | 18.36 | 33.25 | 14.28 | 23.51 | 14.64 | 36.03 | 20.92 | 19.52 |
| Acyclic(N4), wt. % | 100.00 | 97.59 | 88.22 | 98.78 | 96.15 | 98.08 | 87.85 | 96.23 | 96.41 |
| Acyclic(N5), wt. % | 100.00 | 100.00 | 77.88 | 100.00 | 90.24 | 94.53 | 76.53 | 86.69 | 87.22 |
| Σ(N5)/Σ(N4), weight ratio | 0.15 | 0.32 | 0.88 | 0.27 | 0.63 | 0.32 | 0.90 | 0.54 | 0.53 |
| Acyclic(N4)/cyclic(<=N4), weight ratio | 4.67 | 4.84 | 3.58 | 5.96 | 3.70 | 5.49 | 2.29 | 3.83 | 3.83 |

TABLE IV

| Example No. | 47 | 48 | 49 | 50 | 51 | 52 | 53 | 54 | 55 |
|---|---|---|---|---|---|---|---|---|---|
| Catalyst Type | D | D | D | D | D | D | D | D | D |
| Catalyst weight, gm | 68.38 | 68.38 | 68.38 | 68.38 | 68.38 | 68.38 | 68.38 | 68.38 | 68.38 |
| Pressure, psig | 602 | 602 | 602 | 602 | 602 | 603 | 603 | 602 | 602 |
| Temperature, °C. | 270 | 270 | 280 | 259 | 269 | 259 | 280 | 280 | 270.1 |
| Time on organics, hrs. | 4.5 | 23.5 | 28.5 | 47.5 | 51.5 | 71.5 | 76.5 | 100.5 | 120 |
| Duration of run, hrs. | 2 | 2 | 2 | 2 | 2 | 2 | 2 | 2 | 2 |
| MEA SV, gmol/hr/kgcat | 3.96 | 3.87 | 4.09 | 3.96 | 3.90 | 3.87 | 3.92 | 3.90 | 4.03 |
| DETA/MEA mole ratio | 1.00 | 1.00 | 1.00 | 1.00 | 1.00 | 1.00 | 1.00 | 1.00 | 1.00 |
| NH3/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 0.223 | 0.361 | 0.675 | 0.212 | 0.396 | 0.180 | 0.730 | 0.795 | 0.461 |
| MEA | 24.445 | 22.069 | 16.449 | 26.799 | 21.362 | 24.727 | 13.740 | 14.037 | 20.260 |
| PIP | 0.470 | 0.526 | 0.892 | 0.297 | 0.553 | 0.298 | 0.888 | 0.897 | 0.585 |
| DETA | 53.878 | 51.806 | 46.950 | 56.278 | 50.889 | 55.710 | 44.046 | 42.839 | 49.907 |
| AEEA | 2.281 | 2.479 | 1.818 | 2.578 | 2.565 | 2.914 | 1.871 | 1.449 | 2.318 |
| AEP | 0.515 | 0.624 | 1.064 | 0.387 | 0.663 | 0.447 | 1.193 | 1.137 | 0.672 |
| HEP | 0.000 | 0.000 | 0.000 | 0.000 | 0.000 | 0.000 | 0.000 | 0.000 | 0.000 |
| TAEA | 1.420 | 1.640 | 2.118 | 1.210 | 1.747 | 1.411 | 2.465 | 2.237 | 1.931 |

TABLE IV-continued

| | | | | | | | | | | |
|---|---|---|---|---|---|---|---|---|---|---|
| 1-TETA | 7.238 | 7.768 | 10.879 | 5.638 | 8.217 | 6.704 | 12.235 | 11.091 | 9.032 | |
| DAEP | 0.092 | 0.160 | 0.324 | 0.058 | 0.188 | 0.079 | 0.480 | 0.476 | 0.204 | |
| PEEDA | 0.097 | 0.137 | 0.289 | 0.053 | 0.154 | 0.073 | 0.398 | 0.393 | 0.166 | |
| DPE | 0.075 | 0.095 | 0.046 | 0.052 | 0.063 | 0.100 | 0.355 | 0.333 | 0.191 | |
| AE-TAEA | 1.219 | 1.522 | 2.583 | 0.752 | 1.679 | 0.945 | 3.598 | 3.115 | 2.003 | |
| 1-TEPA | 2.039 | 2.628 | 5.427 | 1.366 | 3.512 | 1.934 | 6.530 | 6.472 | 4.096 | |
| AE-DAEP | 0.173 | 0.187 | 0.318 | 0.000 | 0.179 | 0.087 | 0.390 | 0.491 | 0.208 | |
| AE-PEEDA | 0.066 | 0.063 | 0.068 | 0.000 | 0.071 | 0.080 | 0.096 | 0.129 | 0.079 | |
| iAE-PEEDA | 0.000 | 0.000 | 0.000 | 0.000 | 0.000 | 0.000 | 0.000 | 0.000 | 0.000 | |
| AE-DPE | 0.141 | 0.121 | 0.160 | 0.073 | 0.175 | 0.115 | 0.175 | 0.301 | 0.139 | |
| BPEA | 0.101 | 0.141 | 0.381 | 0.047 | 0.197 | 0.060 | 0.186 | 0.732 | 0.292 | |
| Others | 2.821 | 3.594 | 4.790 | 1.260 | 3.582 | 1.974 | 6.576 | 7.895 | 3.856 | |
| MEA conversion, % | 34.76 | 40.66 | 56.27 | 27.73 | 42.89 | 34.28 | 64.11 | 62.93 | 46.18 | |
| DETA conversion, % | 14.55 | 17.21 | 25.83 | 9.80 | 19.14 | 12.00 | 31.61 | 32.77 | 21.21 | |
| Acyclic(N4), wt. % | 97.05 | 96.00 | 95.18 | 97.67 | 96.10 | 96.98 | 92.27 | 91.72 | 95.13 | |
| Acyclic(N5), wt. % | 87.14 | 89.01 | 89.63 | 94.66 | 89.31 | 89.37 | 92.28 | 85.30 | 89.48 | |
| Σ(N5)/Σ(N4), weight ratio | 0.42 | 0.48 | 0.65 | 0.32 | 0.56 | 0.38 | 0.69 | 0.77 | 0.59 | |
| Acyclic(N4)/cyclic(<=N4), weight ratio | 7.31 | 6.11 | 4.97 | 8.08 | 6.15 | 8.14 | 4.44 | 4.12 | 6.03 | |

| Example No. | 56 | 57 | 58 | 59 | 60 | 61 | 62 | 63 | 64 | 65 |
|---|---|---|---|---|---|---|---|---|---|---|
| Catalyst Type | D | D | D | D | D | D | D | D | D | D |
| Catalyst weight, gm | 68.38 | 68.38 | 68.38 | 68.38 | 68.38 | 68.38 | 68.38 | 68.38 | 68.38 | 68.38 |
| Pressure, psig | 602 | 602 | 603 | 602 | 603 | 603 | 602 | 603 | 603 | 603 |
| Temperature, °C. | 270 | 280 | 259 | 269 | 260 | 280 | 270 | 280 | 270 | 270 |
| Time on organics, hrs. | 167.5 | 172.5 | 191.5 | 196.5 | 214.5 | 219.5 | 238.5 | 243.5 | 262.5 | 266 |
| Duration of run, hrs. | 2 | 2 | 2 | 2 | 2 | 2 | 2 | 2 | 2 | 2 |
| MEA SV, gmol/hr/kgcat | 3.92 | 3.98 | 4.05 | 4.06 | 3.59 | 4.00 | 3.95 | 4.40 | 3.76 | 3.89 |
| DETA/MEA mole ratio | 1.00 | 1.00 | 1.00 | 1.00 | 1.00 | 1.00 | 1.00 | 1.00 | 1.00 | 1.00 |
| NH3/MEA mole ratio | 5.97 | 5.97 | 5.97 | 5.97 | 5.97 | 5.97 | 5.97 | 5.97 | 5.97 | 5.97 |
| Crude product composition, wt. % | | | | | | | | | | |
| EDA | 0.516 | 0.878 | 0.251 | 0.489 | 0.337 | 0.945 | 0.600 | 1.593 | 0.706 | 0.676 |
| MEA | 18.745 | 12.739 | 24.769 | 19.980 | 21.647 | 14.371 | 19.473 | 6.716 | 18.311 | 19.235 |
| PIP | 0.611 | 0.931 | 0.340 | 0.589 | 0.483 | 0.985 | 0.679 | 1.480 | 0.743 | 0.731 |
| DETA | 47.493 | 41.921 | 53.539 | 49.348 | 49.438 | 44.879 | 48.790 | 36.170 | 47.421 | 48.217 |
| AEEA | 2.331 | 1.424 | 2.555 | 2.352 | 2.505 | 1.539 | 2.260 | 0.475 | 2.170 | 2.155 |
| AEP | 0.691 | 1.141 | 0.402 | 0.686 | 0.479 | 1.175 | 0.770 | 1.905 | 0.803 | 0.752 |
| HEP | 0.000 | 0.000 | 0.000 | 0.000 | 0.000 | 0.000 | 0.000 | 0.000 | 0.000 | 0.000 |
| TAEA | 2.040 | 2.361 | 1.480 | 1.962 | 2.037 | 2.311 | 2.070 | 2.556 | 2.174 | 1.990 |
| 1-TETA | 9.416 | 11.410 | 6.735 | 8.956 | 8.928 | 10.980 | 9.466 | 13.448 | 10.036 | 9.225 |
| DAEP | 0.223 | 0.454 | 0.082 | 0.179 | 0.113 | 0.411 | 0.216 | 0.992 | 0.260 | 0.214 |
| PEEDA | 0.181 | 0.371 | 0.072 | 0.153 | 0.087 | 0.337 | 0.181 | 0.685 | 0.205 | 0.176 |
| DPE | 0.211 | 0.323 | 0.103 | 0.188 | 0.090 | 0.336 | 0.229 | 0.084 | 0.151 | 0.130 |
| AE-TAEA | 2.229 | 3.445 | 1.148 | 1.988 | 1.704 | 3.208 | 2.190 | 4.698 | 2.609 | 2.255 |
| 1-TEPA | 4.517 | 6.679 | 2.110 | 3.632 | 3.226 | 6.048 | 4.274 | 8.949 | 4.512 | 4.130 |
| AE-DAEP | 0.250 | 0.419 | 0.072 | 0.068 | 0.065 | 0.302 | 0.149 | 0.729 | 0.156 | 0.129 |
| AE-PEEDA | 0.091 | 0.113 | 0.055 | 0.000 | 0.051 | 0.055 | 0.000 | 0.083 | 0.027 | 0.026 |
| iAE-PEEDA | 0.000 | 0.000 | 0.000 | 0.000 | 0.000 | 0.000 | 0.000 | 0.000 | 0.000 | 0.000 |
| AE-DPE | 0.100 | 0.642 | 0.059 | 0.074 | 0.169 | 0.596 | 0.296 | 0.104 | 0.073 | 0.070 |
| BPEA | 0.316 | 0.649 | 0.081 | 0.221 | 0.152 | 0.558 | 0.257 | 0.781 | 0.053 | 0.056 |
| Others | 4.550 | 5.879 | 1.898 | 3.066 | 1.779 | 4.582 | 3.140 | 7.552 | 4.192 | 3.803 |
| MEA conversion, % | 49.40 | 65.33 | 32.69 | 45.43 | 40.15 | 61.44 | 47.63 | 81.50 | 50.64 | 47.61 |
| DETA conversion, % | 23.81 | 32.19 | 13.53 | 19.90 | 18.77 | 28.43 | 22.01 | 40.80 | 24.03 | 21.95 |
| Acyclic(N4), wt. % | 94.90 | 92.30 | 96.97 | 95.46 | 97.43 | 92.46 | 94.85 | 90.08 | 95.20 | 95.57 |
| Acyclic(N5), wt. % | 89.91 | 84.74 | 92.45 | 93.93 | 91.87 | 85.96 | 90.20 | 88.94 | 95.85 | 95.78 |
| Σ(N5)/Σ(N4), weight ratio | 0.62 | 0.80 | 0.42 | 0.52 | 0.48 | 0.75 | 0.59 | 0.86 | 0.58 | 0.57 |
| Acyclic(N4)/cyclic(<=N4), weight ratio | 5.98 | 4.28 | 8.23 | 6.09 | 8.76 | 4.10 | 5.56 | 3.11 | 5.65 | 5.60 |

TABLE V

| Example No. | 66 | 67 | 68 | 69 | 70 | 71 | 72 | 73 | 74 |
|---|---|---|---|---|---|---|---|---|---|
| Catalyst Type | E | E | E | E | E | E | E | E | E |
| Catalyst weight, gm | 73.5 | 73.5 | 73.5 | 73.5 | 73.5 | 73.5 | 73.5 | 73.5 | 73.5 |
| Pressure, psig | 600 | 600 | 600 | 600 | 600 | 600 | 600 | 600 | 600 |
| Temperature, °C. | 271.8 | 270 | 280.2 | 260.9 | 270.6 | 261.2 | 281.5 | 270 | 270 |
| Time on organics, hrs. | 5 | 8.5 | 25 | 30 | 34 | 49 | 55 | 76 | 78 |
| Duration of run, hrs. | 2 | 2 | 2 | 2 | 2 | 2 | 2 | 2 | 2 |
| MEA SV, gmol/hr/kgcat | 4.58 | 4.68 | 4.69 | 4.82 | 4.64 | 4.33 | 4.30 | 4.25 | 4.63 |
| DETA/MEA mole ratio | 1.00 | 1.00 | 1.00 | 1.00 | 1.00 | 1.00 | 1.00 | 1.00 | 1.00 |
| NH3/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 1.589 | 2.650 | 2.164 | 0.505 | 0.958 | 0.544 | 2.028 | 0.834 | 1.373 |
| MEA | 12.185 | 10.223 | 10.619 | 22.868 | 16.851 | 21.648 | 7.865 | 11.872 | 15.153 |
| PIP | 1.766 | 1.979 | 2.007 | 0.826 | 1.277 | 0.872 | 2.020 | 1.302 | 1.673 |
| DETA | 50.183 | 46.166 | 46.617 | 54.246 | 49.991 | 54.106 | 39.033 | 47.518 | 46.832 |
| AEEA | 0.119 | 0.000 | 0.000 | 0.956 | 0.608 | 1.198 | 0.102 | 0.526 | 0.540 |
| AEP | 2.179 | 2.940 | 2.249 | 0.787 | 1.410 | 0.884 | 2.331 | 1.655 | 1.577 |
| HEP | 0.000 | 0.000 | 0.000 | 0.000 | 0.000 | 0.000 | 0.000 | 0.000 | 0.000 |
| TAEA | 2.287 | 2.018 | 2.378 | 1.970 | 2.298 | 2.027 | 2.600 | 2.786 | 2.092 |

TABLE V-continued

|  |  |  |  |  |  |  |  |  |  |
|---|---|---|---|---|---|---|---|---|---|
| 1-TETA | 11.888 | 11.231 | 12.228 | 9.216 | 11.514 | 9.474 | 13.657 | 14.189 | 11.667 |
| DAEP | 0.650 | 1.480 | 0.908 | 0.125 | 0.263 | 0.142 | 1.136 | 0.460 | 0.271 |
| PEEDA | 0.395 | 0.990 | 0.562 | 0.087 | 0.186 | 0.092 | 0.793 | 0.320 | 0.185 |
| DPE | 0.000 | 0.079 | 0.082 | 0.000 | 0.000 | 0.000 | 0.063 | 0.000 | 0.000 |
| AE-TAEA | 2.483 | 2.485 | 2.951 | 1.171 | 2.213 | 1.284 | 3.723 | 3.229 | 2.178 |
| 1-TEPA | 5.189 | 5.996 | 6.225 | 2.266 | 4.333 | 2.454 | 8.413 | 6.752 | 4.536 |
| AE-DAEP | 0.456 | 1.010 | 0.453 | 0.000 | 0.214 | 0.000 | 0.650 | 0.175 | 0.435 |
| AE-PEEDA | 0.128 | 0.369 | 0.129 | 0.000 | 0.181 | 0.000 | 0.200 | 0.000 | 0.419 |
| iAE-PEEDA | 0.000 | 0.000 | 0.000 | 0.000 | 0.000 | 0.000 | 0.000 | 0.000 | 0.000 |
| AE-DPE | 0.131 | 0.143 | 0.206 | 0.000 | 0.132 | 0.000 | 0.735 | 0.194 | 0.412 |
| BPEA | 0.097 | 0.158 | 0.137 | 0.000 | 0.160 | 0.000 | 0.654 | 0.211 | 0.541 |
| Others | 0.955 | 2.634 | 1.884 | 0.416 | 0.810 | 0.314 | 3.399 | 0.747 | 2.735 |
| MEA conversion, % | 67.00 | 72.55 | 71.14 | 37.96 | 54.14 | 41.18 | 78.38 | 67.95 | 58.74 |
| DETA conversion, % | 19.21 | 26.33 | 24.71 | 12.54 | 19.15 | 12.63 | 36.23 | 23.77 | 24.21 |
| Acyclic(N4), wt. % | 93.14 | 83.87 | 90.40 | 98.14 | 96.85 | 98.00 | 89.08 | 95.60 | 96.79 |
| Acyclic(N5), wt. % | 90.43 | 83.47 | 90.84 | 100.00 | 90.50 | 100.00 | 84.43 | 94.51 | 78.79 |
| Σ(N5)/Σ(N4), weight ratio | 0.56 | 0.64 | 0.63 | 0.30 | 0.51 | 0.32 | 0.79 | 0.59 | 0.60 |
| Acyclic(N4)/cyclic(<=N4), weight ratio | 2.84 | 1.77 | 2.51 | 6.13 | 4.40 | 5.78 | 2.57 | 4.54 | 3.71 |

TABLE VI

| Example No. | 75 | 76 | 77 | 78 | 79 | 80 | 81 | 82 | 83 |
|---|---|---|---|---|---|---|---|---|---|
| Catalyst Type | F | F | F | F | F | F | F | F | F |
| Catalyst weight, gm | 76.8 | 76.8 | 76.8 | 76.8 | 76.8 | 76.8 | 76.8 | 76.8 | 76.8 |
| Pressure, psig | 600 | 600 | 600 | 600 | 600 | 600 | 600 | 600 | 600 |
| Temperature, °C. | 271.8 | 270 | 280.2 | 260.9 | 270.6 | 261.2 | 281.5 | 270 | 270 |
| Time on organics, hrs. | 5 | 8.5 | 25 | 30 | 34 | 49 | 55 | 76 | 78 |
| Duration of run, hrs. | 2 | 2 | 2 | 2 | 2 | 2 | 2 | 2 | 2 |
| MEA SV, gmol/hr/kgcat | 4.12 | 4.24 | 4.01 | 4.36 | 4.32 | 4.20 | 4.12 | 4.07 | 4.24 |
| DETA/MEA mole ratio | 1.00 | 1.00 | 1.00 | 1.00 | 1.00 | 1.00 | 1.00 | 1.00 | 1.00 |
| NH3/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 0.668 | 1.225 | 4.618 | 0.557 | 0.985 | 0.575 | 1.947 | 0.795 | 1.103 |
| MEA | 20.080 | 14.935 | 10.851 | 24.320 | 17.690 | 22.023 | 6.480 | 10.724 | 12.429 |
| PIP | 0.842 | 1.211 | 3.467 | 0.742 | 1.218 | 0.827 | 1.830 | 1.251 | 1.391 |
| DETA | 54.453 | 48.042 | 42.353 | 55.896 | 51.741 | 52.738 | 44.334 | 45.995 | 43.281 |
| AEEA | 0.451 | 0.313 | 0.139 | 1.169 | 0.760 | 1.449 | 0.113 | 0.560 | 0.651 |
| AEP | 0.974 | 1.563 | 4.537 | 0.688 | 1.325 | 0.757 | 2.402 | 1.604 | 1.454 |
| HEP | 0.000 | 0.000 | 0.000 | 0.000 | 0.000 | 0.000 | 0.000 | 0.000 | 0.000 |
| TAEA | 2.048 | 2.361 | 1.079 | 1.584 | 2.048 | 1.917 | 2.309 | 2.717 | 2.272 |
| 1-TETA | 10.507 | 12.537 | 9.182 | 8.077 | 10.742 | 9.822 | 13.034 | 15.283 | 13.463 |
| DAEP | 0.193 | 0.511 | 1.628 | 0.101 | 0.256 | 0.153 | 0.989 | 0.531 | 0.365 |
| PEEDA | 0.122 | 0.327 | 1.082 | 0.000 | 0.173 | 0.087 | 0.592 | 0.336 | 0.226 |
| DPE | 0.000 | 0.000 | 0.152 | 0.000 | 0.000 | 0.000 | 0.071 | 0.000 | 0.000 |
| AE-TAEA | 1.448 | 2.895 | 1.930 | 0.722 | 1.679 | 1.331 | 3.231 | 3.219 | 2.996 |
| 1-TEPA | 2.807 | 6.158 | 3.803 | 1.591 | 3.499 | 2.971 | 7.631 | 7.644 | 6.601 |
| AE-DAEP | 0.000 | 0.383 | 1.217 | 0.000 | 0.082 | 0.000 | 0.605 | 0.208 | 0.516 |
| AE-PEEDA | 0.000 | 0.091 | 0.346 | 0.000 | 0.000 | 0.000 | 0.174 | 0.000 | 0.418 |
| iAE-PEEDA | 0.000 | 0.000 | 0.000 | 0.000 | 0.000 | 0.000 | 0.000 | 0.000 | 0.000 |
| AE-DPE | 0.000 | 0.211 | 0.255 | 0.000 | 0.095 | 0.000 | 0.622 | 0.212 | 0.696 |
| BPEA | 0.000 | 0.119 | 0.152 | 0.000 | 0.089 | 0.000 | 0.573 | 0.168 | 0.136 |
| Others | 0.356 | 1.079 | 3.709 | 0.353 | 0.618 | 0.261 | 2.961 | 0.934 | 4.252 |
| MEA conversion, % | 45.60 | 59.89 | 70.22 | 33.93 | 51.41 | 40.05 | 82.26 | 70.97 | 66.33 |
| DETA conversion, % | 12.33 | 23.33 | 30.92 | 9.75 | 15.54 | 14.68 | 27.88 | 26.01 | 30.31 |
| Acyclic(N4), wt. % | 97.56 | 94.68 | 78.19 | 98.96 | 96.75 | 97.99 | 90.27 | 95.40 | 96.38 |
| Acyclic(N5), wt. % | 100.00 | 91.84 | 74.42 | 100.00 | 95.12 | 100.00 | 84.62 | 94.86 | 84.46 |
| Σ(N5)/Σ(N4), weight ratio | 0.33 | 0.63 | 0.59 | 0.24 | 0.41 | 0.36 | 0.76 | 0.61 | 0.70 |
| Acyclic(N4)/cyclic(<=N4), weight ratio | 5.89 | 4.12 | 0.94 | 6.31 | 4.30 | 6.43 | 2.61 | 4.84 | 4.58 |

TABLE VII

| Example No. | 84 | 85 | 86 | 87 | 88 | 89 | 90 | 91 |
|---|---|---|---|---|---|---|---|---|
| Catalyst Type | G | G | G | G | G | G | G | G |
| Catalyst weight, gm | 76.9 | 76.9 | 76.9 | 76.9 | 76.9 | 76.9 | 76.9 | 76.9 |
| Pressure, psig | 600 | 600 | 600 | 600 | 600 | 600 | 600 | 600 |
| Temperature, °C. | 274.4 | 274.4 | 280.9 | 259.8 | 270.6 | 259.9 | 281.6 | 270.4 |
| Time on organics, hrs. | 22 | 26 | 45.5 | 50.5 | 69 | 74.5 | 95 | 119 |
| Duration of run, hrs. | 2 | 2 | 2 | 2 | 2 | 2 | 2 | 1 |
| MEA SV, gmol/hr/kgcat | 3.43 | 3.31 | 2.85 | 3.38 | 3.41 | 3.28 | 3.10 | 3.37 |
| DETA/MEA mole ratio | 1.00 | 1.00 | 1.00 | 1.00 | 1.00 | 1.00 | 1.00 | 1.00 |
| NH3/MEA mole ratio | 5.97 | 5.97 | 5.97 | 5.97 | 5.97 | 5.97 | 5.97 | 5.97 |
| Crude product composition, wt. % | | | | | | | | |
| EDA | 1.637 | 1.752 | 6.215 | 1.030 | 1.705 | 0.900 | 2.931 | 2.193 |
| MEA | 11.346 | 11.171 | 3.117 | 18.167 | 8.987 | 15.534 | 1.812 | 8.349 |
| PIP | 0.000 | 1.648 | 4.753 | 1.076 | 1.772 | 1.117 | 2.704 | 1.830 |
| DETA | 46.167 | 45.574 | 31.042 | 48.855 | 44.146 | 47.263 | 56.512 | 40.724 |
| AEEA | 0.707 | 0.779 | 0.145 | 2.493 | 0.622 | 2.337 | 0.000 | 0.571 |

TABLE VII-continued

| | | | | | | | | |
|---|---|---|---|---|---|---|---|---|
| AEP | 1.861 | 1.810 | 7.515 | 1.125 | 2.031 | 1.205 | 4.394 | 2.315 |
| HEP | 0.000 | 0.000 | 0.000 | 0.000 | 0.000 | 0.000 | 0.000 | 0.000 |
| TAEA | 2.681 | 2.785 | 1.354 | 2.334 | 2.745 | 2.609 | 1.349 | 2.559 |
| 1-TETA | 14.827 | 14.769 | 9.178 | 13.329 | 15.519 | 14.514 | 14.115 | 14.634 |
| DAEP | 0.707 | 0.684 | 3.204 | 0.266 | 0.862 | 0.288 | 1.482 | 1.224 |
| PEEDA | 0.445 | 0.480 | 2.063 | 0.161 | 0.535 | 0.170 | 0.741 | 0.805 |
| DPE | 0.104 | 0.070 | 0.140 | 0.000 | 0.097 | 0.000 | 0.000 | 0.048 |
| AE-TAEA | 2.754 | 2.700 | 1.519 | 1.536 | 2.882 | 1.909 | 0.548 | 2.624 |
| 1-TEPA | 6.335 | 6.366 | 3.932 | 3.904 | 7.086 | 4.851 | 1.430 | 7.214 |
| AE-DAEP | 0.241 | 0.242 | 1.881 | 0.138 | 0.283 | 0.068 | 0.260 | 0.638 |
| AE-PEEDA | 0.079 | 0.075 | 0.401 | 0.000 | 0.087 | 0.000 | 0.000 | 0.188 |
| iAE-PEEDA | 0.000 | 0.000 | 0.000 | 0.000 | 0.000 | 0.000 | 0.000 | 0.000 |
| AE-DPE | 0.000 | 0.000 | 0.420 | 0.000 | 0.205 | 0.042 | 0.000 | 0.216 |
| BPEA | 0.223 | 0.231 | 0.079 | 0.000 | 0.239 | 0.045 | 0.000 | 0.261 |
| Others | 1.726 | 1.594 | 11.423 | 0.487 | 1.637 | 0.517 | 0.425 | 2.538 |
| MEA conversion, % | 69.01 | 69.88 | 91.52 | 51.10 | 75.61 | 57.80 | 94.97 | 76.78 |
| DETA conversion, % | 25.06 | 26.98 | 49.81 | 21.84 | 28.79 | 23.70 | 6.73 | 32.70 |
| Acyclic(N4), wt. % | 93.31 | 93.43 | 66.08 | 97.35 | 92.43 | 97.40 | 87.43 | 89.22 |
| Acyclic(N5), wt. % | 94.36 | 94.30 | 66.22 | 97.52 | 92.46 | 97.75 | 88.40 | 88.31 |
| Σ(N5)/Σ(N4), weight ratio | 0.51 | 0.51 | 0.52 | 0.35 | 0.55 | 0.39 | 0.13 | 0.58 |
| Acyclic(N4)/cyclic(<=N4), weight ratio | 5.62 | 3.74 | 0.60 | 5.96 | 3.45 | 6.16 | 1.66 | 2.76 |

TABLE VIII

| Example No. | 92 | 93 | 94 | 95 | 96 | 97 | 98 |
|---|---|---|---|---|---|---|---|
| Catalyst Type | H | H | H | H | H | H | H |
| Catalyst weight, gm | 79.56 | 79.56 | 79.56 | 79.56 | 79.56 | 79.56 | 79.56 |
| Pressure, psig | 602 | 602 | 603 | 602 | 602 | 603 | 603 |
| Temperature, °C. | 268.2 | 270 | 280 | 258 | 270 | 279.6 | 269.3 |
| Time on organics, hrs. | 24 | 4.5 | 29 | 48 | 72 | 77 | 96.25 |
| Duration of run, hrs. | 2 | 2 | 2 | 2 | 2 | 2 | 2 |
| MEA SV, gmol/hr/kgcat | 1.40 | 2.14 | 0.94 | 0.90 | 2.37 | 1.20 | 0.78 |
| DETA/MEA mole ratio | 1.00 | 1.00 | 1.00 | 1.00 | 1.00 | 1.00 | 1.00 |
| NH3/MEA mole ratio | 5.97 | 5.97 | 5.97 | 5.97 | 5.97 | 5.97 | 5.97 |
| Crude product composition, wt. % | | | | | | | |
| EDA | 1.357 | 2.006 | 4.277 | 2.306 | 1.090 | 3.199 | 2.846 |
| MEA | 3.284 | 1.883 | 0.923 | 5.261 | 9.399 | 1.511 | 0.959 |
| PIP | 1.251 | 1.346 | 2.162 | 1.382 | 0.869 | 1.861 | 1.707 |
| DETA | 35.076 | 34.162 | 23.951 | 32.591 | 36.463 | 29.869 | 26.799 |
| AEEA | 0.000 | 0.000 | 0.254 | 1.603 | 1.807 | 0.455 | 0.394 |
| AEP | 2.193 | 2.794 | 3.951 | 1.914 | 1.135 | 3.122 | 2.893 |
| HEP | 0.000 | 0.000 | 0.000 | 0.000 | 0.000 | 0.000 | 0.000 |
| TAEA | 2.772 | 3.324 | 1.853 | 2.782 | 2.789 | 2.443 | 2.434 |
| 1-TETA | 17.464 | 21.229 | 13.658 | 16.596 | 14.933 | 15.761 | 14.689 |
| DAEP | 1.240 | 1.560 | 2.447 | 0.995 | 0.521 | 1.740 | 1.700 |
| PEEDA | 0.891 | 1.074 | 0.289 | 0.699 | 0.388 | 0.125 | 0.247 |
| DPE | 0.000 | 0.000 | 0.355 | 0.262 | 0.143 | 0.157 | 0.291 |
| AE-TAEA | 4.199 | 5.092 | 0.220 | 4.454 | 4.587 | 4.487 | 4.743 |
| 1-TEPA | 9.456 | 11.417 | 10.338 | 9.746 | 8.931 | 11.169 | 10.912 |
| AE-DAEP | 0.765 | 0.809 | 0.324 | 0.167 | 0.134 | 0.189 | 0.259 |
| AE-PEEDA | 0.060 | 0.064 | 0.193 | 0.141 | 0.097 | 0.112 | 0.175 |
| iAE-PEEDA | 0.278 | 0.000 | 0.000 | 0.000 | 0.000 | 0.000 | 0.000 |
| AE-DPE | 0.000 | 0.242 | 0.496 | 0.187 | 0.158 | 0.174 | 0.433 |
| BPEA | 0.000 | 0.000 | 0.734 | 0.667 | 0.692 | 0.754 | 0.232 |
| Others | 6.124 | 6.280 | 20.326 | 8.645 | 7.394 | 10.911 | 15.928 |
| MEA conversion, % | 90.76 | 95.12 | 97.45 | 85.78 | 74.59 | 95.86 | 97.37 |
| DETA conversion, % | 41.33 | 47.41 | 60.62 | 47.66 | 41.42 | 51.33 | 56.29 |
| Acyclic(N4), wt. % | 90.47 | 90.31 | 83.39 | 90.83 | 94.39 | 90.00 | 88.44 |
| Acyclic(N5), wt. % | 92.53 | 93.67 | 85.81 | 92.43 | 92.59 | 92.72 | 93.44 |
| Σ(N5)/Σ(N4), weight ratio | 0.66 | 0.65 | 0.66 | 0.72 | 0.78 | 0.83 | 0.87 |
| Acyclic(N4)/cyclic(<=N4), weight ratio | 3.63 | 3.62 | 1.69 | 3.69 | 5.80 | 2.60 | 2.50 |

TABLE IX

| | Example No. | | | | | | | |
|---|---|---|---|---|---|---|---|---|
| | 99 | 100 | 101 | 102 | 103 | 104 | 105 | 106 |
| Catalyst Type | I | I | I | I | I | I | I | I |
| Catalyst weight, gm | 78.44 | 78.44 | 78.44 | 78.44 | 78.44 | 78.44 | 78.44 | 78.44 |
| Pressure, psig | 598 | 598 | 598 | 598 | 598 | 598 | 598 | 598 |
| Temperature, °C. | 268.2 | 270 | 280 | 258 | 268 | 270 | 279.6 | 269.3 |
| Time on organics, hrs. | 24 | 4 | 29 | 48 | 53 | 72 | 77 | 96.25 |
| Duration of run, hrs. | 2 | 2 | 2 | 2 | 2 | 2 | 2 | 2 |
| MEA SV, gmol/hr/kgcat | 2.38 | 3.12 | 3.09 | 3.01 | 3.06 | 2.97 | 2.39 | 3.07 |
| DETA/MEA mole ratio | 1.00 | 1.00 | 1.00 | 1.00 | 1.00 | 1.00 | 1.00 | 1.00 |
| NH3/MEA mole ratio | 5.97 | 5.97 | 5.97 | 5.97 | 5.97 | 5.97 | 5.97 | 5.97 |
| Crude product composition, wt. % | | | | | | | | |
| EDA | 1.113 | 0.976 | 1.860 | 0.782 | 1.043 | 1.302 | 1.824 | 0.980 |

TABLE IX-continued

| | Example No. | | | | | | | |
|---|---|---|---|---|---|---|---|---|
| | 99 | 100 | 101 | 102 | 103 | 104 | 105 | 106 |
| MEA | 10.615 | 12.327 | 5.220 | 14.139 | 10.320 | 9.098 | 6.092 | 8.653 |
| PIP | 1.129 | 1.005 | 1.496 | 0.859 | 1.132 | 1.320 | 1.611 | 1.111 |
| DETA | 36.799 | 37.931 | 31.746 | 39.773 | 37.334 | 36.528 | 34.990 | 34.182 |
| AEEA | 1.033 | 1.258 | 0.344 | 1.844 | 1.311 | 1.136 | 0.541 | 1.124 |
| AEP | 1.305 | 1.132 | 2.067 | 0.979 | 1.353 | 1.472 | 2.104 | 1.379 |
| HEP | 0.000 | 0.000 | 0.000 | 0.000 | 0.000 | 0.000 | 0.000 | 0.000 |
| TAEA | 2.615 | 2.470 | 2.365 | 2.433 | 2.657 | 2.733 | 2.577 | 2.612 |
| 1-TETA | 14.292 | 13.515 | 14.587 | 14.440 | 14.597 | 14.582 | 14.930 | 13.465 |
| DAEP | 0.594 | 0.489 | 1.269 | 0.296 | 0.595 | 0.603 | 1.041 | 0.647 |
| PEEDA | 0.435 | 0.400 | 0.866 | 0.242 | 0.463 | 0.496 | 0.064 | 0.168 |
| DPE | 0.131 | 0.135 | 0.159 | 0.052 | 0.133 | 0.092 | 0.091 | 0.150 |
| AE-TAEA | 3.929 | 3.799 | 4.211 | 3.918 | 4.621 | 4.393 | 4.377 | 4.357 |
| 1-TEPA | 8.291 | 7.823 | 9.865 | 6.776 | 8.516 | 8.862 | 9.611 | 8.767 |
| AE-DAEP | 0.503 | 0.527 | 1.032 | 0.400 | 0.502 | 0.089 | 0.121 | 0.177 |
| AE-PEEDA | 0.099 | 0.115 | 0.175 | 0.082 | 0.088 | 0.060 | 0.083 | 0.122 |
| iAE-PEEDA | 0.000 | 0.000 | 0.000 | 0.000 | 0.000 | 0.000 | 0.000 | 0.000 |
| AE-DPE | 0.163 | 0.228 | 0.356 | 0.253 | 0.153 | 0.000 | 0.117 | 0.297 |
| BPEA | 0.610 | 0.599 | 0.845 | 0.412 | 0.618 | 0.748 | 0.798 | 0.729 |
| Others | 7.223 | 7.030 | 12.137 | 4.048 | 6.784 | 6.715 | 8.479 | 10.461 |
| MEA conversion, % | 71.04 | 66.53 | 86.00 | 61.31 | 72.29 | 75.11 | 83.32 | 76.14 |
| DETA conversion, % | 40.33 | 38.80 | 49.40 | 35.32 | 40.42 | 40.60 | 43.06 | 43.99 |
| Acyclic(N4), wt. % | 93.58 | 93.98 | 88.08 | 96.62 | 93.54 | 93.56 | 93.61 | 94.34 |
| Acyclic(N5), wt. % | 89.89 | 88.77 | 85.39 | 90.32 | 90.62 | 93.07 | 92.60 | 90.83 |
| Σ(N5)/Σ(N4), weight ratio | 0.75 | 0.77 | 0.86 | 0.68 | 0.79 | 0.77 | 0.81 | 0.85 |
| Acyclic(N4)/cyclic(< = N4), weight ratio | 4.70 | 5.06 | 2.89 | 6.95 | 4.69 | 4.35 | 3.57 | 4.66 |

TABLE X

| | Example No. | | | | | | | | |
|---|---|---|---|---|---|---|---|---|---|
| | 107 | 108 | 109 | 110 | 111 | 112 | 113 | 114 | 115 |
| Catalyst Type | J | J | J | J | J | J | J | J | J |
| Catalyst weight, gm | 73.3 | 73.3 | 73.3 | 73.3 | 73.3 | 73.3 | 73.3 | 73.3 | 73.3 |
| Pressure, psig | 598 | 603 | 603 | 605 | 604 | 604.9 | 604 | 604 | 604 |
| Temperature, °C. | 274.8 | 274.2 | 280.3 | 261.2 | 271.4 | 261.8 | 180.2 | 269.7 | 269.6 |
| Time on organics, hrs. | 6 | 8 | 26 | 33 | 50 | 54.5 | 74 | 98.5 | 100 |
| Duration of run, hrs. | 2 | 2 | 2 | 2 | 2 | 2 | 2 | 1.5 | 1.5 |
| MEA SV, gmol/hr/kgcat | 4.27 | 4.14 | 3.79 | 3.77 | 3.97 | 3.92 | 3.80 | 4.20 | 4.17 |
| DETA/MEA mole ratio | 1.00 | 1.00 | 1.00 | 1.00 | 1.00 | 1.00 | 1.00 | 1.00 | 1.00 |
| NH$_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 1.429 | 1.424 | 3.172 | 0.868 | 1.570 | 0.800 | 3.025 | 0.882 | 1.051 |
| MEA | 14.429 | 13.943 | 9.322 | 21.725 | 13.285 | 20.998 | 6.949 | 13.400 | 14.889 |
| PIP | 1.355 | 1.300 | 2.261 | 0.868 | 1.478 | 0.814 | 2.234 | 1.030 | 1.176 |
| DETA | 47.230 | 42.295 | 39.568 | 53.087 | 43.212 | 52.672 | 42.607 | 43.225 | 47.069 |
| AEEA | 0.550 | 0.512 | 0.197 | 1.245 | 0.599 | 1.274 | 0.098 | 0.676 | 0.823 |
| AEP | 1.672 | 1.513 | 2.379 | 0.784 | 1.629 | 0.825 | 2.731 | 1.328 | 1.396 |
| HEP | 0.000 | 0.000 | 0.000 | 0.000 | 0.000 | 0.000 | 0.000 | 0.000 | 0.000 |
| TAEA | 2.605 | 2.279 | 2.424 | 2.158 | 2.317 | 2.279 | 2.342 | 2.467 | 2.739 |
| 1-TETA | 13.001 | 12.670 | 12.814 | 9.683 | 12.889 | 10.389 | 12.621 | 13.828 | 13.069 |
| DAEP | 0.431 | 0.360 | 0.995 | 0.154 | 0.368 | 0.187 | 1.128 | 0.319 | 0.360 |
| PEEDA | 0.302 | 0.232 | 0.710 | 0.092 | 0.242 | 0.106 | 0.753 | 0.216 | 0.238 |
| DPE | 0.000 | 0.000 | 0.075 | 0.000 | 0.000 | 0.000 | 0.089 | 0.000 | 0.000 |
| AE-TAEA | 2.986 | 2.963 | 3.398 | 1.553 | 2.893 | 1.804 | 3.351 | 3.239 | 3.092 |
| 1-TEPA | 5.571 | 5.909 | 7.347 | 2.674 | 5.827 | 3.180 | 7.449 | 6.276 | 6.252 |
| AE-DAEP | 0.181 | 0.442 | 0.599 | 0.000 | 0.449 | 0.000 | 0.673 | 0.454 | 0.145 |
| AE-PEEDA | 0.000 | 0.529 | 0.187 | 0.000 | 0.476 | 0.000 | 0.202 | 0.384 | 0.000 |
| iAE-PEEDA | 0.000 | 0.000 | 0.000 | 0.000 | 0.000 | 0.000 | 0.000 | 0.000 | 0.000 |
| AE-DPE | 0.352 | 0.757 | 0.645 | 0.089 | 0.811 | 0.084 | 0.585 | 0.601 | 0.363 |
| BPEA | 0.223 | 0.550 | 0.560 | 0.093 | 0.574 | 0.076 | 0.109 | 0.674 | 0.300 |
| Others | 1.202 | 3.012 | 3.419 | 0.547 | 3.170 | 0.521 | 3.655 | 3.060 | 1.300 |
| MEA conversion, % | 61.11 | 61.45 | 74.39 | 42.37 | 63.75 | 43.71 | 81.09 | 63.56 | 60.17 |
| DETA conversion, % | 24.34 | 30.49 | 35.40 | 14.85 | 29.93 | 16.08 | 31.11 | 30.14 | 25.17 |
| Acyclic(N4), wt. % | 95.51 | 96.19 | 89.54 | 97.97 | 96.15 | 97.74 | 88.37 | 96.82 | 96.36 |
| Acyclic(N5), wt. % | 91.88 | 79.57 | 84.37 | 95.88 | 79.06 | 96.89 | 87.32 | 81.83 | 92.04 |
| Σ(N5)/Σ(N4), weight ratio | 0.57 | 0.72 | 0.75 | 0.36 | 0.70 | 0.40 | 0.73 | 0.69 | 0.62 |
| Acyclic(N4)/cyclic(< = N4), weight ratio | 4.15 | 4.39 | 2.37 | 6.24 | 4.09 | 6.56 | 2.16 | 5.63 | 4.99 |

TABLE XI

| | Example No. | | | | | | | | |
|---|---|---|---|---|---|---|---|---|---|
| | 116 | 117 | 118 | 119 | 120 | 121 | 122 | 123 | 124 |
| Catalyst Type | K | K | K | K | K | K | K | K | K |
| Catalyst weight, gm | 78.4 | 78.4 | 78.4 | 78.4 | 78.4 | 78.4 | 78.4 | 78.4 | 78.4 |
| Pressure, psig | 600 | 600 | 600 | 600 | 600 | 600 | 600 | 600 | 600 |

TABLE XI-continued

| | Example No. | | | | | | | | |
|---|---|---|---|---|---|---|---|---|---|
| | 116 | 117 | 118 | 119 | 120 | 121 | 122 | 123 | 124 |
| Temperature, °C. | 269.3 | 269.2 | 279.4 | 258.8 | 269.2 | 259.4 | 279.2 | 268.9 | 269.6 |
| Time on organics, hrs. | 23.5 | 27.5 | 47 | 52 | 71 | 76 | 95 | 100 | 120 |
| Duration of run, hrs. | 2 | 2 | 2 | 2 | 2 | 2 | 2 | 2 | 2 |
| MEA SV, gmol/hr/kgcat | 3.21 | 3.22 | 3.15 | 3.26 | 3.16 | 3.28 | 2.60 | 3.20 | 2.85 |
| DETA/MEA mole ratio | 1.00 | 1.00 | 1.00 | 1.00 | 1.00 | 1.00 | 1.00 | 1.00 | 1.00 |
| $NH_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 2.011 | 1.726 | 3.400 | 1.045 | 1.704 | 2.927 | 2.694 | 1.875 | 2.016 |
| MEA | 19.645 | 19.830 | 10.922 | 24.936 | 17.747 | 13.549 | 6.399 | 19.549 | 17.740 |
| PIP | 1.597 | 1.489 | 2.412 | 0.797 | 1.531 | 2.082 | 2.206 | 1.710 | 1.570 |
| DETA | 49.999 | 49.815 | 44.929 | 54.559 | 49.660 | 43.523 | 37.413 | 49.063 | 49.599 |
| AEEA | 0.269 | 0.305 | 0.156 | 0.448 | 0.288 | 0.213 | 0.000 | 0.288 | 0.481 |
| AEP | 1.525 | 1.493 | 2.688 | 0.754 | 1.573 | 3.273 | 2.897 | 1.565 | 1.777 |
| HEP | 0.000 | 0.000 | 0.000 | 0.000 | 0.000 | 0.000 | 0.000 | 0.000 | 0.000 |
| TAEA | 2.104 | 2.144 | 2.134 | 1.661 | 2.231 | 4.370 | 1.861 | 2.034 | 2.061 |
| 1-TETA | 9.952 | 10.859 | 11.222 | 7.684 | 10.454 | 11.481 | 11.542 | 9.840 | 10.021 |
| DAEP | 0.081 | 0.238 | 1.038 | 0.095 | 0.470 | 1.096 | 1.664 | 0.680 | 0.442 |
| PEEDA | 0.215 | 0.153 | 0.603 | 0.062 | 0.241 | 0.388 | 1.166 | 0.368 | 0.000 |
| DPE | 0.000 | 0.000 | 0.051 | 0.000 | 0.000 | 0.000 | 0.000 | 0.000 | 0.000 |
| AE-TAEA | 0.000 | 0.000 | 0.000 | 0.000 | 0.000 | 4.286 | 4.233 | 0.000 | 1.883 |
| 1-TEPA | 1.592 | 1.629 | 2.342 | 0.742 | 1.760 | 4.935 | 8.341 | 1.975 | 2.969 |
| AE-DAEP | 0.000 | 0.168 | 0.443 | 0.077 | 0.178 | 0.160 | 1.448 | 0.296 | 0.000 |
| AE-PEEDA | 0.160 | 0.000 | 0.095 | 0.000 | 0.069 | 0.000 | 0.614 | 0.000 | 0.000 |
| iAE-PEEDA | 0.000 | 0.000 | 0.000 | 0.000 | 0.000 | 0.000 | 0.000 | 0.000 | 0.000 |
| AE-DPE | 0.066 | 0.073 | 0.204 | 0.051 | 0.268 | 0.089 | 0.503 | 0.000 | 0.000 |
| BPEA | 0.000 | 0.000 | 0.076 | 0.000 | 0.000 | 0.000 | 0.496 | 0.000 | 0.000 |
| Others | 3.564 | 3.489 | 6.276 | 2.170 | 3.688 | 1.449 | 6.241 | 2.737 | 0.000 |
| MEA conversion, % | 45.57 | 45.47 | 69.23 | 31.62 | 50.63 | 63.79 | 82.59 | 45.48 | 49.85 |
| DETA conversion, % | 17.68 | 18.59 | 24.77 | 11.08 | 17.90 | 30.86 | 39.50 | 18.68 | 16.68 |
| Acyclic(N4), wt. % | 97.60 | 97.08 | 88.75 | 98.34 | 94.69 | 91.44 | 82.57 | 91.89 | 96.47 |
| Acyclic(N5), wt. % | 87.57 | 87.12 | 74.10 | 85.31 | 77.39 | 97.37 | 80.42 | 86.95 | 100.00 |
| $\Sigma(N5)/\Sigma(N4)$, weight ratio | 0.15 | 0.14 | 0.21 | 0.09 | 0.17 | 0.55 | 0.96 | 0.18 | 0.39 |
| Acyclic(N4)/cyclic($\leq$ N4), weight ratio | 3.53 | 3.86 | 1.97 | 5.47 | 3.33 | 2.32 | 1.69 | 2.75 | 3.19 |

TABLE XII

| | Example No. | | | | | | | | |
|---|---|---|---|---|---|---|---|---|---|
| | 125 | 126 | 127 | 128 | 129 | 130 | 131 | 132 | 133 |
| Catalyst Type | L | L | L | L | L | L | L | L | L |
| Catalyst weight, gm | 73.2 | 73.2 | 73.2 | 73.2 | 73.2 | 73.2 | 73.2 | 73.2 | 73.2 |
| Pressure, psig | 600 | 600 | 600 | 600 | 600 | 600 | 600 | 600 | 600 |
| Temperature, °C. | 270.1 | 270 | 280.2 | 259.7 | 270.1 | 259.6 | 280 | 270 | 270 |
| Time on organics, hrs. | 5 | 7.5 | 26.5 | 31.5 | 49.75 | 54 | 74 | 77.5 | 80 |
| Duration of run, hrs. | 2 | 2 | 2 | 2 | 2 | 2 | 2 | 2 | 2 |
| MEA SV, gmol/hr/kgcat | 4.58 | 4.67 | 4.05 | 4.77 | 4.61 | 4.82 | 4.51 | 4.47 | 4.60 |
| DETA/MEA mole ratio | 1.00 | 1.00 | 1.00 | 1.00 | 1.00 | 1.00 | 1.00 | 1.00 | 1.00 |
| $NH_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 0.979 | 1.000 | 2.216 | 0.524 | 0.877 | 0.472 | 2.124 | 1.229 | 1.025 |
| MEA | 17.990 | 19.335 | 10.087 | 24.701 | 17.662 | 24.119 | 9.596 | 17.400 | 17.389 |
| PIP | 0.989 | 0.964 | 1.718 | 0.593 | 0.993 | 0.590 | 1.696 | 1.203 | 1.145 |
| DETA | 50.172 | 53.162 | 45.219 | 55.645 | 50.697 | 55.944 | 45.259 | 49.313 | 51.748 |
| AEEA | 0.000 | 0.433 | 0.000 | 1.012 | 0.642 | 1.026 | 0.126 | 0.667 | 0.713 |
| AEP | 1.134 | 1.062 | 2.216 | 0.613 | 1.091 | 0.648 | 2.172 | 1.229 | 1.334 |
| HEP | 0.000 | 0.000 | 0.000 | 0.000 | 0.000 | 0.000 | 0.000 | 0.000 | 0.000 |
| TAEA | 2.208 | 2.198 | 2.406 | 1.617 | 2.175 | 1.619 | 2.323 | 2.162 | 2.307 |
| 1-TETA | 9.955 | 10.785 | 12.776 | 7.737 | 10.803 | 7.844 | 12.734 | 10.465 | 11.340 |
| DAEP | 0.232 | 0.218 | 0.936 | 0.103 | 0.249 | 0.110 | 0.896 | 0.273 | 0.300 |
| PEEDA | 0.124 | 0.143 | 0.603 | 0.062 | 0.166 | 0.000 | 0.576 | 0.174 | 0.184 |
| DPE | 0.000 | 0.075 | 0.075 | 0.000 | 0.000 | 0.000 | 0.085 | 0.000 | 0.000 |
| AE-TAEA | 1.588 | 1.180 | 3.177 | 0.735 | 2.054 | 0.826 | 3.277 | 1.942 | 2.255 |
| 1-TEPA | 2.656 | 2.775 | 6.758 | 1.190 | 3.841 | 1.534 | 6.807 | 4.191 | 4.651 |
| AE-DAEP | 0.114 | 0.097 | 0.606 | 0.000 | 0.000 | 0.000 | 0.525 | 0.086 | 0.106 |
| AE-PEEDA | 0.000 | 0.000 | 0.149 | 0.000 | 0.000 | 0.000 | 0.136 | 0.000 | 0.000 |
| iAE-PEEDA | 0.000 | 0.000 | 0.000 | 0.000 | 0.000 | 0.000 | 0.000 | 0.000 | 0.000 |
| AE-DPE | 0.000 | 0.000 | 0.235 | 0.000 | 0.000 | 0.000 | 0.222 | 0.121 | 0.135 |
| BPEA | 0.000 | 0.000 | 0.112 | 0.000 | 0.000 | 0.000 | 0.109 | 0.100 | 0.128 |
| Others | 6.460 | 0.646 | 1.993 | 0.269 | 0.439 | 0.218 | 1.489 | 0.694 | 0.701 |
| MEA conversion, % | 52.45 | 47.17 | 72.49 | 32.06 | 50.75 | 33.87 | 73.52 | 51.33 | 53.62 |
| DETA conversion, % | 19.53 | 13.67 | 26.69 | 9.04 | 15.98 | 8.83 | 25.77 | 18.02 | 17.97 |
| Acyclic(N4), wt. % | 97.15 | 97.30 | 90.39 | 98.27 | 96.90 | 98.85 | 90.62 | 96.58 | 96.57 |
| Acyclic(N5), wt. % | 97.38 | 97.61 | 90.01 | 100.00 | 100.00 | 100.00 | 91.03 | 95.24 | 94.93 |
| $\Sigma(N5)/\Sigma(N4)$, weight ratio | 0.35 | 0.30 | 0.66 | 0.20 | 0.44 | 0.25 | 0.67 | 0.49 | 0.51 |
| Acyclic(N4)/cyclic($\leq$ N4), weight ratio | 4.91 | 5.44 | 2.74 | 6.83 | 5.19 | 7.02 | 2.78 | 4.39 | 4.61 |

TABLE XIII

| | Example No. | | | | | | | | |
|---|---|---|---|---|---|---|---|---|---|
| | 134 | 135 | 136 | 137 | 138 | 139 | 140 | 141 | 142 |
| Catalyst Type | M | M | M | M | M | M | M | M | M |
| Catalyst weight, gm | 76.6 | 76.6 | 76.6 | 76.6 | 76.6 | 76.6 | 76.6 | 76.6 | 76.6 |
| Pressure, psig | 597 | 599 | 594 | 596 | 597 | 598 | 598 | 578 | 592 |
| Temperature, °C. | 274.8 | 274.2 | 280.3 | 261.2 | 271.4 | 261.8 | 280.2 | 269.7 | 269.6 |
| Time on organics, hrs. | 6 | 8 | 26 | 33 | 50 | 54.5 | 74 | 98.5 | 100 |
| Duration of run, hrs. | 2 | 2 | 2 | 2 | 2 | 2 | 2 | 1.5 | 1.5 |
| MEA SV, gmol/hr/kgcat | 3.47 | 3.41 | 3.15 | 3.08 | 3.28 | 3.12 | 3.05 | 3.41 | 3.47 |
| DETA/MEA mole ratio | 1.00 | 1.00 | 1.00 | 1.00 | 1.00 | 1.00 | 1.00 | 1.00 | 1.00 |
| $NH_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 2.061 | 2.011 | 3.148 | 1.184 | 2.307 | 1.307 | 3.298 | 4.426 | 1.702 |
| MEA | 11.521 | 11.310 | 6.396 | 20.282 | 13.265 | 20.615 | 5.659 | 11.296 | 14.677 |
| PIP | 1.527 | 1.470 | 2.157 | 0.932 | 1.702 | 0.989 | 2.146 | 3.452 | 1.419 |
| DETA | 42.334 | 40.741 | 38.310 | 49.435 | 42.179 | 50.484 | 37.713 | 34.699 | 46.940 |
| AEEA | 0.171 | 0.229 | 0.345 | 1.161 | 0.498 | 1.159 | 0.000 | 0.094 | 0.619 |
| AEP | 2.239 | 2.094 | 3.230 | 0.922 | 1.874 | 0.956 | 3.141 | 5.456 | 1.744 |
| HEP | 0.000 | 0.000 | 0.000 | 0.000 | 0.000 | 0.000 | 0.000 | 0.000 | 0.000 |
| TAEA | 2.485 | 2.769 | 2.228 | 2.289 | 2.411 | 2.243 | 1.952 | 1.031 | 2.473 |
| 1-TETA | 13.469 | 14.759 | 13.494 | 11.956 | 12.180 | 10.324 | 11.730 | 8.626 | 13.276 |
| DAEP | 0.942 | 0.959 | 1.643 | 0.249 | 0.703 | 0.219 | 1.537 | 2.523 | 0.455 |
| PEEDA | 0.758 | 0.783 | 1.241 | 0.150 | 0.500 | 0.132 | 1.082 | 1.975 | 0.332 |
| DPE | 0.099 | 0.097 | 0.135 | 0.000 | 0.076 | 0.000 | 0.130 | 0.128 | 0.000 |
| AE-TAEA | 3.476 | 3.863 | 3.743 | 2.042 | 3.220 | 1.844 | 3.286 | 1.977 | 3.025 |
| 1-TEPA | 6.876 | 7.762 | 8.263 | 3.497 | 6.138 | 3.258 | 7.403 | 4.058 | 5.508 |
| AE-DAEP | 0.571 | 0.509 | 1.049 | 0.000 | 0.355 | 0.000 | 1.086 | 2.356 | 0.367 |
| AE-PEEDA | 0.150 | 0.159 | 0.419 | 0.000 | 0.107 | 0.000 | 0.878 | 0.928 | 0.121 |
| iAE-PEEDA | 0.000 | 0.000 | 0.000 | 0.000 | 0.000 | 0.000 | 0.000 | 0.000 | 0.000 |
| AE-DPE | 0.410 | 0.460 | 0.567 | 0.176 | 0.433 | 0.123 | 0.974 | 0.089 | 0.242 |
| BPEA | 0.370 | 0.402 | 0.445 | 0.148 | 0.335 | 0.123 | 0.797 | 0.129 | 0.142 |
| Others | 3.222 | 3.202 | 4.458 | 0.022 | 2.377 | 0.934 | 5.999 | 8.878 | 1.378 |
| MEA conversion, % | 69.06 | 69.99 | 82.87 | 44.85 | 63.31 | 44.03 | 84.47 | 69.87 | 60.81 |
| DETA conversion, % | 32.44 | 35.75 | 39.01 | 20.11 | 30.67 | 18.54 | 38.47 | 45.00 | 25.51 |
| Acyclic(N4), wt. % | 89.87 | 90.50 | 83.90 | 97.28 | 91.94 | 97.28 | 83.27 | 67.62 | 95.24 |
| Acyclic(N5), wt. % | 87.34 | 88.37 | 82.89 | 94.47 | 88.39 | 95.40 | 74.10 | 63.28 | 90.73 |
| $\Sigma(N5)/\Sigma(N4)$, weight ratio | 0.67 | 0.68 | 0.77 | 0.40 | 0.67 | 0.41 | 0.88 | 0.67 | 0.57 |
| Acyclic(N4)/cyclic($<$ = N4), weight ratio | 2.87 | 3.24 | 1.87 | 6.32 | 3.01 | 5.47 | 1.70 | 0.71 | 3.99 |

TABLE XIV

| | Example No. | | | | | | | | |
|---|---|---|---|---|---|---|---|---|---|
| | 143 | 144 | 145 | 146 | 147 | 148 | 149 | 150 | 151 |
| Catalyst Type | N | N | N | N | N | N | N | N | N |
| Catalyst weight, gm | 77.2 | 77.2 | 77.2 | 77.2 | 77.2 | 77.2 | 77.2 | 77.2 | 77.2 |
| Pressure, psig | 606 | 602 | 603 | 599 | 605 | 601.3 | 604 | 605 | 602 |
| Temperature, °C. | 274.8 | 274.2 | 280.3 | 261.2 | 271.4 | 261.8 | 280.2 | 269.7 | 269.6 |
| Time on organics, hrs. | 6 | 8 | 26 | 33 | 50 | 54.5 | 74 | 98.5 | 100 |
| Duration of run, hrs. | 2 | 2 | 2 | 2 | 2 | 2 | 2 | 1.5 | 1.5 |
| MEA SV, gmol/hr/kgcat | 3.66 | 3.28 | 3.32 | 3.12 | 3.38 | 3.23 | 3.28 | 3.68 | 3.71 |
| DETA/MEA mole ratio | 1.00 | 1.00 | 1.00 | 1.00 | 1.00 | 1.00 | 1.00 | 1.00 | 1.00 |
| $NH_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 4.605 | 3.886 | 5.431 | 1.582 | 3.133 | 1.518 | 5.888 | 2.090 | 2.159 |
| MEA | 14.165 | 13.840 | 8.988 | 20.796 | 15.163 | 22.247 | 9.341 | 16.165 | 15.935 |
| PIP | 2.743 | 2.486 | 3.003 | 1.044 | 1.960 | 1.001 | 3.051 | 1.333 | 1.433 |
| DETA | 39.645 | 39.381 | 34.406 | 46.873 | 40.571 | 50.785 | 37.693 | 42.241 | 45.956 |
| AEEA | 0.101 | 0.264 | 0.101 | 0.891 | 0.476 | 0.962 | 0.000 | 0.631 | 0.594 |
| AEP | 3.421 | 3.180 | 4.196 | 1.218 | 2.294 | 1.114 | 3.834 | 1.851 | 1.880 |
| HEP | 0.000 | 0.000 | 0.000 | 0.000 | 0.000 | 0.000 | 0.000 | 0.000 | 0.000 |
| TAEA | 1.671 | 1.753 | 1.198 | 1.910 | 2.183 | 2.023 | 1.193 | 2.292 | 2.459 |
| 1-TETA | 10.517 | 11.090 | 10.855 | 9.315 | 11.704 | 9.626 | 10.401 | 11.963 | 12.528 |
| DAEP | 1.223 | 1.224 | 1.875 | 0.287 | 0.898 | 0.251 | 1.503 | 0.631 | 0.765 |
| PEEDA | 1.151 | 1.136 | 1.743 | 0.206 | 0.759 | 0.177 | 1.167 | 0.451 | 0.617 |
| DPE | 0.130 | 0.119 | 0.213 | 0.000 | 0.080 | 0.000 | 0.109 | 0.000 | 0.105 |
| AE-TAEA | 2.230 | 2.468 | 2.555 | 1.718 | 2.775 | 1.629 | 2.507 | 2.873 | 3.183 |
| 1-TEPA | 5.038 | 5.654 | 6.324 | 3.175 | 5.413 | 2.702 | 5.290 | 5.112 | 5.477 |
| AE-DAEP | 0.832 | 0.808 | 1.544 | 0.156 | 0.488 | 0.107 | 1.070 | 0.396 | 0.424 |
| AE-PEEDA | 0.403 | 0.315 | 0.858 | 0.000 | 0.160 | 0.000 | 0.446 | 0.111 | 0.106 |
| iAE-PEEDA | 0.000 | 0.000 | 0.000 | 0.000 | 0.000 | 0.000 | 0.000 | 0.000 | 0.000 |
| AE-DPE | 0.130 | 0.259 | 0.457 | 0.096 | 0.092 | 0.000 | 0.307 | 0.366 | 0.235 |
| BPEA | 0.134 | 0.409 | 0.354 | 0.122 | 0.279 | 0.000 | 0.451 | 0.213 | 0.175 |
| Others | 4.461 | 4.200 | 9.270 | 1.000 | 3.341 | 0.756 | 6.468 | 2.101 | 1.798 |
| MEA conversion, % | 61.68 | 62.60 | 76.38 | 40.76 | 58.41 | 39.45 | 74.52 | 57.13 | 58.04 |
| DETA conversion, % | 36.26 | 36.76 | 46.26 | 20.64 | 33.86 | 17.85 | 38.88 | 26.66 | 28.09 |
| Acyclic(N4), wt. % | 82.96 | 83.82 | 75.88 | 95.80 | 88.88 | 96.46 | 80.67 | 92.94 | 90.97 |
| Acyclic(N5), wt. % | 82.90 | 81.94 | 73.43 | 92.89 | 88.93 | 97.60 | 77.42 | 88.03 | 90.21 |
| $\Sigma(N5)/\Sigma(N4)$, weight ratio | 0.60 | 0.65 | 0.76 | 0.45 | 0.59 | 0.37 | 0.70 | 0.59 | 0.58 |

TABLE XIV-continued

| | Example No. | | | | | | | | |
|---|---|---|---|---|---|---|---|---|---|
| | 143 | 144 | 145 | 146 | 147 | 148 | 149 | 150 | 151 |
| Acyclic(N4)/cyclic(< = N4), weight ratio | 1.41 | 1.58 | 1.09 | 4.07 | 2.32 | 4.58 | 1.20 | 3.34 | 3.12 |

TABLE XV

| | Example No. | | | | | | | | |
|---|---|---|---|---|---|---|---|---|---|
| | 152 | 153 | 154 | 155 | 156 | 157 | 158 | 159 | 160 |
| Catalyst Type | O | O | O | O | O | O | O | O | O |
| Catalyst weight, gm | 74.1 | 74.1 | 74.1 | 74.1 | 74.1 | 74.1 | 74.1 | 74.1 | 74.1 |
| Pressure, psig | 600 | 600 | 600 | 600 | 600 | 600 | 600 | 600 | 600 |
| Temperature, °C. | 270.1 | 270 | 280.2 | 259.7 | 270.1 | 259.6 | 280 | 270 | 270 |
| Time on organics, hrs. | 5 | 7.5 | 26.5 | 31.5 | 49.75 | 54 | 74 | 77.5 | 80 |
| Duration of run, hrs. | 2 | 2 | 2 | 2 | 2 | 2 | 2 | 2 | 2 |
| MEA SV, gmol/hr/kgcat | 4.32 | 4.45 | 3.86 | 4.75 | 4.55 | 4.76 | 4.72 | 4.88 | 4.68 |
| DETA/MEA mole ratio | 1.00 | 1.00 | 1.00 | 1.00 | 1.00 | 1.00 | 1.00 | 1.00 | 1.00 |
| $NH_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 0.799 | 0.893 | 2.371 | 0.614 | 1.122 | 0.619 | 1.998 | 0.866 | 1.017 |
| MEA | 16.923 | 18.142 | 8.959 | 23.814 | 16.116 | 25.054 | 10.110 | 16.161 | 17.198 |
| PIP | 1.117 | 1.135 | 0.000 | 0.764 | 1.371 | 0.835 | 1.977 | 1.209 | 1.356 |
| DETA | 50.969 | 52.494 | 43.962 | 55.309 | 48.689 | 54.390 | 47.265 | 50.840 | 51.369 |
| AEEA | 0.000 | 0.655 | 0.113 | 1.240 | 0.695 | 1.219 | 0.126 | 0.812 | 0.802 |
| AEP | 1.445 | 1.273 | 2.405 | 0.656 | 1.488 | 0.655 | 2.444 | 1.326 | 1.362 |
| HEP | 0.000 | 0.000 | 0.000 | 0.000 | 0.000 | 0.000 | 0.000 | 0.000 | 0.000 |
| TAEA | 2.361 | 2.414 | 2.424 | 1.705 | 2.211 | 1.553 | 2.474 | 2.443 | 2.319 |
| 1-TETA | 10.806 | 11.071 | 12.003 | 8.100 | 10.604 | 7.390 | 12.128 | 11.857 | 11.027 |
| DAEP | 0.223 | 0.211 | 1.034 | 0.102 | 0.328 | 0.101 | 0.788 | 0.287 | 0.268 |
| PEEDA | 0.000 | 0.150 | 0.742 | 0.000 | 0.209 | 0.000 | 0.537 | 0.199 | 0.180 |
| DPE | 0.000 | 0.000 | 0.122 | 0.000 | 0.000 | 0.000 | 0.109 | 0.000 | 0.000 |
| AE-TAEA | 1.975 | 1.711 | 2.755 | 0.748 | 2.130 | 0.714 | 2.508 | 2.424 | 1.870 |
| 1-TEPA | 3.599 | 3.260 | 6.223 | 1.444 | 4.940 | 1.373 | 5.742 | 5.006 | 3.901 |
| AE-DAEP | 0.249 | 0.000 | 0.609 | 0.000 | 0.099 | 0.000 | 0.378 | 0.000 | 0.000 |
| AE-PEEDA | 0.508 | 0.000 | 0.659 | 0.000 | 0.000 | 0.000 | 0.116 | 0.000 | 0.000 |
| iAE-PEEDA | 0.000 | 0.000 | 0.000 | 0.000 | 0.000 | 0.000 | 0.000 | 0.000 | 0.000 |
| AE-DPE | 0.236 | 0.000 | 0.800 | 0.000 | 0.118 | 0.000 | 0.334 | 0.140 | 0.099 |
| BPEA | 0.164 | 0.000 | 0.533 | 0.000 | 0.126 | 0.000 | 0.204 | 0.121 | 0.116 |
| Others | 2.605 | 0.440 | 4.535 | 0.205 | 0.635 | 0.218 | 1.962 | 0.607 | 0.694 |
| MEA conversion, % | 54.25 | 50.54 | 75.37 | 34.57 | 54.94 | 30.55 | 72.30 | 56.49 | 53.15 |
| DETA conversion, % | 18.10 | 14.95 | 28.17 | 9.69 | 19.10 | 10.39 | 23.03 | 18.65 | 16.84 |
| Acyclic(N4), wt. % | 98.33 | 97.39 | 88.38 | 98.97 | 95.98 | 98.88 | 91.06 | 96.71 | 96.75 |
| Acyclic(N5), wt. % | 82.81 | 100.00 | 77.54 | 100.00 | 95.38 | 100.00 | 88.88 | 96.60 | 96.42 |
| $\Sigma(N5)/\Sigma(N4)$, weight ratio | 0.50 | 0.36 | 0.71 | 0.22 | 0.56 | 0.23 | 0.58 | 0.52 | 0.43 |
| Acyclic(N4)/cyclic(< = N4), weight ratio | 4.73 | 4.87 | 3.35 | 6.44 | 3.77 | 5.62 | 2.58 | 4.73 | 4.21 |

TABLE XVI

| | Example No. | | | | | | | | |
|---|---|---|---|---|---|---|---|---|---|
| | 161 | 162 | 163 | 164 | 165 | 166 | 167 | 168 | 169 |
| Catalyst Type | P | P | P | P | P | P | P | P | P |
| Catalyst weight, gm | 78.9 | 78.9 | 78.9 | 78.9 | 78.9 | 78.9 | 78.9 | 78.9 | 78.9 |
| Pressure, psig | 600 | 600 | 600 | 600 | 600 | 600 | 600 | 600 | 600 |
| Temperature, °C. | 270.3 | 270.8 | 280.9 | 259.5 | 270.8 | 261.4 | 282.6 | 273.4 | 270.8 |
| Time on organics, hrs. | 4 | 7 | 26 | 31 | 50 | 55 | 74 | 79 | 99.5 |
| Duration of run, hrs. | 2 | 2 | 2 | 2 | 2 | 2 | 2 | 2 | 2 |
| MEA SV, gmol/hr/kgcat | 3.12 | 3.22 | 3.28 | 3.33 | 3.43 | 3.59 | 3.37 | 3.31 | 3.46 |
| DETA/MEA mole ratio | 1.00 | 1.00 | 1.00 | 1.00 | 1.00 | 1.00 | 1.00 | 1.00 | 1.00 |
| $NH_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 1.169 | 1.189 | 2.230 | 1.402 | 1.099 | 0.671 | 1.752 | 0.918 | 1.448 |
| MEA | 15.817 | 15.231 | 6.402 | 28.485 | 16.384 | 22.977 | 5.783 | 12.331 | 15.301 |
| PIP | 1.664 | 1.609 | 2.315 | 1.465 | 1.764 | 1.139 | 2.015 | 1.420 | 1.843 |
| DETA | 52.256 | 51.487 | 43.212 | 53.634 | 51.751 | 53.055 | 43.336 | 47.964 | 50.154 |
| AEEA | 0.283 | 0.283 | 0.000 | 1.094 | 0.153 | 0.886 | 0.000 | 0.400 | 0.339 |
| AEP | 1.915 | 1.855 | 2.978 | 0.777 | 1.978 | 1.094 | 2.884 | 1.762 | 2.059 |
| HEP | 0.000 | 0.000 | 0.000 | 0.000 | 0.000 | 0.000 | 0.000 | 0.000 | 0.000 |
| TAEA | 2.062 | 2.339 | 1.830 | 0.884 | 2.131 | 1.899 | 2.473 | 2.651 | 2.259 |
| 1-TETA | 11.022 | 11.780 | 12.001 | 6.150 | 11.397 | 9.186 | 13.960 | 13.405 | 11.464 |
| DAEP | 0.337 | 0.328 | 1.290 | 0.078 | 0.299 | 0.126 | 1.238 | 0.389 | 0.381 |
| PEEDA | 0.207 | 0.217 | 0.927 | 0.046 | 0.186 | 0.076 | 0.763 | 0.288 | 0.260 |
| DPE | 0.000 | 0.000 | 0.251 | 0.000 | 0.000 | 0.000 | 0.000 | 0.000 | 0.000 |
| AE-TAEA | 1.815 | 1.985 | 2.926 | 0.503 | 1.572 | 1.100 | 3.768 | 3.096 | 1.880 |
| 1-TEPA | 3.691 | 3.831 | 7.181 | 0.912 | 3.369 | 2.347 | 8.080 | 6.384 | 3.990 |
| AE-DAEP | 0.243 | 0.116 | 1.511 | 0.121 | 0.213 | 0.276 | 0.809 | 0.295 | 0.138 |
| AE-PEEDA | 0.000 | 0.000 | 0.928 | 0.000 | 0.000 | 0.000 | 0.238 | 0.136 | 0.000 |
| iAE-PEEDA | 0.000 | 0.000 | 0.000 | 0.000 | 0.000 | 0.000 | 0.000 | 0.000 | 0.000 |

TABLE XVI-continued

| | Example No. | | | | | | | | |
|---|---|---|---|---|---|---|---|---|---|
| | 161 | 162 | 163 | 164 | 165 | 166 | 167 | 168 | 169 |
| AE-DPE | 0.000 | 0.000 | 1.302 | 0.000 | 0.106 | 0.156 | 0.212 | 0.000 | 0.537 |
| BPEA | 0.000 | 0.000 | 0.709 | 0.000 | 0.000 | 0.000 | 0.505 | 0.127 | 0.377 |
| Others | 0.459 | 0.872 | 2.746 | 0.399 | 0.607 | 0.361 | 2.423 | 0.974 | 1.252 |
| MEA conversion, % | 56.77 | 58.52 | 82.77 | 22.06 | 55.23 | 37.72 | 84.29 | 66.57 | 58.72 |
| DETA conversion, % | 15.12 | 16.67 | 30.89 | 12.79 | 15.96 | 14.53 | 30.04 | 22.72 | 19.59 |
| Acyclic(N4), wt. % | 96.01 | 96.29 | 84.86 | 98.26 | 96.54 | 98.20 | 89.14 | 95.95 | 95.54 |
| Acyclic(N5), wt. % | 95.76 | 98.04 | 69.43 | 92.12 | 93.94 | 88.86 | 87.04 | 94.45 | 84.81 |
| Σ(N5)/Σ(N4), weight ratio | 0.42 | 0.40 | 0.89 | 0.21 | 0.38 | 0.34 | 0.74 | 0.60 | 0.48 |
| Acyclic(N4)/cyclic(< = N4), weight ratio | 3.17 | 3.52 | 1.78 | 2.97 | 3.20 | 4.55 | 2.38 | 4.16 | 3.02 |

TABLE XVII

| | Example No. | | | | | | | | |
|---|---|---|---|---|---|---|---|---|---|
| | 170 | 171 | 172 | 173 | 174 | 175 | 176 | 177 | 178 |
| Catalyst Type | Q | Q | Q | Q | Q | Q | Q | Q | Q |
| Catalyst weight, gm | 75 | 75 | 75 | 75 | 75 | 75 | 75 | 75 | 75 |
| Pressure, psig | 600 | 600 | 600 | 600 | 600 | 600 | 600 | 600 | 600 |
| Temperature, °C. | 271.8 | 270 | 280.2 | 260.9 | 270.6 | 261.2 | 281.5 | 270 | 270 |
| Time on organics, hrs. | 5 | 8.5 | 25 | 30 | 34 | 49 | 55 | 76 | 78 |
| Duration of run, hrs. | 2 | 2 | 2 | 2 | 2 | 2 | 2 | 2 | 2 |
| MEA SV, gmol/hr/kgcat | 4.47 | 4.56 | 4.56 | 4.83 | 4.82 | 4.39 | 4.36 | 4.29 | 4.45 |
| DETA/MEA mole ratio | 1.00 | 1.00 | 1.00 | 1.00 | 1.00 | 1.00 | 1.00 | 1.00 | 1.00 |
| NH3/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 0.810 | 0.695 | 1.728 | 0.496 | 1.051 | 0.606 | 2.250 | 1.081 | 1.235 |
| MEA | 17.286 | 19.405 | 12.726 | 23.941 | 20.602 | 23.930 | 10.050 | 16.058 | 17.476 |
| PIP | 0.000 | 0.893 | 1.726 | 0.691 | 1.246 | 0.771 | 1.912 | 1.336 | 1.440 |
| DETA | 49.596 | 50.668 | 47.269 | 55.529 | 51.649 | 54.615 | 43.590 | 49.568 | 50.015 |
| AEEA | 0.486 | 0.691 | 0.138 | 1.063 | 0.715 | 1.234 | 0.241 | 0.655 | 0.684 |
| AEP | 1.371 | 0.938 | 1.974 | 0.669 | 1.231 | 0.731 | 2.221 | 1.449 | 1.413 |
| HEP | 0.000 | 0.000 | 0.000 | 0.000 | 0.000 | 0.000 | 0.000 | 0.000 | 0.000 |
| TAEA | 2.260 | 2.121 | 2.389 | 1.786 | 2.157 | 1.878 | 2.470 | 2.355 | 2.187 |
| l-TETA | 12.072 | 9.647 | 11.834 | 8.149 | 10.098 | 8.642 | 12.086 | 11.364 | 11.254 |
| DAEP | 0.252 | 0.179 | 0.649 | 0.097 | 0.211 | 0.112 | 0.851 | 0.313 | 0.251 |
| PEEDA | 0.179 | 0.124 | 0.372 | 0.070 | 0.144 | 0.071 | 0.630 | 0.209 | 0.172 |
| DPE | 0.000 | 0.000 | 0.000 | 0.000 | 0.000 | 0.000 | 0.068 | 0.000 | 0.000 |
| AE-TAEA | 2.502 | 1.504 | 2.751 | 0.826 | 1.555 | 0.937 | 2.780 | 2.257 | 2.015 |
| l-TEPA | 4.580 | 2.966 | 5.577 | 1.450 | 2.954 | 1.689 | 6.099 | 4.795 | 4.114 |
| AE-DAEP | 0.259 | 0.000 | 0.387 | 0.000 | 0.084 | 0.000 | 0.395 | 0.000 | 0.231 |
| AE-PEEDA | 0.105 | 0.000 | 0.100 | 0.000 | 0.000 | 0.000 | 0.111 | 0.000 | 0.177 |
| iAE-PEEDA | 0.000 | 0.000 | 0.000 | 0.000 | 0.000 | 0.000 | 0.000 | 0.000 | 0.000 |
| AE-DPE | 0.166 | 0.000 | 1.181 | 0.000 | 0.077 | 0.000 | 0.451 | 0.115 | 0.108 |
| BPEA | 0.000 | 0.068 | 0.138 | 0.000 | 0.100 | 0.000 | 0.352 | 0.164 | 0.105 |
| Others | 0.756 | 0.599 | 1.252 | 0.294 | 0.726 | 0.304 | 2.563 | 0.790 | 0.884 |
| MEA conversion, % | 52.45 | 44.86 | 64.94 | 34.49 | 44.04 | 34.90 | 71.93 | 55.92 | 52.53 |
| DETA conversion, % | 18.91 | 14.44 | 22.61 | 9.70 | 16.62 | 11.71 | 27.65 | 19.14 | 19.26 |
| Acyclic(N4), wt. % | 97.08 | 97.48 | 93.30 | 98.35 | 97.19 | 98.29 | 90.39 | 96.33 | 96.95 |
| Acyclic(N5), wt. % | 93.03 | 98.50 | 91.18 | 100.00 | 94.52 | 100.00 | 87.15 | 96.19 | 90.81 |
| Σ(N5)/Σ(N4), weight ratio | 0.52 | 0.38 | 0.60 | 0.23 | 0.38 | 0.25 | 0.63 | 0.51 | 0.49 |
| Acyclic(N4)/cyclic(< = N4), weight ratio | 7.95 | 5.51 | 3.01 | 6.51 | 4.33 | 6.24 | 2.56 | 4.15 | 4.10 |

TABLE XVIII

| | Example No. | | | | | | | | |
|---|---|---|---|---|---|---|---|---|---|
| | 179 | 180 | 181 | 182 | 183 | 184 | 185 | 186 | 187 |
| Catalyst Type | R | R | R | R | R | R | R | R | R |
| Catalyst weight, gm | 74.9 | 74.9 | 74.9 | 74.9 | 74.9 | 74.9 | 74.9 | 74.9 | 74.9 |
| Pressure, psig | 600 | 600 | 600 | 600 | 600 | 600 | 600 | 600 | 600 |
| Temperature, °C. | 269.3 | 269.2 | 279.4 | 258.8 | 269.2 | 259.4 | 279.2 | 268.9 | 269.6 |
| Time on organics, hrs. | 23.5 | 27.5 | 47 | 52 | 71 | 76 | 95 | 100 | 120 |
| Duration of run, hrs. | 2 | 2 | 2 | 2 | 2 | 2 | 2 | 2 | 2 |
| MEA SV, gmol/hr/kgcat | 3.93 | 3.73 | 3.63 | 3.84 | 3.64 | 3.67 | 3.53 | 3.56 | 3.35 |
| DETA/MEA mole ratio | 1.00 | 1.00 | 1.00 | 1.00 | 1.00 | 1.00 | 1.00 | 1.00 | 1.00 |
| NH3/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 0.980 | 0.906 | 2.141 | 0.568 | 1.040 | 0.888 | 2.069 | 1.289 | 1.356 |
| MEA | 20.085 | 19.419 | 12.916 | 27.282 | 20.217 | 25.518 | 12.998 | 22.393 | 20.330 |
| PIP | 1.509 | 1.448 | 2.211 | 0.850 | 1.624 | 0.922 | 2.027 | 1.573 | 1.718 |
| DETA | 52.434 | 51.557 | 46.545 | 55.689 | 52.087 | 54.254 | 47.895 | 52.707 | 52.473 |
| AEEA | 0.262 | 0.255 | 0.178 | 0.429 | 0.220 | 0.421 | 0.000 | 0.268 | 0.263 |
| AEP | 1.402 | 1.413 | 2.106 | 0.696 | 1.428 | 0.823 | 2.307 | 1.348 | 1.537 |
| HEP | 0.000 | 0.000 | 0.000 | 0.000 | 0.000 | 0.000 | 0.000 | 0.000 | 0.000 |
| TAEA | 1.988 | 2.084 | 2.094 | 1.374 | 1.867 | 1.680 | 1.920 | 1.733 | 1.944 |
| l-TETA | 9.493 | 9.950 | 10.311 | 6.413 | 8.947 | 7.890 | 9.728 | 7.823 | 8.760 |

TABLE XVIII-continued

| | Example No. | | | | | | | | |
|---|---|---|---|---|---|---|---|---|---|
| | 179 | 180 | 181 | 182 | 183 | 184 | 185 | 186 | 187 |
| DAEP | 0.173 | 0.198 | 0.645 | 0.058 | 0.382 | 0.275 | 0.714 | 0.279 | 0.373 |
| PEEDA | 0.127 | 0.146 | 0.460 | 0.052 | 0.150 | 0.192 | 0.328 | 0.000 | 0.000 |
| DPE | 0.000 | 0.000 | 0.056 | 0.000 | 0.000 | 0.000 | 0.000 | 0.000 | 0.000 |
| AE-TAEA | 0.000 | 0.000 | 0.000 | 0.000 | 0.000 | 0.000 | 0.000 | 0.000 | 0.000 |
| 1-TEPA | 1.257 | 1.371 | 2.257 | 0.448 | 1.195 | 0.801 | 2.316 | 0.979 | 1.375 |
| AE-DAEP | 0.000 | 0.292 | 0.334 | 0.000 | 0.091 | 0.104 | 0.624 | 0.000 | 0.000 |
| AE-PEEDA | 0.084 | 0.135 | 0.070 | 0.000 | 0.000 | 0.000 | 0.485 | 0.000 | 0.000 |
| iAE-PEEDA | 0.000 | 0.000 | 0.000 | 0.000 | 0.000 | 0.000 | 0.000 | 0.000 | 0.000 |
| AE-DPE | 0.208 | 0.779 | 1.181 | 0.000 | 0.365 | 0.281 | 0.490 | 0.000 | 0.365 |
| BPEA | 0.000 | 0.000 | 0.287 | 0.000 | 0.000 | 0.000 | 0.631 | 0.000 | 0.000 |
| Others | 2.920 | 3.097 | 5.689 | 1.582 | 2.587 | 1.652 | 6.070 | 1.507 | 2.305 |
| MEA conversion, % | 44.42 | 46.57 | 63.21 | 25.08 | 43.62 | 30.56 | 63.95 | 36.84 | 43.63 |
| DETA conversion, % | 13.76 | 15.69 | 21.21 | 9.11 | 13.68 | 12.26 | 21.06 | 11.65 | 13.54 |
| Acyclic(N4), wt. % | 97.46 | 97.22 | 91.45 | 98.61 | 95.31 | 95.35 | 91.79 | 97.16 | 96.64 |
| Acyclic(N5), wt. % | 81.13 | 53.17 | 72.13 | 100.00 | 72.41 | 67.51 | 50.94 | 100.00 | 79.03 |
| Σ(N5)/Σ(N4), weight ratio | 0.13 | 0.21 | 0.23 | 0.06 | 0.15 | 0.12 | 0.36 | 0.10 | 0.16 |
| Acyclic(N4)/cyclic(< = N4), weight ratio | 3.58 | 3.76 | 2.26 | 4.70 | 3.02 | 4.33 | 2.17 | 2.99 | 2.95 |

TABLE XIX

| | Example No. | | | | | | | | |
|---|---|---|---|---|---|---|---|---|---|
| | 188 | 189 | 190 | 191 | 192 | 193 | 194 | 195 | 196 |
| Catalyst Type | S | S | S | S | S | S | S | S | S |
| Catalyst weight, gm | 77.1 | 77.1 | 77.1 | 77.1 | 77.1 | 77.1 | 77.1 | 77.1 | 77.1 |
| Pressure, psig | 600 | 600 | 600 | 600 | 600 | 600 | 600 | 600 | 600 |
| Temperature, °C. | 270.3 | 270.8 | 280.9 | 259.5 | 270.8 | 261.4 | 282.6 | 272.4 | 270.8 |
| Time on organics, hrs. | 4 | 7 | 26 | 31 | 50 | 55 | 74 | 79 | 99.5 |
| Duration of run, hrs. | 2 | 2 | 2 | 2 | 2 | 2 | 2 | 2 | 2 |
| MEA SV, gmol/hr/kgcat | 3.57 | 3.84 | 3.80 | 3.90 | 4.07 | 4.29 | 4.00 | 4.02 | 4.09 |
| DETA/MEA mole ratio | 1.00 | 1.00 | 1.00 | 1.00 | 1.00 | 1.00 | 1.00 | 1.00 | 1.00 |
| NH$_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 1.064 | 1.067 | 2.949 | 1.044 | 1.126 | 0.634 | 1.319 | 0.655 | 0.856 |
| MEA | 19.737 | 20.664 | 15.833 | 33.488 | 22.772 | 28.699 | 10.428 | 16.261 | 18.470 |
| PIP | 1.010 | 1.060 | 2.508 | 1.029 | 1.433 | 0.868 | 1.591 | 0.964 | 1.166 |
| DETA | 52.528 | 52.478 | 47.832 | 54.061 | 52.460 | 55.001 | 46.963 | 50.475 | 53.782 |
| AEEA | 0.618 | 0.649 | 0.219 | 0.981 | 0.066 | 1.055 | 0.134 | 0.751 | 0.219 |
| AEP | 1.111 | 1.092 | 2.117 | 0.537 | 1.255 | 0.600 | 2.045 | 1.283 | 1.400 |
| HEP | 0.000 | 0.000 | 0.000 | 0.000 | 0.000 | 0.000 | 0.000 | 0.000 | 0.000 |
| TAEA | 1.982 | 1.964 | 1.306 | 0.527 | 1.836 | 1.309 | 2.590 | 2.505 | 2.082 |
| 1-TETA | 10.911 | 10.012 | 8.857 | 4.302 | 9.388 | 6.368 | 13.545 | 12.661 | 10.355 |
| DAEP | 0.183 | 0.172 | 0.652 | 0.031 | 0.165 | 0.065 | 0.739 | 0.233 | 0.193 |
| PEEDA | 0.134 | 0.122 | 0.487 | 0.000 | 0.108 | 0.000 | 0.478 | 0.186 | 0.154 |
| DPE | 0.000 | 0.000 | 0.321 | 0.000 | 0.000 | 0.000 | 0.000 | 0.000 | 0.000 |
| AE-TAEA | 1.065 | 1.592 | 1.529 | 0.149 | 0.830 | 0.433 | 3.290 | 2.387 | 1.478 |
| 1-TEPA | 2.728 | 3.034 | 2.962 | 0.125 | 2.166 | 0.748 | 6.467 | 4.760 | 2.918 |
| AE-DAEP | 0.123 | 0.000 | 0.376 | 0.000 | 0.049 | 0.125 | 0.366 | 0.110 | 0.086 |
| AE-PEEDA | 0.000 | 0.000 | 0.218 | 0.000 | 0.000 | 0.000 | 0.000 | 0.000 | 0.000 |
| iAE-PEEDA | 0.000 | 0.000 | 0.000 | 0.000 | 0.000 | 0.000 | 0.000 | 0.000 | 0.000 |
| AE-DPE | 0.142 | 0.198 | 0.600 | 0.000 | 0.000 | 0.000 | 0.151 | 0.105 | 0.000 |
| BPEA | 0.000 | 0.000 | 0.310 | 0.000 | 0.000 | 0.000 | 0.157 | 0.065 | 0.000 |
| Others | 0.983 | 0.675 | 2.785 | 0.347 | 1.245 | 0.414 | 1.358 | 0.510 | 1.052 |
| MEA conversion, % | 46.25 | 43.91 | 56.39 | 7.91 | 37.98 | 21.73 | 71.61 | 56.02 | 49.81 |
| DETA conversion, % | 14.98 | 15.34 | 21.70 | 11.65 | 15.09 | 10.85 | 24.02 | 18.86 | 13.13 |
| Acyclic(N4), wt. % | 97.60 | 97.60 | 87.44 | 99.35 | 97.63 | 99.16 | 92.99 | 97.31 | 97.29 |
| Acyclic(N5), wt. % | 93.48 | 95.89 | 74.91 | 100.00 | 98.39 | 90.46 | 93.53 | 96.24 | 98.09 |
| Σ(N5)/Σ(N4), weight ratio | 0.31 | 0.39 | 0.52 | 0.06 | 0.26 | 0.17 | 0.60 | 0.48 | 0.35 |
| Acyclic(N4)/cyclic(< = N4), weight ratio | 5.29 | 4.89 | 1.67 | 3.02 | 3.79 | 5.01 | 3.32 | 5.69 | 4.27 |

TABLE XX

| | Example No. | | | | | | | | |
|---|---|---|---|---|---|---|---|---|---|
| | 197 | 198 | 199 | 200 | 201 | 202 | 203 | 204 | 205 |
| Catalyst Type | T | T | T | T | T | T | T | T | T |
| Catalyst weight, gm | 89.1 | 89.1 | 89.1 | 89.1 | 89.1 | 89.1 | 89.1 | 89.1 | 89.1 |
| Pressure, psig | 600 | 600 | 600 | 600 | 600 | 600 | 600 | 600 | 600 |
| Temperature, °C. | 274.4 | 274.4 | 280.9 | 259.8 | 270.6 | 259.9 | 281.6 | 270.4 | 270.4 |
| Time on organics, hrs. | 22 | 26 | 45.5 | 50.5 | 69 | 74.5 | 95 | 119 | 120 |
| Duration of run, hrs. | 2 | 2 | 2 | 2 | 2 | 2 | 2 | 1 | 1 |
| MEA SV, gmol/hr/kgcat | 3.54 | 3.49 | 3.26 | 3.62 | 3.67 | 3.54 | 3.50 | 7.34 | 3.64 |
| DETA/MEA mole ratio | 1.00 | 1.00 | 1.00 | 1.00 | 1.00 | 1.00 | 1.00 | 1.00 | 1.00 |
| NH$_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 2.720 | 2.147 | 6.050 | 1.506 | 2.063 | 0.510 | 4.522 | 1.700 | 1.717 |

TABLE XX-continued

| | Example No. | | | | | | | | |
|---|---|---|---|---|---|---|---|---|---|
| | 197 | 198 | 199 | 200 | 201 | 202 | 203 | 204 | 205 |
| MEA | 17.172 | 17.646 | 11.090 | 24.376 | 18.880 | 23.711 | 12.670 | 19.091 | 19.532 |
| PIP | 3.605 | 3.285 | 6.865 | 1.922 | 2.983 | 1.500 | 5.411 | 2.536 | 2.650 |
| DETA | 45.019 | 47.846 | 36.936 | 51.126 | 46.069 | 60.718 | 38.319 | 46.051 | 46.810 |
| AEEA | 1.105 | 0.896 | 0.266 | 2.671 | 1.310 | 1.103 | 0.484 | 1.774 | 1.241 |
| AEP | 2.925 | 2.891 | 6.159 | 1.195 | 2.402 | 1.058 | 4.968 | 2.089 | 2.120 |
| HEP | 0.000 | 0.000 | 0.000 | 0.000 | 0.000 | 0.000 | 0.000 | 0.000 | 0.000 |
| TAEA | 1.209 | 0.424 | 0.376 | 0.813 | 1.233 | 0.599 | 0.517 | 1.195 | 0.782 |
| l-TETA | 10.239 | 10.478 | 8.946 | 8.826 | 10.269 | 6.805 | 9.581 | 9.683 | 9.534 |
| DAEP | 0.772 | 0.760 | 1.868 | 0.178 | 0.640 | 0.127 | 1.531 | 0.559 | 0.548 |
| PEEDA | 0.840 | 0.880 | 2.576 | 0.170 | 0.724 | 0.140 | 2.159 | 0.624 | 0.603 |
| DPE | 0.041 | 0.054 | 0.072 | 0.000 | 0.086 | 0.000 | 0.101 | 0.052 | 0.032 |
| AE-TAEA | 0.934 | 0.596 | 0.549 | 0.231 | 0.979 | 0.000 | 0.711 | 0.904 | 0.788 |
| l-TEPA | 4.738 | 4.381 | 4.535 | 2.107 | 4.687 | 0.000 | 5.357 | 4.353 | 4.151 |
| AE-DAEP | 0.398 | 0.278 | 1.152 | 0.049 | 0.262 | 0.000 | 0.969 | 0.257 | 0.237 |
| AE-PEEDA | 0.126 | 0.129 | 0.254 | 0.000 | 0.115 | 0.000 | 0.235 | 0.109 | 0.104 |
| iAE-PEEDA | 0.000 | 0.000 | 0.000 | 0.000 | 0.000 | 0.000 | 0.000 | 0.000 | 0.000 |
| AE-DPE | 0.000 | 0.000 | 0.047 | 0.000 | 0.000 | 0.000 | 0.000 | 0.000 | 0.000 |
| BPEA | 0.000 | 0.000 | 0.000 | 0.000 | 0.000 | 0.000 | 0.000 | 0.000 | 0.000 |
| Others | 1.657 | 1.439 | 3.878 | 0.448 | 1.598 | 0.000 | 3.154 | 1.704 | 1.370 |
| MEA Conversion, % | 53.55 | 52.50 | 70.19 | 33.82 | 49.12 | 35.88 | 65.36 | 47.50 | 45.94 |
| DETA Conversion, % | 27.63 | 23.46 | 41.00 | 17.51 | 26.21 | 2.41 | 37.74 | 24.74 | 23.00 |
| Acyclic(N4), wt. % | 87.38 | 86.56 | 67.36 | 96.51 | 88.80 | 96.51 | 72.70 | 89.80 | 89.71 |
| Acyclic(N5), wt. % | 91.53 | 92.44 | 77.77 | 97.93 | 93.75 | 0.00 | 83.44 | 93.50 | 93.54 |
| Σ(N5)/Σ(N4), weight ratio | 0.47 | 0.43 | 0.47 | 0.24 | 0.47 | 0.00 | 0.52 | 0.46 | 0.46 |
| Acyclic(N4)/cyclic(< = N4), weight ratio | 1.40 | 1.39 | 0.53 | 2.78 | 1.68 | 2.61 | 0.71 | 1.86 | 1.73 |

TABLE XXI

| | Example No. | | | | | | | | |
|---|---|---|---|---|---|---|---|---|---|
| | 206 | 207 | 208 | 209 | 210 | 211 | 212 | 213 | 214 |
| Catalyst Type | U | U | U | U | U | U | U | U | U |
| Catalyst weight, gm | 91.7 | 91.7 | 91.7 | 91.7 | 91.7 | 91.7 | 91.7 | 91.7 | 91.7 |
| Pressure, psig | 600 | 600 | 600 | 600 | 600 | 600 | 600 | 600 | 600 |
| Temperature, °C. | 268.6 | 268.9 | 278.6 | 259.1 | 268.3 | 258.2 | 278.9 | 269 | 269.6 |
| Time on organics, hrs. | 3 | 22 | 27 | 51 | 69.5 | 74 | 93 | 99 | 116.5 |
| Duration of run, hrs. | 2 | 2 | 2 | 2 | 2 | 2 | 2 | 2 | 2 |
| MEA SV, gmol/hr/kgcat | 1.87 | 2.59 | 2.79 | 2.74 | 2.82 | 2.85 | 2.58 | 2.74 | 2.59 |
| DETA/MEA mole ratio | 1.00 | 1.00 | 1.00 | 1.00 | 1.00 | 1.00 | 1.00 | 1.00 | 1.00 |
| $NH_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 2.183 | 2.188 | 1.770 | 0.548 | 1.020 | 0.597 | 1.940 | 1.065 | 1.184 |
| MEA | 27.641 | 27.702 | 4.345 | 16.309 | 9.520 | 16.119 | 3.529 | 9.960 | 7.884 |
| PIP | 0.359 | 0.359 | 1.724 | 0.781 | 1.295 | 0.831 | 1.768 | 1.334 | 1.404 |
| DETA | 50.123 | 50.233 | 32.473 | 45.537 | 37.563 | 44.839 | 30.507 | 38.688 | 35.307 |
| AEEA | 1.469 | 1.473 | 0.272 | 2.441 | 0.835 | 2.461 | 0.259 | 0.891 | 0.693 |
| AEP | 0.425 | 0.425 | 2.604 | 0.939 | 1.587 | 0.990 | 2.516 | 1.641 | 1.764 |
| HEP | 0.000 | 0.000 | 0.000 | 0.000 | 0.000 | 0.000 | 0.000 | 0.000 | 0.000 |
| TAEA | 0.540 | 0.541 | 1.884 | 1.758 | 2.057 | 1.894 | 1.864 | 1.979 | 2.025 |
| l-TETA | 5.907 | 5.920 | 14.212 | 13.575 | 13.856 | 13.962 | 13.839 | 13.903 | 13.810 |
| DAEP | 0.000 | 0.000 | 1.323 | 0.221 | 0.725 | 0.221 | 1.371 | 0.816 | 0.894 |
| PEEDA | 0.077 | 0.077 | 1.066 | 0.195 | 0.561 | 0.189 | 1.056 | 0.588 | 0.667 |
| DPE | 0.000 | 0.000 | 0.212 | 0.073 | 0.453 | 0.073 | 0.204 | 0.194 | 0.226 |
| AE-TAEA | 0.243 | 0.243 | 3.128 | 1.661 | 2.763 | 1.921 | 3.001 | 2.711 | 2.954 |
| l-TEPA | 0.585 | 0.586 | 9.266 | 4.428 | 7.937 | 4.979 | 9.181 | 7.693 | 8.505 |
| AE-DAEP | 0.000 | 0.000 | 1.117 | 0.186 | 0.635 | 0.255 | 1.174 | 0.589 | 0.748 |
| AE-PEEDA | 0.151 | 0.152 | 0.266 | 0.147 | 0.165 | 0.151 | 0.247 | 0.180 | 0.234 |
| iAE-PEEDA | 0.000 | 0.000 | 0.000 | 0.000 | 0.000 | 0.000 | 0.000 | 0.000 | 0.000 |
| AE-DPE | 0.000 | 0.000 | 0.400 | 0.000 | 0.339 | 0.241 | 0.370 | 0.292 | 0.377 |
| BPEA | 0.000 | 0.000 | 0.692 | 0.194 | 0.581 | 0.058 | 0.692 | 0.473 | 0.620 |
| Others | 1.677 | 1.680 | 14.327 | 2.888 | 11.047 | 4.339 | 13.830 | 8.942 | 12.375 |
| MEA Conversion, % | 20.18 | 20.18 | 88.44 | 54.92 | 74.73 | 56.63 | 90.23 | 73.20 | 78.90 |
| DETA Conversion, % | 13.97 | 13.97 | 48.67 | 25.19 | 40.75 | 28.30 | 49.82 | 38.12 | 43.84 |
| Acyclic(N4), % | 98.82 | 98.82 | 86.09 | 96.91 | 90.15 | 97.10 | 85.65 | 90.86 | 89.86 |
| Acyclic(N5), % | 84.54 | 84.54 | 83.35 | 92.03 | 86.15 | 90.74 | 83.07 | 87.15 | 85.28 |
| Σ(N5)/Σ(N4), weight ratio | 0.15 | 0.15 | 0.80 | 0.42 | 0.70 | 0.47 | 0.80 | 0.68 | 0.76 |
| Acyclic(N4)/cyclic (< = N4), weight ratio | 7.50 | 7.50 | 2.32 | 6.94 | 3.44 | 6.91 | 2.27 | 3.47 | 3.20 |

TABLE XXII

| | Example No. | | | | | | | | |
|---|---|---|---|---|---|---|---|---|---|
| | 215 | 216 | 217 | 218 | 219 | 220 | 221 | 222 | 223 |
| Catalyst Type | V | V | V | V | V | V | V | V | V |
| Catalyst weight, gm | 79.6 | 79.6 | 79.6 | 79.6 | 79.6 | 79.6 | 79.6 | 79.6 | 79.6 |

TABLE XXII-continued

| | Example No. | | | | | | | | |
|---|---|---|---|---|---|---|---|---|---|
| | 215 | 216 | 217 | 218 | 219 | 220 | 221 | 222 | 223 |
| Pressure, psig | 600 | 600 | 600 | 600 | 600 | 600 | 600 | 600 | 600 |
| Temperature, °C. | 268.6 | 268.9 | 278.6 | 259.1 | 268.3 | 258.2 | 278.9 | 269 | 269.6 |
| Time on organics, hrs. | 3 | 22 | 27 | 51 | 69.5 | 74 | 93 | 99 | 116.5 |
| Duration of run, hrs. | 2 | 2 | 2 | 2 | 2 | 2 | 2 | 2 | 2 |
| MEA SV, gmol/hr/kgcat | 3.34 | 2.66 | 2.48 | 3.46 | 3.32 | 3.85 | 2.73 | 2.84 | 2.42 |
| DETA/MEA mole ratio | 1.00 | 1.00 | 1.00 | 1.00 | 1.00 | 1.00 | 1.00 | 1.00 | 1.00 |
| $NH_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 0.402 | 0.984 | 1.667 | 0.394 | 0.739 | 0.489 | 1.751 | 1.291 | 1.139 |
| MEA | 15.275 | 9.355 | 3.835 | 17.705 | 9.833 | 17.982 | 3.544 | 9.828 | 6.948 |
| PIP | 1.023 | 1.416 | 1.735 | 0.823 | 1.192 | 0.874 | 1.765 | 1.556 | 1.504 |
| DETA | 45.636 | 38.050 | 30.599 | 46.962 | 37.022 | 46.771 | 30.103 | 39.458 | 33.830 |
| AEEA | 0.563 | 0.635 | 0.229 | 2.288 | 0.818 | 2.437 | 0.237 | 0.909 | 0.647 |
| AEP | 1.146 | 1.654 | 2.572 | 0.964 | 1.493 | 0.918 | 2.432 | 1.661 | 1.837 |
| HEP | 0.000 | 0.000 | 0.000 | 0.000 | 0.000 | 0.000 | 0.000 | 0.000 | 0.000 |
| TAEA | 1.055 | 1.701 | 1.742 | 1.714 | 1.968 | 1.798 | 1.727 | 1.992 | 1.965 |
| l-TETA | 14.353 | 14.398 | 14.401 | 12.742 | 14.026 | 12.801 | 13.949 | 14.704 | 14.368 |
| DAEP | 0.249 | 0.654 | 1.412 | 0.204 | 0.702 | 0.176 | 1.305 | 0.678 | 0.917 |
| PEEDA | 0.325 | 0.561 | 1.102 | 0.191 | 0.551 | 0.167 | 1.053 | 0.549 | 0.702 |
| DPE | 0.121 | 0.297 | 0.229 | 0.068 | 0.281 | 0.065 | 0.214 | 0.195 | 0.339 |
| AE-TAEA | 1.394 | 2.685 | 2.896 | 1.785 | 2.857 | 2.350 | 2.894 | 2.684 | 2.950 |
| l-TEPA | 5.057 | 7.739 | 7.422 | 4.753 | 8.218 | 4.811 | 9.500 | 7.913 | 9.201 |
| AE-DAEP | 0.509 | 0.622 | 1.153 | 0.165 | 0.574 | 0.183 | 1.120 | 0.446 | 0.733 |
| AE-PEEDA | 0.114 | 0.112 | 0.260 | 0.085 | 0.186 | 0.082 | 0.318 | 0.112 | 0.220 |
| iAE-PEEDA | 0.000 | 0.000 | 0.000 | 0.000 | 0.000 | 0.000 | 0.000 | 0.000 | 0.000 |
| AE-DPE | 0.157 | 0.184 | 0.396 | 0.088 | 0.450 | 0.068 | 0.417 | 0.000 | 0.374 |
| BPEA | 0.332 | 0.572 | 0.676 | 0.225 | 0.581 | 0.214 | 0.673 | 0.443 | 0.631 |
| Others | 4.749 | 7.940 | 13.943 | 2.415 | 10.748 | 2.214 | 13.837 | 6.329 | 12.335 |
| MEA Conversion, % | 58.32 | 74.19 | 89.50 | 51.84 | 73.69 | 51.51 | 90.14 | 73.15 | 81.27 |
| DETA Conversion, % | 26.00 | 37.61 | 50.21 | 24.08 | 41.13 | 25.04 | 50.22 | 35.93 | 45.79 |
| Acyclic(N4), % | 95.68 | 91.41 | 85.48 | 96.90 | 91.24 | 97.28 | 85.90 | 92.15 | 89.29 |
| Acyclic(N5), % | 85.30 | 87.49 | 83.21 | 92.07 | 86.08 | 92.90 | 83.07 | 91.37 | 86.12 |
| $\Sigma(N5)/\Sigma(N4)$, weight ratio | 0.47 | 0.68 | 0.78 | 0.48 | 0.73 | 0.51 | 0.82 | 0.64 | 0.77 |
| Acyclic(N4)/cyclic ($<$ = N4), weight ratio | 5.38 | 3.51 | 2.29 | 6.43 | 3.79 | 6.63 | 2.32 | 3.60 | 3.08 |

TABLE XXIII

| | Example No. | | | | | | | | | |
|---|---|---|---|---|---|---|---|---|---|---|
| | 224 | 225 | 226 | 227 | 228 | 229 | 230 | 231 | 232 | 233 |
| Catalyst Type | W | W | W | W | W | W | W | W | W | W |
| Catalyst weight, gm | 87.7 | 87.7 | 87.7 | 87.7 | 87.7 | 87.7 | 87.7 | 87.7 | 87.7 | 87.7 |
| Pressure, psig | 603 | 596 | 606 | 600 | 600 | 600 | 607 | 600 | 590 | 600 |
| Temperature, °C. | 269 | 279 | 260 | 270 | 270 | 259.6 | 279 | 270 | 280 | 270 |
| Time on organics, hrs. | 21 | 28 | 49 | 54 | 73.5 | 97.5 | 116 | 121 | 139 | 144 |
| Duration of run, hrs. | 2 | 2 | 2 | 2 | 2 | 2 | 2 | 2 | 2 | 2 |
| MEA SV, gmol/hr/kgcat | 0.91 | 0.59 | 2.75 | 1.43 | 2.59 | 2.77 | 2.41 | 2.60 | 2.29 | 2.43 |
| DETA/MEA mole ratio | 1.00 | 1.00 | 1.00 | 1.00 | 1.00 | 1.00 | 1.00 | 1.00 | 1.00 | 1.00 |
| $NH_3$/MEA mole ratio | 5.97 | 5.97 | 5.97 | 5.97 | 5.97 | 5.97 | 5.97 | 5.97 | 5.97 | 5.97 |
| Crude product composition, wt. % | | | | | | | | | | |
| EDA | 2.350 | 1.919 | 0.622 | 0.752 | 0.640 | 0.391 | 1.122 | 0.738 | 1.310 | 1.032 |
| MEA | 23.993 | 22.805 | 29.044 | 27.951 | 26.940 | 30.561 | 23.577 | 28.244 | 22.626 | 14.670 |
| PIP | 0.625 | 0.683 | 0.215 | 0.276 | 0.295 | 0.203 | 0.700 | 0.146 | 0.834 | 1.073 |
| DETA | 52.709 | 52.718 | 55.792 | 52.407 | 51.421 | 56.953 | 49.965 | 55.022 | 49.613 | 43.078 |
| AEEA | 0.839 | 0.906 | 0.676 | 0.848 | 0.865 | 0.965 | 0.936 | 1.077 | 0.953 | 1.870 |
| AEP | 0.670 | 0.712 | 0.316 | 0.322 | 0.328 | 0.257 | 0.586 | 0.387 | 0.639 | 1.002 |
| HEP | 0.000 | 0.000 | 0.000 | 0.000 | 0.000 | 0.000 | 0.000 | 0.000 | 0.000 | 0.000 |
| TAEA | 1.188 | 1.399 | 0.875 | 0.858 | 0.973 | 0.696 | 1.543 | 1.161 | 1.716 | 2.408 |
| l-TETA | 5.320 | 6.386 | 4.275 | 4.119 | 4.573 | 3.717 | 7.655 | 5.591 | 8.550 | 11.687 |
| DAEP | 0.347 | 0.266 | 0.123 | 0.104 | 0.092 | 0.061 | 0.191 | 0.106 | 0.224 | 0.280 |
| PEEDA | 0.057 | 0.170 | 0.083 | 0.060 | 0.058 | 0.038 | 0.023 | 0.067 | 0.028 | 0.239 |
| DPE | 0.083 | 0.083 | 0.030 | 0.034 | 0.035 | 0.027 | 0.067 | 0.045 | 0.075 | 0.094 |
| AE-TAEA | 0.899 | 0.988 | 0.607 | 0.509 | 0.572 | 0.374 | 0.052 | 0.789 | 1.664 | 3.061 |
| l-TEPA | 1.485 | 1.792 | 1.076 | 0.867 | 0.939 | 0.666 | 2.604 | 1.419 | 3.031 | 5.965 |
| AE-DAEP | 0.280 | 0.202 | 0.116 | 0.085 | 0.000 | 0.035 | 0.142 | 0.084 | 0.162 | 0.312 |
| AE-PEEDA | 0.108 | 0.080 | 0.000 | 0.033 | 0.069 | 0.000 | 0.000 | 0.035 | 0.042 | 0.048 |
| iAE-PEEDA | 0.000 | 0.000 | 0.000 | 0.000 | 0.000 | 0.000 | 0.000 | 0.000 | 0.000 | 0.000 |
| AE-DPE | 0.043 | 0.000 | 0.000 | 0.000 | 0.000 | 0.000 | 0.000 | 0.000 | 0.000 | 0.146 |
| BPEA | 0.107 | 0.106 | 0.059 | 0.022 | 0.081 | 0.000 | 0.175 | 0.080 | 0.210 | 0.374 |
| Others | 2.935 | 3.026 | 0.992 | 0.725 | 0.939 | 0.685 | 3.151 | 0.949 | 2.575 | 3.282 |
| MEA Conversion, % | 33.53 | 37.20 | 19.34 | 18.02 | 20.14 | 15.44 | 33.80 | 22.92 | 37.97 | 59.15 |
| DETA Conversion, % | 13.21 | 13.72 | 7.91 | 8.64 | 9.40 | 6.34 | 16.63 | 10.76 | 19.16 | 28.71 |
| Acyclic(N4), % | 93.03 | 93.76 | 95.63 | 96.18 | 96.79 | 97.22 | 97.03 | 96.87 | 96.92 | 95.83 |
| Acyclic(N5), % | 81.55 | 87.74 | 90.59 | 90.79 | 90.93 | 96.73 | 89.33 | 91.76 | 91.91 | 91.11 |
| $\Sigma(N5)/\Sigma(N4)$, weight ratio | 0.42 | 0.38 | 0.34 | 0.29 | 0.29 | 0.24 | 0.31 | 0.35 | 0.48 | 0.67 |

TABLE XXIII-continued

| | Example No. | | | | | | | | | |
|---|---|---|---|---|---|---|---|---|---|---|
| | 224 | 225 | 226 | 227 | 228 | 229 | 230 | 231 | 232 | 233 |
| Acyclic(N4)/cyclic (< = N4), weight ratio | 3.65 | 4.07 | 6.72 | 6.26 | 6.87 | 7.52 | 5.87 | 6.61 | 5.71 | 5.24 |

TABLE XXIV

| | Example No. | | | | | | | | | |
|---|---|---|---|---|---|---|---|---|---|---|
| | 234 | 235 | 236 | 237 | 238 | 239 | 240 | 241 | 242 | 243 |
| Catalyst Type | X | X | X | X | X | X | X | X | X | X |
| Catalyst weight, gm | 83.01 | 83.01 | 83.01 | 83.01 | 83.01 | 83.01 | 83.01 | 83.01 | 83.01 | 83.01 |
| Pressure, psig | 603 | 596 | 599 | 599 | 601 | 597 | 603 | 603 | 602 | 603 |
| Temperature, °C. | 271 | 278 | 260 | 271 | 260 | 280 | 270 | 280 | 270 | 270 |
| Time on organics, hrs. | 99 | 104 | 123 | 128 | 147 | 152 | 171 | 176 | 195 | 206.75 |
| MEA SV, gmol/hr/kgcat | 3.13 | 3.33 | 3.26 | 3.20 | 3.18 | 3.07 | 2.34 | 2.47 | 2.21 | 2.35 |
| DETA/MEA mole ratio | 1.00 | 1.00 | 1.00 | 1.00 | 1.00 | 1.00 | 1.00 | 1.00 | 1.00 | 1.00 |
| NH3/MEA mole ratio | 5.97 | 5.97 | 5.97 | 5.97 | 5.97 | 5.97 | 5.97 | 5.97 | 5.97 | 5.97 |
| Crude product composition, wt % | | | | | | | | | | |
| EDA | 1.984 | 2.995 | 1.212 | 1.766 | 1.149 | 2.885 | 1.710 | 2.748 | 1.423 | 1.500 |
| MEA | 6.383 | 3.073 | 13.003 | 5.647 | 11.598 | 3.611 | 10.193 | 5.664 | 10.816 | 11.721 |
| PIP | 1.434 | 1.763 | 1.183 | 1.449 | 1.142 | 1.861 | 1.330 | 1.727 | 1.168 | 1.186 |
| DETA | 32.000 | 30.373 | 38.190 | 32.197 | 37.489 | 30.866 | 31.155 | 29.136 | 31.286 | 32.092 |
| AEEA | 0.501 | 0.186 | 1.296 | 0.439 | 1.265 | 0.220 | 0.847 | 0.403 | 0.987 | 1.078 |
| AEP | 1.636 | 2.525 | 1.050 | 1.785 | 1.133 | 2.307 | 1.524 | 2.483 | 1.278 | 1.244 |
| HEP | 0.000 | 0.000 | 0.000 | 0.000 | 0.000 | 0.000 | 0.000 | 0.000 | 0.000 | 0.000 |
| TAEA | 2.376 | 1.934 | 2.312 | 2.434 | 2.613 | 2.044 | 2.151 | 1.797 | 2.071 | 2.140 |
| 1-TETA | 12.940 | 12.003 | 11.840 | 13.576 | 13.452 | 12.217 | 10.663 | 10.795 | 10.563 | 10.796 |
| DAEP | 0.920 | 1.655 | 0.439 | 1.079 | 0.545 | 1.534 | 0.822 | 1.573 | 0.617 | 0.608 |
| PEEDA | 0.665 | 1.233 | 0.355 | 0.842 | 0.415 | 1.110 | 0.628 | 1.133 | 0.479 | 0.498 |
| DPE | 0.287 | 0.120 | 0.230 | 0.316 | 0.181 | 0.104 | 0.063 | 0.089 | 0.229 | 0.044 |
| AE-TAEA | 4.489 | 3.831 | 3.705 | 4.743 | 4.293 | 4.176 | 3.815 | 3.271 | 3.526 | 3.575 |
| 1-TEPA | 9.472 | 9.488 | 7.999 | 10.201 | 8.828 | 9.980 | 8.349 | 8.770 | 7.873 | 7.613 |
| AE-DAEP | 0.811 | 1.698 | 0.463 | 0.927 | 0.392 | 1.458 | 0.759 | 1.596 | 0.624 | 0.664 |
| AE-PEEDA | 0.148 | 0.223 | 0.123 | 0.165 | 0.067 | 0.216 | 0.150 | 0.128 | 0.081 | 0.078 |
| iAE-PEEDA | 0.000 | 0.000 | 0.000 | 0.000 | 0.000 | 0.000 | 0.000 | 0.000 | 0.000 | 0.000 |
| AE-DPE | 0.151 | 0.482 | 0.201 | 0.162 | 0.057 | 0.283 | 0.193 | 0.229 | 0.390 | 0.325 |
| BPEA | 0.149 | 0.853 | 0.178 | 0.215 | 0.057 | 0.232 | 0.082 | 0.655 | 0.601 | 0.569 |
| Others | 9.595 | 14.536 | 7.200 | 10.480 | 6.385 | 12.915 | 9.485 | 10.732 | 7.587 | 7.371 |
| MEA Conversion, % | 81.81 | 91.66 | 64.27 | 84.42 | 68.27 | 90.05 | 69.91 | 83.37 | 67.11 | 64.89 |
| DETA Conversion, % | 45.79 | 51.02 | 37.63 | 47.22 | 39.06 | 49.48 | 45.34 | 49.17 | 43.45 | 42.86 |
| Acyclic(N4), % | 89.11 | 82.25 | 93.25 | 87.74 | 93.37 | 83.84 | 89.43 | 81.83 | 90.51 | 91.84 |
| Acyclic(N5), % | 91.73 | 80.36 | 92.38 | 91.05 | 95.82 | 86.60 | 91.13 | 82.19 | 87.05 | 87.25 |
| $\Sigma(N5)/\Sigma(N4)$, weight ratio | 0.89 | 0.98 | 0.83 | 0.90 | 0.80 | 0.96 | 0.93 | 0.95 | 0.94 | 0.91 |
| Acyclic(N4)/cyclic (< = N4), weight ratio | 3.10 | 1.91 | 4.34 | 2.93 | 4.70 | 2.06 | 2.93 | 1.80 | 3.35 | 3.61 |

TABLE XXV

| | Example No. | | | | | | | | | | |
|---|---|---|---|---|---|---|---|---|---|---|---|
| | 244 | 245 | 246 | 247 | 248 | 249 | 250 | 251 | 252 | 253 | 254 |
| Catalyst Type | Y | Y | Y | Y | Y | Y | Y | Y | Y | Y | Y |
| Catalyst weight, gm | 84.9 | 84.9 | 84.9 | 84.9 | 82.11 | 84.9 | 84.9 | 84.9 | 84.9 | 84.9 | 84.9 |
| Pressure, psig | 604 | 604 | 604 | 604 | 602 | 604 | 602 | 603 | 600 | 600 | 600 |
| Temperature, °C. | 268 | 279 | 258 | 270 | 259 | 278 | 269 | 278 | 279 | 270 | 270 |
| Time on organics, hrs. | 24.5 | 27.75 | 47 | 52 | 71 | 76 | 95 | 99 | 118.5 | 139.8 | 141.5 |
| Duration of run, hrs. | 2 | 2 | 2 | 2 | 2 | 2 | 2 | 2 | 2 | 1 | 1 |
| MEA SV, gmol/hr/kgcat | 2.66 | 2.74 | 2.85 | 3.15 | 3.30 | 3.27 | 3.01 | 3.14 | 2.91 | 2.26 | 3.32 |
| DETA/MEA mole ratio | 1.00 | 1.00 | 1.00 | 1.00 | 1.00 | 1.00 | 1.00 | 1.00 | 1.00 | 1.00 | 1.00 |
| NH3/MEA mole ratio | 5.97 | 5.97 | 5.97 | 5.97 | 5.97 | 5.97 | 5.97 | 5.97 | 5.97 | 5.97 | 5.97 |
| Crude product composition, wt. % | | | | | | | | | | | |
| EDA | 0.261 | 0.356 | 0.244 | 0.282 | 0.226 | 0.267 | 0.193 | 0.300 | 0.276 | 0.137 | 0.175 |
| MEA | 32.096 | 31.884 | 33.649 | 33.262 | 34.748 | 33.604 | 35.331 | 34.218 | 33.615 | 33.551 | 33.298 |
| PIP | 0.012 | 0.017 | 0.009 | 0.013 | 0.000 | 0.013 | 0.000 | 0.014 | 0.015 | 0.021 | 0.015 |
| DETA | 53.034 | 52.823 | 55.550 | 57.167 | 58.160 | 57.340 | 58.631 | 55.561 | 55.690 | 57.452 | 57.445 |
| AEEA | 0.039 | 0.072 | 0.023 | 0.200 | 0.054 | 0.089 | 0.039 | 0.073 | 0.075 | 0.063 | 0.067 |
| AEP | 0.256 | 0.295 | 0.218 | 0.287 | 0.233 | 0.349 | 0.288 | 0.358 | 0.393 | 0.340 | 0.313 |
| HEP | 0.000 | 0.000 | 0.000 | 0.000 | 0.000 | 0.000 | 0.000 | 0.000 | 0.000 | 0.000 | 0.000 |
| TAEA | 0.091 | 0.098 | 0.112 | 0.187 | 0.094 | 0.150 | 0.077 | 0.475 | 0.111 | 0.137 | 0.171 |
| 1-TETA | 0.144 | 0.122 | 0.087 | 0.577 | 0.076 | 0.434 | 0.092 | 0.000 | 0.343 | 0.416 | 0.498 |
| DAEP | 0.024 | 0.031 | 0.016 | 0.056 | 0.000 | 0.021 | 0.000 | 0.067 | 0.044 | 0.030 | 0.027 |
| PEEDA | 0.194 | 0.074 | 0.183 | 0.037 | 0.211 | 0.152 | 0.077 | 0.082 | 0.052 | 0.036 | 0.034 |
| DPE | 0.069 | 0.085 | 0.053 | 0.027 | 0.094 | 0.065 | 0.061 | 0.044 | 0.047 | 0.082 | 0.055 |
| AE-TAEA | 0.000 | 0.037 | 0.000 | 0.045 | 0.000 | 0.085 | 0.052 | 0.000 | 0.000 | 0.000 | 0.000 |
| 1-TEPA | 0.147 | 0.062 | 0.000 | 0.047 | 0.000 | 0.068 | 0.000 | 0.036 | 0.061 | 0.000 | 0.071 |
| AE-DAEP | 0.000 | 0.000 | 0.000 | 0.000 | 0.024 | 0.060 | 0.027 | 0.091 | 0.114 | 0.028 | 0.000 |
| AE-PEEDA | 0.000 | 0.168 | 0.000 | 0.000 | 0.000 | 0.000 | 0.000 | 0.041 | 0.000 | 0.129 | 0.332 |
| iAe-PEEDA | 0.000 | 0.000 | 0.000 | 0.000 | 0.000 | 0.000 | 0.000 | 0.000 | 0.000 | 0.000 | 0.000 |

TABLE XXV-continued

| | Example No. | | | | | | | | | | |
|---|---|---|---|---|---|---|---|---|---|---|---|
| | 244 | 245 | 246 | 247 | 248 | 249 | 250 | 251 | 252 | 253 | 254 |
| AE-DPE | 0.000 | 0.039 | 0.000 | 0.053 | 0.035 | 0.162 | 0.044 | 0.031 | 0.092 | 0.099 | 0.097 |
| BPEA | 0.344 | 0.000 | 0.000 | 0.000 | 0.000 | 0.038 | 0.000 | 0.000 | 0.000 | 0.000 | 0.066 |
| Others | 1.659 | 2.389 | 1.815 | 2.931 | 1.866 | 3.482 | 2.698 | 3.109 | 3.712 | 2.859 | 2.756 |
| MEA Conversion, % | 3.06 | 3.91 | 2.16 | 6.89 | 3.11 | 7.25 | 3.34 | 5.38 | 6.32 | 7.15 | |
| DETA Conversion, % | 4.80 | 5.39 | 4.00 | 4.90 | 3.62 | 5.94 | 4.67 | 6.76 | 6.84 | 4.67 | 4.80 |
| Acyclic(N4), % | 44.95 | 53.51 | 44.02 | 86.49 | 35.80 | 71.03 | 54.99 | 71.17 | 76.09 | 78.86 | 85.22 |
| Acyclic(N5), % | 30.60 | 32.37 | 0.00 | 63.66 | 0.00 | 37.00 | 42.32 | 18.14 | 22.79 | 0.00 | 12.61 |
| Σ(N5)/Σ(N4), weight ratio | 0.92 | 0.75 | 0.00 | 0.16 | 0.13 | 0.50 | 0.40 | 0.30 | 0.45 | 0.36 | 0.72 |
| Acyclic(N4)/cyclic (< = N4), weight ratio | 0.42 | 0.44 | 0.41 | 1.82 | 0.32 | 0.97 | 0.40 | 0.84 | 0.82 | 1.09 | 1.51 |

TABLE XXVI

| | Example No. | | | | | | | | |
|---|---|---|---|---|---|---|---|---|---|
| | 255 | 256 | 257 | 258 | 259 | 260 | 261 | 262 | 263 |
| Catalyst Type | Z | Z | Z | Z | Z | Z | Z | Z | Z |
| Catalyst weight, gm | 45.68 | 45.68 | 45.68 | 45.68 | 45.68 | 45.68 | 45.68 | 45.68 | 45.68 |
| Presure, psig | 600 | 599 | 607 | 596 | 600 | 600 | 600 | 600 | 604 |
| Temperature, °C. | 269 | 279 | 260 | 270 | 270 | 259.6 | 279 | 270 | 280 |
| Time on organics, hrs. | 21 | 28 | 49 | 54 | 73.5 | 97.5 | 116 | 121 | 139 |
| Duration of run, hrs. | 2 | 2 | 2 | 2 | 2 | 2 | 2 | 2 | 2 |
| MEA SV, gmol/hr/kgcat | 5.74 | 5.87 | 5.23 | 6.08 | 3.67 | 3.99 | 2.29 | 4.68 | 5.77 |
| DETA/MEA mole ratio | 1.00 | 1.00 | 1.00 | 1.00 | 1.00 | 1.00 | 1.00 | 1.00 | 1.00 |
| NH3/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 4.265 | 6.176 | 3.433 | 3.075 | 3.788 | 3.313 | 4.920 | 3.283 | 4.944 |
| MEA | 5.796 | 3.354 | 10.079 | 7.161 | 8.233 | 12.638 | 5.859 | 8.995 | 7.083 |
| PIP | 2.117 | 2.992 | 1.443 | 1.595 | 1.901 | 1.711 | 3.037 | 1.662 | 2.421 |
| DETA | 28.085 | 21.574 | 33.585 | 28.671 | 28.468 | 35.387 | 22.837 | 31.649 | 26.907 |
| AEEA | 0.099 | 0.063 | 0.399 | 0.132 | 0.103 | 0.381 | 0.025 | 0.197 | 0.067 |
| AEP | 4.039 | 6.092 | 2.608 | 3.219 | 3.601 | 3.484 | 6.074 | 3.491 | 5.328 |
| HEP | 0.000 | 0.000 | 0.000 | 0.000 | 0.000 | 0.000 | 0.000 | 0.000 | 0.000 |
| TAEA | 3.229 | 1.766 | 3.587 | 3.434 | 2.819 | 2.812 | 1.936 | 3.537 | 2.241 |
| 1-TETA | 11.677 | 6.932 | 11.244 | 11.553 | 10.261 | 9.480 | 6.501 | 11.947 | 9.241 |
| DAEP | 2.387 | 3.807 | 1.767 | 1.907 | 1.991 | 1.653 | 4.685 | 2.133 | 3.545 |
| PEEDA | 1.116 | 1.889 | 0.855 | 0.890 | 0.958 | 0.844 | 2.020 | 0.989 | 1.785 |
| DPE | 0.174 | 0.405 | 0.101 | 0.132 | 0.139 | 0.113 | 0.580 | 0.315 | 0.262 |
| AE-TAEA | 5.681 | 3.174 | 5.080 | 5.634 | 4.681 | 3.953 | 2.940 | 5.597 | 3.677 |
| 1-TEPA | 8.664 | 6.535 | 6.720 | 7.856 | 6.920 | 5.613 | 3.566 | 7.833 | 6.809 |
| AE-DAEP | 0.935 | 0.738 | 0.803 | 0.708 | 0.722 | 0.579 | 0.757 | 0.823 | 1.937 |
| AE-PEEDA | 0.258 | 1.129 | 0.214 | 0.198 | 0.223 | 0.219 | 0.904 | 0.272 | 0.737 |
| iAE-PEEDA | 0.000 | 0.000 | 0.000 | 0.000 | 0.000 | 0.000 | 0.000 | 0.000 | 0.000 |
| AE-DPE | 0.055 | 0.256 | 0.050 | 0.037 | 0.048 | 0.047 | 0.237 | 0.050 | 0.057 |
| BPEA | 0.975 | 0.822 | 0.665 | 0.847 | 0.688 | 0.813 | 0.350 | 0.801 | 0.858 |
| Others | 8.808 | 15.412 | 6.548 | 7.053 | 6.595 | 5.262 | 19.371 | 7.036 | 12.602 |
| MEA Conversion, % | 84.08 | 90.34 | 72.07 | 79.20 | 75.41 | 64.40 | 83.73 | 75.68 | 81.06 |
| DETA Conversion, % | 54.16 | 63.06 | 44.68 | 50.52 | 49.47 | 40.75 | 62.31 | 49.14 | 57.23 |
| Acyclic(N4), % | 80.21 | 58.78 | 84.49 | 83.65 | 80.90 | 82.49 | 53.67 | 81.83 | 67.25 |
| Acyclic(N5), % | 86.58 | 76.69 | 87.20 | 88.29 | 87.35 | 85.23 | 74.32 | 87.34 | 74.50 |
| Σ(N5)/Σ(N4), weight ratio | 0.89 | 0.86 | 0.77 | 0.85 | 0.82 | 0.75 | 0.56 | 0.81 | 0.82 |
| Acyclic(N4)/cyclic (< = N4), weight ratio | 1.52 | 0.57 | 2.19 | 1.94 | 1.52 | 1.58 | 0.51 | 1.80 | 0.86 |

TABLE XXVII

| | Example No. | | | | | | | | |
|---|---|---|---|---|---|---|---|---|---|
| | 264 | 265 | 266 | 267 | 268 | 269 | 270 | 271 | 272 |
| Catalyst Type | AA | AA | AA | AA | AA | AA | AA | AA | AA |
| Catalyst weight, gm | 71.9 | 71.9 | 71.9 | 71.9 | 71.9 | 71.9 | 71.9 | 71.9 | 71.9 |
| Pressure, psig | 604 | 604 | 609 | 606 | 600 | 600 | 603 | 602 | 602 |
| Temperature, °C. | 270 | 282 | 258 | 272 | 260 | 280 | 273 | 281 | 272 |
| Time on organics, hrs. | 20.5 | 25.5 | 44.5 | 49.5 | 69.3 | 93.3 | 116.5 | 121.5 | 138.5 |
| Duration of run, hrs. | 2 | 2 | 2 | 2 | 2 | 2 | 2 | 2 | 2 |
| MEA SV, gmol/hr/kgcat | 3.36 | 3.46 | 3.43 | 3.50 | 3.55 | 3.41 | 3.50 | 3.67 | 3.49 |
| DETA/MEA mole ratio | 1.00 | 1.00 | 1.00 | 1.00 | 1.00 | 1.00 | 1.00 | 1.00 | 1.00 |
| NH3/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 0.654 | 1.188 | 0.880 | 0.700 | 0.372 | 1.659 | 0.860 | 1.397 | 0.841 |
| MEA | 26.367 | 22.170 | 24.384 | 27.194 | 29.909 | 21.016 | 27.518 | 23.168 | 26.560 |
| PIP | 0.812 | 1.365 | 0.882 | 0.772 | 0.000 | 1.711 | 0.812 | 1.473 | 0.833 |
| DETA | 51.269 | 45.690 | 48.835 | 51.840 | 55.476 | 43.224 | 51.818 | 46.089 | 52.002 |
| AEEA | 2.016 | 1.702 | 1.570 | 1.900 | 1.779 | 1.481 | 1.827 | 1.619 | 1.976 |
| AEP | 0.692 | 1.168 | 0.882 | 0.598 | 0.374 | 1.439 | 0.624 | 1.193 | 0.678 |
| HEP | 0.000 | 0.000 | 0.000 | 0.000 | 0.000 | 0.000 | 0.000 | 0.000 | 0.000 |

TABLE XXVII-continued

|  | Example No. | | | | | | | | |
|---|---|---|---|---|---|---|---|---|---|
|  | 264 | 265 | 266 | 267 | 268 | 269 | 270 | 271 | 272 |
| TAEA | 1.323 | 1.418 | 1.256 | 1.217 | 0.943 | 1.295 | 1.188 | 1.308 | 1.216 |
| 1-TETA | 7.359 | 8.836 | 7.770 | 6.793 | 5.048 | 8.777 | 6.824 | 8.418 | 7.095 |
| DEAP | 0.163 | 0.347 | 0.300 | 0.112 | 0.071 | 0.485 | 0.130 | 0.370 | 0.143 |
| PEEDA | 0.160 | 0.417 | 0.373 | 0.120 | 0.076 | 0.528 | 0.145 | 0.432 | 0.153 |
| DPE | 0.046 | 0.069 | 0.061 | 0.042 | 0.025 | 0.114 | 0.046 | 0.034 | 0.050 |
| AE-TAEA | 1.015 | 1.431 | 1.257 | 0.863 | 0.494 | 1.551 | 0.865 | 1.450 | 0.923 |
| 1-TEPA | 2.990 | 4.899 | 4.463 | 2.563 | 1.436 | 5.428 | 2.725 | 4.968 | 2.853 |
| AE-DAEP | 0.242 | 0.305 | 0.326 | 0.045 | 0.074 | 0.345 | 0.060 | 0.264 | 0.065 |
| AE-PEEDA | 0.106 | 0.077 | 0.079 | 0.000 | 0.000 | 0.094 | 0.062 | 0.187 | 0.038 |
| iAE-PEEDA | 0.000 | 0.000 | 0.000 | 0.000 | 0.000 | 0.000 | 0.000 | 0.000 | 0.000 |
| AE-DPE | 0.000 | 0.000 | 0.000 | 0.000 | 0.000 | 0.000 | 0.000 | 0.000 | 0.000 |
| BPEA | 0.031 | 0.052 | 0.046 | 0.123 | 0.080 | 0.273 | 0.127 | 0.070 | 0.049 |
| Others | 1.656 | 3.848 | 3.595 | 1.579 | 0.943 | 4.584 | 1.700 | 3.838 | 1.946 |
| MEA Conversion, % | 29.19 | 40.08 | 35.05 | 26.39 | 18.82 | 42.93 | 26.19 | 38.13 | 28.97 |
| DETA Conversion, % | 18.17 | 26.61 | 22.69 | 16.60 | 10.51 | 30.24 | 17.39 | 26.86 | 17.35 |
| Acyclic(N4), % | 95.92 | 92.50 | 92.49 | 96.69 | 97.20 | 89.50 | 96.15 | 92.08 | 96.01 |
| Acyclic(N5), % | 91.34 | 93.59 | 92.70 | 95.32 | 92.60 | 90.73 | 93.52 | 92.49 | 96.12 |
| $\Sigma(N5)/\Sigma(N4)$, weight ratio | 0.48 | 0.61 | 0.63 | 0.43 | 0.34 | 0.68 | 0.46 | 0.66 | 0.45 |
| Acyclic(N4)/cyclic (< = N4), weight ratio | 4.64 | 3.05 | 3.61 | 4.87 | 10.96 | 2.33 | 4.56 | 2.78 | 4.48 |

TABLE XXVIII

|  | Example No. | | | | | | | | |
|---|---|---|---|---|---|---|---|---|---|
|  | 273 | 274 | 275 | 276 | 277 | 278 | 279 | 280 | 281 |
| Catalyst Type | BB | BB | BB | BB | BB | BB | BB | BB | BB |
| Catalyst weight, gm | 47.15 | 47.15 | 47.15 | 47.15 | 47.15 | 47.15 | 47.15 | 47.15 | 47.15 |
| Pressure, psig | 603 | 604 | 597 | 593 | 600 | 609 | 600 | 601 | 601 |
| Temperature, °C. | 270 | 281 | 258 | 272 | 280 | 273 | 281 | 272 | 272 |
| Time on organics, hrs. | 20.5 | 25.5 | 44.5 | 49.5 | 93.3 | 116.5 | 121.5 | 138.5 | 143.25 |
| Duration of run, hrs. | 2 | 2 | 2 | 2 | 1 | 2 | 2 | 2 | 2 |
| MEA SV, gmol/hr/kgcat | 5.62 | 5.50 | 6.38 | 5.77 | 5.23 | 4.89 | 6.12 | 5.90 | 6.45 |
| DETA/MEA mole ratio | 1.00 | 1.00 | 1.00 | 1.00 | 1.00 | 1.00 | 1.00 | 1.00 | 1.00 |
| NH$_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 4.112 | 6.049 | 3.022 | 3.411 | 5.550 | 3.212 | 4.820 | 3.441 | 2.793 |
| MEA | 3.993 | 1.805 | 8.392 | 5.992 | 2.263 | 7.178 | 3.892 | 6.533 | 8.131 |
| PIP | 2.090 | 2.764 | 1.493 | 1.835 | 2.928 | 1.697 | 2.331 | 1.856 | 1.521 |
| DETA | 26.200 | 19.797 | 30.716 | 29.072 | 19.595 | 30.928 | 25.883 | 27.399 | 32.697 |
| AEEA | 0.105 | 0.029 | 0.466 | 0.193 | 0.059 | 0.257 | 0.082 | 0.253 | 0.337 |
| AEP | 3.816 | 5.459 | 2.748 | 3.098 | 5.455 | 2.783 | 4.440 | 3.792 | 2.683 |
| HEP | 0.000 | 0.000 | 0.000 | 0.000 | 0.000 | 0.000 | 0.000 | 0.000 | 0.000 |
| TAEA | 3.246 | 1.816 | 3.371 | 3.690 | 1.636 | 3.637 | 1.211 | 3.154 | 3.657 |
| 1-TETA | 12.248 | 7.991 | 11.446 | 12.890 | 7.985 | 12.535 | 9.944 | 11.428 | 12.152 |
| DAEP | 2.327 | 3.836 | 1.908 | 1.821 | 3.625 | 1.607 | 2.852 | 2.506 | 1.457 |
| PEEDA | 1.147 | 2.001 | 1.029 | 0.933 | 1.998 | 0.854 | 1.534 | 1.473 | 0.870 |
| DPE | 0.205 | 0.259 | 0.072 | 0.159 | 0.343 | 0.212 | 0.287 | 0.292 | 0.199 |
| AE-TAEA | 5.841 | 3.653 | 5.224 | 6.189 | 3.051 | 6.144 | 4.652 | 4.999 | 5.566 |
| 1-TEPA | 9.617 | 6.279 | 8.218 | 9.146 | 4.846 | 8.976 | 8.411 | 7.886 | 8.254 |
| AE-DAEP | 1.138 | 2.226 | 1.270 | 0.744 | 0.976 | 0.196 | 0.637 | 0.703 | 0.282 |
| AE-PEEDA | 0.133 | 0.798 | 0.566 | 0.032 | 1.236 | 0.237 | 0.789 | 0.817 | 0.091 |
| iAE-PEEDA | 0.000 | 0.000 | 0.000 | 0.000 | 0.000 | 0.000 | 0.000 | 0.000 | 0.000 |
| AE-DPE | 0.198 | 0.335 | 0.262 | 0.062 | 0.124 | 0.064 | 0.176 | 0.106 | 0.138 |
| BPEA | 0.494 | 1.127 | 0.826 | 0.441 | 0.203 | 1.316 | 1.347 | 1.252 | 1.167 |
| Others | 13.100 | 17.605 | 11.271 | 10.063 | 19.810 | 9.418 | 16.332 | 12.551 | 9.604 |
| MEA Conversion, % | 89.29 | 94.88 | 77.77 | 83.74 | 93.38 | 80.79 | 89.55 | 82.50 | 78.25 |
| DETA Conversion, % | 58.24 | 66.61 | 51.64 | 53.13 | 65.93 | 50.81 | 58.69 | 56.38 | 48.01 |
| Acyclic(N4), % | 80.81 | 61.67 | 83.12 | 85.06 | 61.73 | 85.82 | 70.48 | 77.35 | 86.22 |
| Acyclic(N5), % | 88.73 | 68.89 | 82.14 | 92.30 | 75.68 | 89.29 | 81.59 | 81.74 | 89.16 |
| $\Sigma(N5)/\Sigma(N4)$, weight ratio | 0.91 | 0.91 | 0.92 | 0.85 | 0.67 | 0.90 | 1.01 | 0.84 | 0.85 |
| Acyclic(N4)/cyclic (< = N4), weight ratio | 1.62 | 0.68 | 2.04 | 2.11 | 0.67 | 2.26 | 0.97 | 1.47 | 2.35 |

|  | Example No. | | | | | | | | |
|---|---|---|---|---|---|---|---|---|---|
|  | 282 | 283 | 284 | 285 | 286 | 287 | 288 | 289 | 290 |
| Catalyst Type | BB | BB | BB | BB | BB | BB | BB | BB | BB |
| Catalyst weight, gm | 47.15 | 47.15 | 47.15 | 47.15 | 47.15 | 47.15 | 47.15 | 47.15 | 47.15 |
| Pressure, psig | 603 | 602 | 601 | 602 | 596 | 599 | 600 | 600 | 600 |
| Temperature, °C. | 270 | 280 | 260 | 269 | 259 | 269 | 269 | 279.6 | 268 |
| Time on organics, hrs. | 22.5 | 27.5 | 46.5 | 51.5 | 70.5 | 99.5 | 120 | 143 | 169.5 |
| Duration of run, hrs. | 2 | 2 | 2 | 2 | 2 | 2 | 2 | 2 | 2 |
| MEA SV, gmol/hr/kgcat | 4.97 | 4.30 | 3.85 | 2.94 | 0.75 | 5.31 | 5.03 | 4.80 | 3.32 |
| DETA/MEA mole ratio | 1.00 | 1.00 | 1.00 | 1.00 | 1.00 | 1.00 | 1.00 | 1.00 | 1.00 |
| NH$_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |

TABLE XXVIII-continued

| | | | | | | | | | |
|---|---|---|---|---|---|---|---|---|---|
| EDA | 2.967 | 4.366 | 4.440 | 2.967 | 4.460 | 1.952 | 3.142 | 4.055 | 2.453 |
| MEA | 9.344 | 4.942 | 4.115 | 7.299 | 4.769 | 11.879 | 10.054 | 6.454 | 12.691 |
| PIP | 1.511 | 2.037 | 2.043 | 1.452 | 2.132 | 1.272 | 1.700 | 2.182 | 1.366 |
| DETA | 31.637 | 26.975 | 25.016 | 30.734 | 25.564 | 38.106 | 32.444 | 26.800 | 38.319 |
| AEEA | 0.424 | 0.162 | 0.130 | 0.465 | 0.229 | 0.767 | 0.506 | 0.183 | 0.649 |
| AEP | 2.464 | 3.612 | 3.730 | 2.436 | 3.835 | 1.957 | 3.105 | 4.023 | 2.028 |
| HEP | 0.000 | 0.000 | 0.000 | 0.000 | 0.000 | 0.000 | 0.000 | 0.000 | 0.000 |
| TAEA | 3.232 | 3.170 | 3.039 | 4.030 | 3.514 | 3.588 | 2.814 | 2.467 | 3.544 |
| 1-TETA | 11.069 | 12.118 | 12.039 | 13.420 | 13.075 | 11.521 | 10.058 | 9.825 | 12.044 |
| DAEP | 1.231 | 2.138 | 2.332 | 1.243 | 2.045 | 0.861 | 1.515 | 2.269 | 0.889 |
| PEEDA | 0.679 | 1.195 | 1.326 | 0.704 | 1.131 | 0.508 | 0.922 | 1.458 | 0.524 |
| DPE | 0.187 | 0.300 | 0.338 | 0.255 | 0.476 | 0.141 | 0.254 | 0.309 | 0.124 |
| AE-TAEA | 5.103 | 5.422 | 5.331 | 6.126 | 5.933 | 4.797 | 4.017 | 4.146 | 4.610 |
| 1-TEPA | 7.681 | 9.105 | 9.262 | 8.935 | 9.548 | 6.845 | 6.630 | 7.426 | 6.884 |
| AE-DAEP | 0.028 | 0.438 | 0.477 | 0.260 | 0.377 | 0.367 | 0.846 | 1.348 | 0.370 |
| AE-PEEDA | 0.645 | 0.119 | 0.143 | 0.119 | 0.141 | 0.096 | 0.119 | 0.616 | 0.106 |
| iAE-PEEDA | 0.000 | 0.000 | 0.000 | 0.000 | 0.000 | 0.000 | 0.000 | 0.000 | 0.000 |
| AE-DPE | 0.437 | 0.190 | 0.276 | 0.126 | 0.050 | 0.048 | 0.028 | 0.092 | 0.029 |
| BPEA | 0.997 | 0.316 | 0.321 | 0.381 | 0.328 | 0.593 | 0.605 | 0.273 | 0.533 |
| Others | 6.554 | 13.105 | 14.254 | 9.326 | 11.795 | 5.441 | 9.162 | 13.636 | 4.287 |
| MEA Conversion, % | 73.30 | 86.63 | 88.77 | 80.18 | 87.07 | 67.40 | 71.78 | 82.09 | 65.35 |
| DETA Conversion, % | 46.27 | 56.62 | 59.43 | 50.41 | 58.82 | 37.84 | 45.87 | 55.81 | 37.82 |
| Acyclic(N4), % | 87.21 | 80.80 | 79.05 | 88.79 | 81.96 | 90.91 | 82.71 | 75.29 | 91.03 |
| Acyclic(N5), % | 85.85 | 93.18 | 92.31 | 94.44 | 94.53 | 91.34 | 86.95 | 83.25 | 91.71 |
| Σ(N5)/Σ(N4), weight ratio | 0.91 | 0.82 | 0.83 | 0.81 | 0.81 | 0.77 | 0.79 | 0.85 | 0.73 |
| Acyclic(N4)/cyclic (< = N4), weight ratio | 2.36 | 1.65 | 1.54 | 2.87 | 1.72 | 3.19 | 1.72 | 1.20 | 3.16 |

TABLE XXIX

| | Example No. | | | | | | | | | |
|---|---|---|---|---|---|---|---|---|---|---|
| | 291 | 292 | 293 | 294 | 295 | 296 | 297 | 298 | 299 | 300 |
| Catalyst Type | CC | CC | CC | CC | CC | CC | CC | CC | CC | CC |
| Catalyst weight, gm | 76.68 | 76.68 | 76.68 | 76.68 | 76.68 | 76.68 | 76.68 | 76.68 | 76.68 | 76.68 |
| Pressure, psig | 603 | 603 | 604 | 604 | 604 | 604 | 602 | 600 | 600 | 603 |
| Temperature, °C. | 270 | 260 | 269 | 259 | 280 | 280 | 269 | 269 | 279.6 | 268 |
| Time on organics, hrs. | 22.5 | 46.5 | 51.5 | 70.5 | 75.5 | 94.5 | 99.5 | 120 | 143 | 169.5 |
| Duration of run, hrs. | 2 | 2 | 2 | 2 | 2 | 2 | 2 | 2 | 2 | 2 |
| MEA SV, gmol/hr/kgcat | 3.56 | 3.18 | 3.05 | 2.39 | 2.57 | 2.86 | 3.10 | 2.58 | 2.14 | 2.10 |
| DETA/MEA mole ratio | 1.00 | 1.00 | 1.00 | 1.00 | 1.00 | 1.00 | 1.00 | 1.00 | 1.00 | 1.00 |
| NH3/MEA mole ratio | 5.97 | 5.97 | 5.97 | 5.97 | 5.97 | 5.97 | 5.97 | 5.97 | 5.97 | 5.97 |
| Crude product composition, wt. % | | | | | | | | | | |
| EDA | 1.048 | 1.891 | 1.635 | 0.886 | 2.023 | 1.862 | 0.964 | 1.307 | 2.134 | 1.598 |
| MEA | 15.586 | 7.180 | 13.602 | 16.846 | 6.993 | 5.180 | 14.419 | 11.949 | 4.391 | 10.047 |
| PIP | 0.813 | 1.493 | 1.323 | 0.749 | 1.617 | 1.560 | 1.056 | 1.181 | 1.690 | 1.287 |
| DETA | 41.901 | 34.342 | 39.594 | 43.641 | 34.966 | 31.278 | 43.144 | 40.674 | 33.084 | 40.233 |
| AEEA | 1.865 | 0.611 | 1.010 | 2.381 | 0.717 | 0.512 | 2.061 | 1.865 | 0.489 | 1.972 |
| AEP | 0.823 | 1.517 | 1.156 | 0.704 | 1.562 | 1.651 | 0.963 | 1.108 | 1.845 | 1.344 |
| HEP | 0.000 | 0.000 | 0.000 | 0.000 | 0.000 | 0.000 | 0.000 | 0.000 | 0.000 | 0.000 |
| TAEA | 2.659 | 2.739 | 2.487 | 2.206 | 2.576 | 2.486 | 2.470 | 2.584 | 2.664 | 2.778 |
| 1-TETA | 11.989 | 13.676 | 12.245 | 10.267 | 13.010 | 12.812 | 11.950 | 12.589 | 14.102 | 14.021 |
| DAEP | 0.232 | 0.654 | 0.419 | 0.182 | 0.622 | 0.734 | 0.275 | 0.343 | 0.814 | 0.472 |
| PEEDA | 0.217 | 0.518 | 0.333 | 0.166 | 0.508 | 0.588 | 0.265 | 0.328 | 0.634 | 0.384 |
| DPE | 0.109 | 0.083 | 0.058 | 0.039 | 0.100 | 0.095 | 0.052 | 0.061 | 0.132 | 0.148 |
| AE-TAEA | 3.022 | 4.382 | 3.814 | 1.989 | 4.314 | 4.182 | 3.097 | 3.397 | 4.800 | 3.528 |
| 1-TEPA | 5.378 | 8.807 | 6.947 | 3.856 | 8.743 | 8.887 | 6.071 | 6.875 | 10.097 | 7.285 |
| AE-DAEP | 0.000 | 0.169 | 0.298 | 0.077 | 0.555 | 0.161 | 0.332 | 0.223 | 0.191 | 0.386 |
| AE-PEEDA | 0.213 | 0.106 | 0.056 | 0.030 | 0.119 | 0.104 | 0.049 | 0.039 | 0.121 | 0.060 |
| iAE-PEEDA | 0.000 | 0.000 | 0.000 | 0.000 | 0.000 | 0.000 | 0.000 | 0.000 | 0.000 | 0.000 |
| AE-DPE | 0.429 | 0.057 | 0.000 | 0.000 | 0.079 | 0.078 | 0.045 | 0.000 | 0.109 | 0.086 |
| BPEA | 0.423 | 0.255 | 0.529 | 0.212 | 0.715 | 0.986 | 0.407 | 0.447 | 1.153 | 0.657 |
| Others | 2.432 | 7.971 | 4.837 | 2.430 | 8.651 | 8.353 | 4.000 | 4.471 | 9.150 | 4.134 |
| MEA Conversion, % | 55.76 | 79.54 | 62.13 | 50.35 | 80.43 | 84.46 | 60.32 | 66.53 | 87.79 | 72.35 |
| DETA Conversion, % | 29.31 | 41.82 | 34.48 | 23.55 | 41.85 | 44.25 | 29.45 | 32.30 | 45.34 | 34.20 |
| Acyclic(N4), % | 96.35 | 92.90 | 94.78 | 96.99 | 92.69 | 91.52 | 96.06 | 95.40 | 91.39 | 94.36 |
| Acyclic(N5), % | 88.75 | 95.74 | 92.28 | 94.82 | 89.89 | 90.77 | 91.66 | 93.55 | 90.44 | 90.10 |
| Σ(N5)/Σ(N4), weight ratio | 0.62 | 0.78 | 0.74 | 0.48 | 0.86 | 0.86 | 0.67 | 0.69 | 0.90 | 0.67 |
| Acyclic(N4)/cyclic (< = N4), weight ratio | 6.67 | 3.85 | 4.48 | 6.78 | 3.54 | 3.31 | 5.53 | 5.02 | 3.28 | 4.62 |

TABLE XXX

| | Example No. | | | | | | | | | |
|---|---|---|---|---|---|---|---|---|---|---|
| | 301 | 302 | 303 | 304 | 305 | 306 | 307 | 308 | 309 | 310 |
| Catalyst Type | DD | DD | DD | DD | DD | DD | DD | DD | DD | DD |
| Catalyst weight, gm | 78.75 | 78.75 | 78.75 | 78.75 | 78.75 | 78.75 | 78.75 | 78.75 | 78.75 | 78.75 |
| Pressure, psig | 598 | 598 | 599 | 598 | 600 | 600 | 598 | 600 | 598 | 600 |

TABLE XXX-continued

| | Example No. | | | | | | | | | |
|---|---|---|---|---|---|---|---|---|---|---|
| | 301 | 302 | 303 | 304 | 305 | 306 | 307 | 308 | 309 | 310 |
| Temperature, °C. | 269 | 279 | 260 | 270 | 270 | 259.6 | 279 | 270 | 280 | 270 |
| Time on organics, hrs. | 21 | 28 | 49 | 54 | 73.5 | 97.5 | 116 | 121 | 139 | 144 |
| Duration of run, hrs. | 2 | 2 | 2 | 2 | 2 | 2 | 2 | 2 | 2 | 2 |
| MEA SV, gmol/hr/kgcat | 2.92 | 2.87 | 3.06 | 2.85 | 2.60 | 2.98 | 2.80 | 2.99 | 2.81 | 2.96 |
| DETA/MEA mole ratio | 1.00 | 1.00 | 1.00 | 1.00 | 1.00 | 1.00 | 1.00 | 1.00 | 1.00 | 1.00 |
| $NH_3$/MEA mole ratio | 5.97 | 5.97 | 5.97 | 5.97 | 5.97 | 5.97 | 5.97 | 5.97 | 5.97 | 5.97 |
| Crude product composition, wt. % | | | | | | | | | | |
| EDA | 1.555 | 1.668 | 1.004 | 0.978 | 0.998 | 0.533 | 2.192 | 1.116 | 1.691 | 0.974 |
| MEA | 15.132 | 10.654 | 18.325 | 16.432 | 15.110 | 22.024 | 8.483 | 16.234 | 7.965 | 14.943 |
| PIP | 0.978 | 1.343 | 0.749 | 0.856 | 0.926 | 0.581 | 1.662 | 1.112 | 1.577 | 1.057 |
| DETA | 41.054 | 38.593 | 44.607 | 43.072 | 41.241 | 51.032 | 35.320 | 45.272 | 36.976 | 44.374 |
| AEEA | 1.683 | 0.873 | 1.751 | 1.997 | 1.834 | 2.629 | 0.512 | 1.883 | 0.650 | 1.955 |
| AEP | 1.101 | 1.347 | 0.771 | 0.821 | 0.835 | 0.570 | 1.905 | 0.982 | 1.561 | 1.000 |
| HEP | 0.000 | 0.000 | 0.000 | 0.000 | 0.000 | 0.000 | 0.000 | 0.000 | 0.000 | 0.000 |
| TAEA | 2.712 | 2.489 | 2.232 | 2.241 | 2.226 | 1.861 | 2.166 | 2.390 | 2.589 | 2.511 |
| 1-TETA | 11.777 | 11.906 | 10.383 | 10.387 | 10.429 | 8.845 | 11.724 | 11.589 | 13.232 | 12.136 |
| DAEP | 0.423 | 0.486 | 0.280 | 0.215 | 0.235 | 0.126 | 0.995 | 0.266 | 0.649 | 0.285 |
| PEEDA | 0.327 | 0.415 | 0.253 | 0.183 | 0.199 | 0.101 | 0.736 | 0.226 | 0.512 | 0.249 |
| DPE | 0.088 | 0.183 | 0.098 | 0.092 | 0.091 | 0.057 | 0.262 | 0.089 | 0.219 | 0.098 |
| AE-TAEA | 3.411 | 3.691 | 2.918 | 2.501 | 2.621 | 1.429 | 3.662 | 3.017 | 4.503 | 3.121 |
| 1-TEPA | 6.041 | 6.960 | 5.789 | 4.661 | 4.999 | 2.823 | 8.129 | 5.730 | 9.114 | 6.079 |
| AE-DAEP | 0.397 | 0.339 | 0.351 | 0.199 | 0.231 | 0.053 | 1.154 | 0.242 | 0.570 | 0.278 |
| AE-PEEDA | 0.058 | 0.077 | 0.059 | 0.052 | 0.032 | 0.000 | 0.223 | 0.032 | 0.163 | 0.042 |
| iAE-PEEDA | 0.000 | 0.000 | 0.000 | 0.000 | 0.000 | 0.000 | 0.000 | 0.000 | 0.000 | 0.000 |
| AE-DPE | 0.052 | 0.153 | 0.049 | 0.072 | 0.067 | 0.000 | 0.208 | 0.077 | 0.070 | 0.097 |
| BPEA | 0.695 | 0.772 | 0.603 | 0.425 | 0.457 | 0.177 | 0.094 | 0.547 | 0.803 | 0.556 |
| Others | 4.145 | 4.991 | 3.687 | 2.354 | 2.636 | 1.310 | 9.047 | 2.757 | 7.406 | 3.016 |
| MEA Conversion, % | 58.37 | 69.49 | 50.38 | 52.25 | 55.02 | 39.54 | 76.37 | 56.07 | 78.27 | 59.37 |
| DETA Conversion, % | 32.88 | 34.31 | 28.22 | 25.62 | 27.04 | 16.74 | 41.52 | 27.19 | 40.06 | 28.29 |
| Acyclic(N4), % | 94.53 | 92.99 | 95.23 | 96.26 | 96.01 | 97.42 | 87.46 | 96.01 | 91.98 | 95.86 |
| Acyclic(N5), % | 88.72 | 88.82 | 89.13 | 90.54 | 90.63 | 94.86 | 87.54 | 90.69 | 89.45 | 90.43 |
| $\Sigma(N5)/\Sigma(N4)$, weight ratio | 0.70 | 0.77 | 0.74 | 0.60 | 0.64 | 0.41 | 0.85 | 0.66 | 0.88 | 0.67 |
| Acyclic(N4)/cyclic ($<$ = N4), weight ratio | 4.97 | 3.81 | 5.86 | 5.83 | 5.53 | 7.46 | 2.50 | 5.23 | 3.50 | 5.45 |

TABLE XXXI

| | Example No. | | | | | | | | | |
|---|---|---|---|---|---|---|---|---|---|---|
| | 311 | 312 | 313 | 314 | 315 | 316 | 317 | 318 | 319 | 320 |
| Catalyst Type | EE | EE | EE | EE | EE | EE | EE | EE | EE | EE |
| Catalyst weight, gm | 76.67 | 76.67 | 76.67 | 76.67 | 76.67 | 76.67 | 76.67 | 76.67 | 76.67 | 76.67 |
| Pressure, psig | 599 | 599 | 609 | 599 | 600 | 598 | 596 | 598 | 600 | 599 |
| Temperature, °C. | 270 | 280 | 260 | 269 | 259 | 280 | 280 | 269 | 269 | 268 |
| Time on organics, hrs. | 22.5 | 27.5 | 46.5 | 51.5 | 70.5 | 75.5 | 94.5 | 99.5 | 120 | 169.5 |
| Duration of run, hrs. | 2 | 2 | 2 | 2 | 2 | 2 | 2 | 2 | 2 | 2 |
| MEA SV, gmol/hr/kgcat | 3.05 | 3.06 | 2.79 | 3.10 | 3.07 | 3.13 | 3.03 | 3.01 | 3.05 | 3.15 |
| DETA/MEA mole ratio | 1.00 | 1.00 | 1.00 | 1.00 | 1.00 | 1.00 | 1.00 | 1.00 | 1.00 | 1.00 |
| $NH_3$/MEA mole ratio | 5.97 | 5.97 | 5.97 | 5.97 | 5.97 | 5.97 | 5.97 | 5.97 | 5.97 | 5.97 |
| Crude product composition, wt. % | | | | | | | | | | |
| EDA | 1.520 | 2.437 | 2.447 | 1.228 | 1.029 | 2.414 | 2.547 | 1.320 | 1.437 | 1.242 |
| MEA | 14.652 | 8.505 | 6.424 | 13.718 | 18.262 | 7.632 | 6.416 | 14.174 | 12.516 | 13.988 |
| PIP | 1.110 | 1.615 | 1.625 | 1.089 | 0.811 | 1.685 | 1.788 | 1.154 | 1.228 | 1.100 |
| DETA | 39.856 | 33.953 | 30.620 | 42.604 | 44.433 | 34.076 | 32.533 | 40.980 | 39.040 | 42.773 |
| AEEA | 1.060 | 0.447 | 0.314 | 1.855 | 1.945 | 0.437 | 0.334 | 1.170 | 1.071 | 1.048 |
| AEP | 1.075 | 1.737 | 1.834 | 1.025 | 0.733 | 1.846 | 2.086 | 1.119 | 1.173 | 1.187 |
| HEP | 0.000 | 0.000 | 0.000 | 0.000 | 0.000 | 0.000 | 0.000 | 0.000 | 0.000 | 0.000 |
| TAEA | 2.436 | 2.526 | 2.311 | 2.830 | 2.495 | 2.424 | 2.285 | 2.594 | 2.614 | 2.592 |
| 1-TETA | 11.953 | 13.615 | 12.962 | 13.423 | 11.709 | 13.253 | 12.977 | 12.761 | 12.998 | 14.044 |
| DAEP | 0.316 | 0.845 | 0.960 | 0.297 | 0.197 | 0.863 | 1.049 | 0.408 | 0.461 | 0.325 |
| PEEDA | 0.271 | 0.647 | 0.738 | 0.284 | 0.177 | 0.663 | 0.796 | 0.337 | 0.392 | 0.267 |
| DPE | 0.114 | 0.099 | 0.099 | 0.049 | 0.040 | 0.099 | 0.102 | 0.071 | 0.074 | 0.052 |
| AE-TAEA | 3.524 | 4.505 | 4.333 | 3.359 | 2.704 | 4.359 | 4.387 | 3.710 | 3.897 | 3.401 |
| 1-TEPA | 6.384 | 9.138 | 9.198 | 6.628 | 5.017 | 9.080 | 9.494 | 6.780 | 7.415 | 6.586 |
| AE-DAEP | 0.000 | 0.248 | 0.279 | 0.314 | 0.207 | 0.679 | 0.267 | 0.307 | 0.269 | 0.300 |
| AE-PEEDA | 0.229 | 0.135 | 0.140 | 0.042 | 0.063 | 0.126 | 0.123 | 0.032 | 0.057 | 0.054 |
| iAE-PEEDA | 0.000 | 0.000 | 0.000 | 0.000 | 0.000 | 0.000 | 0.000 | 0.000 | 0.000 | 0.000 |
| AE-DPE | 0.553 | 0.191 | 0.210 | 0.000 | 0.000 | 0.052 | 0.093 | 0.000 | 0.033 | 0.000 |
| BPEA | 0.522 | 0.338 | 0.365 | 0.442 | 0.300 | 0.794 | 0.831 | 0.530 | 0.577 | 0.532 |
| Others | 3.075 | 9.229 | 10.383 | 4.003 | 2.618 | 9.258 | 10.540 | 4.653 | 5.267 | 2.788 |
| MEA Conversion, % | 58.39 | 76.75 | 81.53 | 63.00 | 49.80 | 79.10 | 82.29 | 61.34 | 65.43 | 62.89 |
| DETA Conversion, % | 32.73 | 44.85 | 47.68 | 31.70 | 27.42 | 44.55 | 46.62 | 33.56 | 35.92 | 30.74 |
| Acyclic(N4), % | 95.36 | 91.03 | 89.48 | 96.26 | 97.17 | 90.61 | 88.68 | 94.65 | 94.40 | 96.27 |
| Acyclic(N5), % | 88.37 | 93.73 | 93.16 | 92.61 | 93.12 | 89.06 | 91.35 | 92.35 | 92.35 | 91.85 |
| $\Sigma(N5)/\Sigma(N4)$, weight ratio | 0.74 | 0.82 | 0.85 | 0.64 | 0.57 | 0.87 | 0.88 | 0.70 | 0.74 | 0.63 |
| Acyclic(N4)/cyclic | 4.99 | 3.27 | 2.91 | 5.92 | 7.25 | 3.04 | 2.62 | 4.97 | 4.69 | 5.68 |

TABLE XXXI-continued

| | Example No. | | | | | | | | | |
|---|---|---|---|---|---|---|---|---|---|---|
| | 311 | 312 | 313 | 314 | 315 | 316 | 317 | 318 | 319 | 320 |
| (< = N4), weight ratio | | | | | | | | | | |

TABLE XXXII

| | Example No. | | | | | | | | |
|---|---|---|---|---|---|---|---|---|---|
| | 321 | 322 | 323 | 324 | 325 | 326 | 327 | 328 | 329 |
| Catalyst Type | FF | FF | FF | FF | FF | FF | FF | FF | FF |
| Catalyst weight, gm | 81.02 | 81.02 | 81.02 | 81.02 | 81.02 | 81.02 | 81.02 | 81.02 | 81.02 |
| Pressure, psig | 598 | 598 | 598 | 598 | 598 | 598 | 600 | 600 | 600 |
| Temperature, °C. | 258 | 270 | 259 | 278 | 269 | 278 | 279 | 270 | 270 |
| Time on organics, hrs. | 47 | 52 | 71 | 76 | 95 | 99 | 118.5 | 139.8 | 141.5 |
| Duration of run, hrs. | 2 | 2 | 2 | 2 | 2 | 2 | 2 | 1 | 1 |
| MEA SV, gmol/hr/kgcat | 2.59 | 2.69 | 2.76 | 2.69 | 2.62 | 2.89 | 2.50 | 2.61 | 2.85 |
| DETA/MEA mole ratio | 1.00 | 1.00 | 1.00 | 1.00 | 1.00 | 1.00 | 1.00 | 1.00 | 1.00 |
| $NH_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 1.431 | 1.466 | 0.836 | 2.026 | 1.389 | 1.898 | 3.937 | 1.319 | 1.270 |
| MEA | 20.803 | 15.928 | 21.573 | 8.455 | 13.153 | 5.684 | 3.430 | 11.218 | 12.033 |
| PIP | 0.619 | 0.793 | 0.421 | 1.275 | 0.987 | 1.265 | 2.108 | 1.046 | 0.995 |
| DETA | 41.470 | 40.511 | 47.612 | 36.072 | 40.931 | 31.699 | 26.932 | 37.630 | 37.696 |
| AEEA | 1.655 | 2.044 | 2.654 | 0.991 | 1.869 | 0.695 | 0.297 | 1.784 | 1.787 |
| AEP | 1.227 | 0.888 | 0.525 | 1.430 | 1.026 | 1.530 | 3.019 | 1.099 | 0.994 |
| HEP | 0.000 | 0.000 | 0.000 | 0.000 | 0.000 | 0.000 | 0.000 | 0.000 | 0.000 |
| TAEA | 1.792 | 2.202 | 1.893 | 2.343 | 2.432 | 2.392 | 1.670 | 2.598 | 2.308 |
| l-TETA | 9.207 | 11.790 | 9.627 | 13.461 | 13.115 | 13.772 | 11.582 | 14.083 | 12.425 |
| DAEP | 0.616 | 0.258 | 0.103 | 0.671 | 0.399 | 0.778 | 1.863 | 0.456 | 0.383 |
| PEEDA | 0.451 | 0.211 | 0.071 | 0.519 | 0.296 | 0.575 | 1.351 | 0.364 | 0.034 |
| DPE | 0.029 | 0.076 | 0.066 | 0.203 | 0.107 | 0.217 | 0.107 | 0.049 | 0.059 |
| AE-TAEA | 2.172 | 3.076 | 1.560 | 4.364 | 3.434 | 4.598 | 0.163 | 3.800 | 3.588 |
| l-TEPA | 4.520 | 5.662 | 2.989 | 9.213 | 7.036 | 9.871 | 9.389 | 7.945 | 7.481 |
| AE-DAEP | 0.421 | 0.185 | 0.102 | 0.530 | 0.226 | 6.503 | 0.543 | 0.066 | 0.134 |
| AE-PEEDA | 0.029 | 0.036 | 0.030 | 0.116 | 0.035 | 0.100 | 0.907 | 0.030 | 0.098 |
| iAE-PEEDA | 0.000 | 0.000 | 0.000 | 0.000 | 0.000 | 0.000 | 0.000 | 0.000 | 0.000 |
| AE-DPE | 0.023 | 0.000 | 0.000 | 0.223 | 0.050 | 0.264 | 0.161 | 0.068 | 0.138 |
| BPEA | 0.388 | 0.045 | 0.026 | 0.807 | 0.056 | 1.316 | 1.078 | 0.184 | 0.220 |
| Others | 3.269 | 3.950 | 1.862 | 7.511 | 4.907 | 4.583 | 16.344 | 5.932 | 7.028 |
| MEA Conversion, % | 40.86 | 54.65 | 39.37 | 76.88 | 63.86 | 84.34 | 90.23 | 68.77 | 66.03 |
| DETA Conversion, % | 29.93 | 31.45 | 20.47 | 41.38 | 33.16 | 48.10 | 54.39 | 37.75 | 36.75 |
| Acyclic(N4), % | 90.94 | 96.29 | 97.95 | 91.90 | 95.09 | 91.15 | 79.97 | 95.05 | 96.87 |
| Acyclic(N5), % | 88.61 | 97.05 | 96.63 | 89.01 | 96.62 | 63.88 | 78.03 | 97.13 | 94.95 |
| $\Sigma(N5)/\Sigma(N4)$, weight ratio | 0.62 | 0.62 | 0.40 | 0.89 | 0.66 | 1.28 | 0.74 | 0.69 | 0.77 |
| Acyclic(N4)/cyclic (< = N4), weight ratio | 3.74 | 6.29 | 9.71 | 3.86 | 5.52 | 3.70 | 1.57 | 5.53 | 5.98 |

TABLE XXXIII

| | Example No. | | | | | | | | |
|---|---|---|---|---|---|---|---|---|---|
| | 330 | 331 | 332 | 333 | 334 | 335 | 336 | 337 | 338 |
| Catalyst Type | GG | GG | GG | GG | GG | GG | GG | GG | GG |
| Catalyst weight, gm | 68 | 68 | 68 | 68 | 68 | 68 | 68 | 68 | 68 |
| Pressure, psig | 606 | 599 | 602 | 606 | 593 | 593 | 601 | 600 | 600 |
| Temperature, °C. | 270 | 270 | 280 | 260 | 270 | 260 | 280 | 280 | 270 |
| Time on organics, hrs. | 7 | 26 | 30.5 | 50 | 55 | 74 | 79 | 98.8 | 123 |
| Duration of run, hrs. | 2 | 2 | 1 | 2 | 2 | 2 | 2 | 2 | 2 |
| MEA SV, gmol/hr/kgcat | 3.97 | 3.90 | 3.93 | 3.98 | 3.96 | 3.94 | 3.97 | 3.93 | 3.85 |
| DETA/MEA mole ratio | 1.00 | 1.00 | 1.00 | 1.00 | 1.00 | 1.00 | 1.00 | 1.00 | 1.00 |
| $NH_3$/MEA mole ratio | 5.97 | 5.97 | 5.97 | 5.97 | 5.97 | 5.97 | 5.97 | 5.97 | 5.97 |
| Crude product composition, wt % | | | | | | | | | |
| EDA | 0.750 | 0.869 | 1.269 | 0.502 | 0.696 | 1.589 | 1.188 | 1.273 | 0.810 |
| MEA | 14.139 | 13.058 | 7.841 | 19.884 | 13.962 | 19.078 | 8.661 | 6.995 | 13.582 |
| PIP | 0.946 | 1.041 | 1.264 | 0.614 | 0.883 | 0.667 | 1.206 | 1.218 | 0.953 |
| DETA | 42.338 | 40.333 | 34.679 | 47.727 | 41.491 | 46.874 | 37.218 | 33.635 | 40.430 |
| AEEA | 1.641 | 1.480 | 0.679 | 2.213 | 1.609 | 2.241 | 0.609 | 0.617 | 1.541 |
| AEP | 0.987 | 1.041 | 1.527 | 0.599 | 0.913 | 0.603 | 1.467 | 1.500 | 0.961 |
| HEP | 0.000 | 0.000 | 0.000 | 0.000 | 0.000 | 0.000 | 0.000 | 0.000 | 0.000 |
| TAEA | 2.657 | 2.786 | 2.699 | 2.233 | 2.513 | 2.246 | 2.703 | 2.625 | 2.555 |
| l-TETA | 12.825 | 13.469 | 13.932 | 10.488 | 12.891 | 10.468 | 13.856 | 13.911 | 12.446 |
| DAEP | 0.340 | 0.387 | 0.763 | 0.170 | 0.305 | 0.165 | 0.693 | 0.770 | 0.335 |
| PEEDA | 0.302 | 0.336 | 0.601 | 0.150 | 0.277 | 0.146 | 0.549 | 0.605 | 0.284 |
| DPE | 0.132 | 0.150 | 0.301 | 0.094 | 0.099 | 0.099 | 0.088 | 0.118 | 0.077 |
| AE-TAEA | 3.574 | 3.998 | 4.830 | 2.253 | 3.538 | 2.309 | 4.432 | 4.606 | 3.500 |
| l-TEPA | 7.216 | 7.943 | 9.991 | 4.612 | 7.184 | 4.724 | 9.147 | 9.831 | 7.304 |
| AE-DAEP | 0.088 | 0.082 | 0.204 | 0.154 | 0.134 | 0.064 | 0.601 | 0.879 | 0.328 |
| AE-PEEDA | 0.155 | 0.158 | 0.380 | 0.028 | 0.223 | 0.074 | 0.067 | 0.125 | 0.039 |
| iAE-PEEDA | 0.000 | 0.000 | 0.000 | 0.000 | 0.000 | 0.000 | 0.000 | 0.000 | 0.000 |

TABLE XXXIII-continued

| | | | | | | | | | |
|---|---|---|---|---|---|---|---|---|---|
| AE-DPE | 0.038 | 0.067 | 0.403 | 0.056 | 0.248 | 0.075 | 0.078 | 0.313 | 0.048 |
| BPEA | 0.508 | 0.179 | 1.040 | 0.229 | 0.611 | 0.231 | 0.804 | 0.839 | 0.472 |
| Others | 5.025 | 5.875 | 9.178 | 2.946 | 5.812 | 3.348 | 7.734 | 8.939 | 4.826 |
| MEA conversion, % | 62.09 | 64.96 | 79.02 | 46.40 | 62.51 | 48.13 | 76.57 | 80.72 | 62.33 |
| DETA conversion, % | 32.54 | 35.67 | 44.85 | 23.54 | 33.79 | 24.26 | 40.15 | 44.90 | 33.36 |
| Acyclic(N4), wt. % | 95.24 | 94.91 | 90.90 | 96.85 | 95.77 | 96.87 | 92.56 | 91.71 | 95.57 |
| Acyclic(N5), wt. % | 93.19 | 96.09 | 87.98 | 93.64 | 89.81 | 94.07 | 89.76 | 87.00 | 92.42 |
| Σ(N5)/Σ(N4), weight ratio | 0.71 | 0.73 | 0.92 | 0.56 | 0.74 | 0.57 | 0.85 | 0.92 | 0.74 |
| Acyclic(N4)/cyclic (< = N4), weight ratio | 5.72 | 5.50 | 3.73 | 7.82 | 6.22 | 7.57 | 4.14 | 3.93 | 5.75 |

| | Example No. | | | | | | | | | |
|---|---|---|---|---|---|---|---|---|---|---|
| | 339 | 340 | 341 | 342 | 343 | 344 | 345 | 346 | 347 | 348 |
| Catalyst Type | GG | GG | GG | GG | GG | GG | GG | GG | GG | GG |
| Catalyst weight, gm | 68 | 68 | 68 | 68 | 68 | 68 | 68 | 68 | 68 | 68 |
| Pressure, psig | 596 | 598 | 602 | 603 | 602 | 602 | 603 | 603 | 603 | 603 |
| Temperature, °C. | 271 | 282 | 260 | 270 | 260 | 281 | 272 | 280 | 272 | 271 |
| Time on organics, hrs. | 158 | 163 | 182 | 187 | 206 | 211 | 272 | 235 | 254 | 257.5 |
| Duration of run, hrs. | 2 | 2 | 2 | 2 | 83.7 | 2 | 2 | 2 | 2 | 2 |
| MEA SV, gmol/hr/kgcat | 3.92 | 3.89 | 3.99 | 3.83 | 0.09 | 3.85 | 3.80 | 3.88 | 3.86 | 4.03 |
| DETA/MEA mole ratio | 1.00 | 1.00 | 1.00 | 1.00 | 1.00 | 1.00 | 1.00 | 1.00 | 1.00 | 1.00 |
| NH3/MEA mole ratio | 5.97 | 5.97 | 5.97 | 5.97 | 5.97 | 5.97 | 5.97 | 5.97 | 5.97 | 5.97 |
| Crude product composition, wt. % | | | | | | | | | | |
| EDA | 1.086 | 1.518 | 0.564 | 0.960 | 0.630 | 1.769 | 1.921 | 2.220 | 1.641 | 1.650 |
| MEA | 13.203 | 6.960 | 18.056 | 12.558 | 17.829 | 6.838 | 12.002 | 5.827 | 11.663 | 13.072 |
| PIP | 1.186 | 1.446 | 0.765 | 1.101 | 0.770 | 1.362 | 1.263 | 1.380 | 1.178 | 1.205 |
| DETA | 40.181 | 35.494 | 45.781 | 40.874 | 44.267 | 34.368 | 39.115 | 30.652 | 38.907 | 40.441 |
| AEEA | 1.261 | 0.505 | 2.117 | 1.385 | 2.108 | 0.517 | 1.158 | 0.441 | 1.197 | 1.308 |
| AEP | 1.136 | 1.798 | 0.738 | 1.161 | 0.699 | 1.725 | 1.205 | 1.595 | 1.179 | 1.119 |
| HEP | 0.000 | 0.000 | 0.000 | 0.000 | 0.000 | 0.000 | 0.000 | 0.000 | 0.000 | 0.000 |
| TAEA | 2.661 | 2.671 | 2.384 | 2.732 | 2.320 | 2.531 | 2.548 | 2.402 | 2.575 | 2.513 |
| 1-TETA | 13.232 | 14.206 | 11.386 | 13.549 | 11.117 | 13.437 | 12.752 | 13.162 | 12.893 | 12.524 |
| DAEP | 0.452 | 0.939 | 0.225 | 0.438 | 0.196 | 0.889 | 0.485 | 0.981 | 0.469 | 0.410 |
| PEEDA | 0.372 | 0.692 | 0.187 | 0.361 | 0.175 | 0.670 | 0.383 | 0.728 | 0.375 | 0.335 |
| DPE | 0.076 | 0.107 | 0.056 | 0.091 | 0.033 | 0.111 | 0.077 | 0.133 | 0.082 | 0.076 |
| AE-TAEA | 4.013 | 4.667 | 2.669 | 3.990 | 2.705 | 4.603 | 4.023 | 4.890 | 3.878 | 3.770 |
| 1-TEPA | 8.152 | 9.680 | 5.588 | 8.225 | 5.696 | 9.840 | 8.145 | 10.433 | 8.054 | 7.706 |
| AE-DAEP | 0.401 | 0.783 | 0.156 | 0.382 | 0.201 | 0.171 | 0.377 | 0.235 | 0.379 | 0.324 |
| AE-PEEDA | 0.047 | 0.080 | 0.028 | 0.051 | 0.028 | 0.114 | 0.042 | 0.161 | 0.048 | 0.037 |
| iAE-PEEDA | 0.000 | 0.000 | 0.000 | 0.000 | 0.000 | 0.000 | 0.000 | 0.000 | 0.000 | 0.000 |
| AE-DPE | 0.057 | 0.105 | 0.046 | 0.043 | 0.036 | 0.053 | 0.049 | 0.000 | 0.047 | 0.046 |
| BPEA | 0.607 | 0.902 | 0.324 | 0.630 | 0.311 | 0.897 | 0.644 | 1.020 | 0.619 | 0.582 |
| Others | 5.537 | 8.116 | 3.310 | 5.711 | 3.339 | 10.005 | 5.502 | 13.484 | 5.564 | 5.184 |
| MEA conversion, % | 64.77 | 81.20 | 51.33 | 66.74 | 50.94 | 81.35 | 67.32 | 84.30 | 67.93 | 64.52 |
| DETA conversion, % | 36.28 | 43.03 | 26.65 | 35.67 | 27.60 | 44.30 | 36.70 | 50.93 | 36.43 | 34.77 |
| Acyclic(N4), wt. % | 94.64 | 90.67 | 96.72 | 94.81 | 97.08 | 90.53 | 94.19 | 89.41 | 94.35 | 94.83 |
| Acyclic(N5), wt. % | 91.63 | 88.47 | 93.71 | 91.70 | 93.58 | 92.12 | 91.63 | 87.84 | 91.61 | 92.07 |
| Σ(N5)/Σ(N4), weight ratio | 0.79 | 0.87 | 0.62 | 0.78 | 0.65 | 0.89 | 0.82 | 1.00 | 0.79 | 0.79 |
| Acyclic(N4)/cyclic(< = N4), weight ratio | 4.93 | 3.39 | 6.99 | 5.16 | 7.17 | 3.36 | 4.48 | 3.23 | 4.71 | 4.78 |

| | Example No. | | | | | | | | |
|---|---|---|---|---|---|---|---|---|---|
| | 349 | 350 | 351 | 352 | 353 | 354 | 355 | 356 | 357 |
| Catalyst Type | GG | GG | GG | GG | GG | GG | GG | GG | GG |
| Catalyst weight, gm | 67.2 | 67.2 | 67.2 | 67.2 | 67.2 | 67.2 | 67.2 | 67.2 | 67.2 |
| Pressure, psig | 600 | 600 | 600 | 600 | 600 | 600 | 600 | 600 | 600 |
| Temperature, °C. | 267.7 | 267.9 | 278 | 257.8 | 269.6 | 259.3 | 279.3 | 269.8 | 270.1 |
| Time on organics, hrs. | 4 | 6.5 | 28.5 | 47.5 | 52.5 | 71 | 76.5 | 96.5 | 99 |
| Duration of run, hrs. | 2 | 2 | 2 | 2 | 2 | 2 | 2 | 2 | 2 |
| MEA SV, gmol/hr/kgcat | 4.59 | 4.81 | 4.66 | 4.74 | 4.80 | 4.79 | 4.46 | 4.63 | 4.60 |
| DETA/MEA mole ratio | 1.00 | 1.00 | 1.00 | 1.00 | 1.00 | 1.00 | 1.00 | 1.00 | 1.00 |
| NH3/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 0.515 | 0.541 | 1.593 | 0.567 | 0.832 | 0.445 | 1.675 | 0.932 | 0.995 |
| MEA | 23.588 | 25.727 | 18.012 | 26.580 | 21.992 | 27.189 | 13.854 | 20.859 | 20.291 |
| PIP | 0.888 | 1.118 | 1.953 | 1.009 | 1.390 | 0.957 | 1.810 | 1.493 | 1.486 |
| DETA | 54.811 | 54.100 | 50.845 | 55.433 | 53.042 | 56.685 | 51.796 | 53.039 | 51.623 |
| AEEA | 0.344 | 0.802 | 0.233 | 0.360 | 0.208 | 0.377 | 0.150 | 0.478 | 0.210 |
| AEP | 0.883 | 0.858 | 1.884 | 0.856 | 1.352 | 0.775 | 2.177 | 1.423 | 1.423 |
| HEP | 0.000 | 0.000 | 0.000 | 0.000 | 0.000 | 0.000 | 0.000 | 0.000 | 0.000 |
| TAEA | 1.618 | 1.490 | 1.878 | 1.474 | 1.695 | 1.397 | 1.977 | 1.858 | 1.955 |
| 1-TETA | 7.964 | 7.269 | 9.198 | 6.586 | 8.327 | 6.490 | 9.962 | 8.880 | 10.270 |
| DAEP | 0.114 | 0.093 | 0.645 | 0.301 | 0.154 | 0.207 | 0.692 | 0.412 | 0.178 |
| PEEDA | 0.081 | 0.064 | 0.387 | 0.144 | 0.104 | 0.117 | 0.359 | 0.162 | 0.125 |
| DPE | 0.000 | 0.000 | 0.000 | 0.000 | 0.000 | 0.000 | 0.000 | 0.000 | 0.000 |
| AE-TAEA | 0.000 | 0.088 | 0.246 | 0.000 | 0.102 | 0.000 | 1.894 | 0.109 | 0.000 |
| 1-TEPA | 0.664 | 0.704 | 1.555 | 0.500 | 0.975 | 0.246 | 3.556 | 1.157 | 1.321 |
| AE-DAEP | 0.000 | 0.223 | 0.372 | 0.000 | 0.000 | 0.000 | 0.114 | 0.133 | 0.326 |
| AE-PEEDA | 0.000 | 0.000 | 0.099 | 0.000 | 0.175 | 0.000 | 0.075 | 0.000 | 0.069 |
| iAE-PEEDA | 0.000 | 0.000 | 0.000 | 0.000 | 0.000 | 0.000 | 0.000 | 0.000 | 0.000 |

TABLE XXXIII-continued

| | | | | | | | | | |
|---|---|---|---|---|---|---|---|---|---|
| AE-DPE | 0.168 | 0.000 | 0.059 | 0.000 | 0.423 | 0.000 | 0.000 | 0.083 | 0.512 |
| BPEA | 0.000 | 0.000 | 0.000 | 0.000 | 0.000 | 0.000 | 0.000 | 0.000 | 0.000 |
| Others | 1.532 | 0.963 | 2.990 | 1.492 | 2.047 | 0.994 | 0.880 | 1.861 | 2.579 |
| MEA conversion, % | 34.18 | 28.60 | 49.97 | 27.10 | 38.81 | 25.75 | 61.46 | 42.13 | 44.20 |
| DETA conversion, % | 9.11 | 10.77 | 16.06 | 9.64 | 12.29 | 7.99 | 14.37 | 12.55 | 15.64 |
| Acyclic(N4), wt. % | 98.01 | 98.23 | 91.48 | 94.77 | 97.49 | 96.05 | 91.91 | 94.93 | 97.59 |
| Acyclic(N5), wt. % | 79.79 | 78.07 | 77.26 | 100.00 | 64.30 | 100.00 | 96.64 | 85.40 | 59.30 |
| Σ(N5)/Σ(N4), weight ratio | 0.09 | 0.11 | 0.19 | 0.06 | 0.16 | 0.03 | 0.43 | 0.13 | 0.18 |
| Acyclic(N4)/cyclic(< = N4), weight ratio | 4.87 | 4.11 | 2.27 | 3.49 | 3.34 | 3.83 | 2.37 | 3.08 | 3.81 |

TABLE XXXIV

| | Example No. | | | | | | | | |
|---|---|---|---|---|---|---|---|---|---|
| | 358 | 359 | 360 | 361 | 362 | 363 | 364 | 365 | 366 |
| Catalyst Type | HH | HH | HH | HH | HH | HH | HH | HH | HH |
| Catalyst weight, gm | 69.34 | 69.34 | 69.34 | 69.34 | 69.34 | 69.34 | 69.34 | 69.34 | 69.34 |
| Pressure, psig | 604 | 603 | 603 | 604 | 604 | 603 | 603 | 600 | 600 |
| Temperature, °C. | 270 | 270 | 280 | 260 | 270 | 260 | 280 | 280 | 270 |
| Time on organics, hrs. | 7 | 26 | 30.5 | 50 | 55 | 74 | 79 | 98.8 | 123 |
| Duration of run, hrs. | 2 | 2 | 1 | 2 | 2 | 2 | 2 | 2 | 2 |
| MEA SV, gmol/hr/kgcat | 4.33 | 4.26 | 4.21 | 4.20 | 4.33 | 4.20 | 4.17 | 4.26 | 4.16 |
| DETA/MEA mole ratio | 1.00 | 1.00 | 1.00 | 1.00 | 1.00 | 1.00 | 1.00 | 1.00 | 1.00 |
| NH$_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 0.805 | 1.034 | 1.662 | 0.510 | 0.908 | 0.544 | 1.363 | 2.077 | 0.963 |
| MEA | 14.316 | 13.747 | 10.093 | 20.646 | 15.418 | 19.410 | 8.991 | 9.550 | 15.047 |
| PIP | 0.832 | 0.927 | 1.260 | 0.542 | 0.841 | 0.555 | 1.085 | 1.325 | 0.906 |
| DETA | 41.647 | 40.641 | 36.709 | 48.819 | 43.537 | 47.902 | 35.150 | 32.997 | 41.105 |
| AEEA | 1.392 | 1.332 | 0.661 | 2.056 | 1.526 | 2.142 | 0.718 | 0.580 | 1.445 |
| AEP | 0.990 | 1.057 | 1.455 | 0.554 | 0.915 | 0.588 | 1.336 | 1.810 | 0.927 |
| HEP | 0.000 | 0.000 | 0.000 | 0.000 | 0.000 | 0.000 | 0.000 | 0.000 | 0.000 |
| TAEA | 2.980 | 2.906 | 2.683 | 2.272 | 2.709 | 2.329 | 2.593 | 1.994 | 2.443 |
| 1-TETA | 13.276 | 13.074 | 12.859 | 9.750 | 12.028 | 10.013 | 12.850 | 10.946 | 11.547 |
| DAEP | 0.416 | 0.470 | 0.726 | 0.152 | 0.358 | 0.171 | 0.754 | 1.270 | 0.373 |
| PEEDA | 0.321 | 0.347 | 0.527 | 0.130 | 0.270 | 0.147 | 0.531 | 0.858 | 0.292 |
| DPE | 0.151 | 0.167 | 0.208 | 0.055 | 0.159 | 0.073 | 0.126 | 0.164 | 0.196 |
| AE-TAEA | 4.148 | 4.074 | 4.997 | 2.219 | 3.441 | 2.254 | 4.357 | 3.447 | 3.193 |
| 1-TEPA | 7.057 | 7.074 | 8.378 | 3.718 | 6.209 | 3.871 | 8.283 | 7.231 | 6.092 |
| AE-DAEP | 0.081 | 0.074 | 0.124 | 0.145 | 0.075 | 0.247 | 1.053 | 1.912 | 0.489 |
| AE-PEEDA | 0.148 | 0.141 | 0.238 | 0.027 | 0.117 | 0.067 | 0.154 | 0.294 | 0.065 |
| iAE-PEEDA | 0.000 | 0.000 | 0.000 | 0.000 | 0.000 | 0.000 | 0.000 | 0.000 | 0.000 |
| AE-DPE | 0.051 | 0.069 | 0.286 | 0.266 | 0.175 | 0.261 | 0.309 | 0.130 | 0.070 |
| BPEA | 0.582 | 0.570 | 0.800 | 0.207 | 0.479 | 0.205 | 0.737 | 0.613 | 0.415 |
| Others | 5.099 | 5.415 | 7.215 | 2.423 | 4.615 | 2.781 | 8.931 | 12.620 | 4.609 |
| MEA conversion, % | 61.90 | 63.00 | 72.52 | 43.91 | 58.54 | 46.90 | 75.19 | 73.83 | 57.94 |
| DETA conversion, % | 34.13 | 35.00 | 40.60 | 21.18 | 30.42 | 22.12 | 42.36 | 46.26 | 31.71 |
| Acyclic(N4), wt. % | 94.82 | 94.20 | 91.41 | 97.28 | 94.93 | 96.93 | 91.63 | 84.95 | 94.20 |
| Acyclic(N5), wt. % | 92.86 | 92.88 | 90.23 | 90.21 | 91.94 | 88.71 | 84.88 | 78.36 | 89.93 |
| Σ(N5)/Σ(N4), weight ratio | 0.70 | 0.71 | 0.87 | 0.53 | 0.68 | 0.54 | 0.88 | 0.89 | 0.70 |
| Acyclic(N4)/cyclic(< = N4), weight ratio | 6.00 | 5.38 | 3.72 | 8.39 | 5.80 | 8.05 | 4.03 | 2.38 | 5.19 |

| | Example No. | | | | | | | | |
|---|---|---|---|---|---|---|---|---|---|
| | 367 | 368 | 369 | 370 | 371 | 372 | 373 | 374 | 375 | 376 |
| Catalyst Type | HH | HH | HH | HH | HH | HH | HH | HH | HH | HH |
| Catalyst weight, gm | 69.34 | 69.34 | 69.34 | 69.34 | 69.34 | 69.34 | 69.34 | 69.34 | 69.34 | 69.34 |
| Pressure, psig | 603 | 604 | 603 | 604 | 603 | 604 | 604 | 604 | 603 | 604 |
| Temperature, °C. | 271 | 282 | 260 | 270 | 260 | 281 | 272 | 280 | 272 | 271 |
| Time on organics, hrs. | 158 | 163 | 182 | 187 | 206 | 211 | 272 | 235 | 254 | 257.5 |
| Duration of run, hrs. | 2 | 2 | 2 | 2 | 2 | 2 | 2 | 2 | 2 | 2 |
| MEA SV, gmol/hr/kgcat | 4.01 | 4.31 | 4.28 | 4.05 | 4.11 | 4.41 | 4.13 | 4.11 | 4.22 | 4.43 |
| DETA/MEA mole ratio | 1.00 | 1.00 | 1.00 | 1.00 | 1.00 | 1.00 | 1.00 | 1.00 | 1.00 | 1.00 |
| NH$_3$/MEA mole ratio | 5.97 | 5.97 | 5.97 | 5.97 | 5.97 | 5.97 | 5.97 | 5.97 | 5.97 | 5.97 |
| Crude product composition, wt. % | | | | | | | | | | |
| EDA | 1.212 | 1.778 | 0.757 | 0.980 | 0.861 | 2.156 | 1.946 | 2.350 | 1.794 | 1.594 |
| MEA | 12.554 | 9.298 | 20.034 | 13.105 | 18.882 | 8.720 | 12.941 | 7.170 | 13.118 | 13.362 |
| PIP | 1.009 | 1.387 | 0.734 | 0.962 | 0.794 | 1.385 | 1.150 | 1.343 | 1.147 | 1.045 |
| DETA | 37.117 | 36.552 | 46.016 | 38.892 | 44.565 | 34.824 | 39.610 | 33.663 | 39.912 | 38.851 |
| AEEA | 1.046 | 0.554 | 1.888 | 1.280 | 1.745 | 0.521 | 1.185 | 0.478 | 1.195 | 1.279 |
| AEP | 1.212 | 1.598 | 0.679 | 0.976 | 0.784 | 1.518 | 1.109 | 1.669 | 1.094 | 1.015 |
| HEP | 0.000 | 0.000 | 0.000 | 0.000 | 0.000 | 0.000 | 0.000 | 0.000 | 0.000 | 0.000 |
| TAEA | 2.311 | 2.549 | 2.223 | 2.513 | 2.187 | 2.296 | 2.546 | 2.452 | 2.458 | 2.496 |
| 1-TETA | 11.703 | 13.076 | 10.211 | 11.973 | 10.178 | 12.160 | 12.466 | 13.106 | 12.081 | 12.149 |
| DAEP | 0.669 | 0.839 | 0.209 | 0.394 | 0.335 | 0.916 | 0.518 | 1.012 | 0.454 | 0.423 |
| PEEDA | 0.476 | 0.594 | 0.174 | 0.318 | 0.240 | 0.634 | 0.377 | 0.766 | 0.348 | 0.321 |
| DPE | 0.112 | 0.468 | 0.072 | 0.186 | 0.150 | 0.127 | 0.092 | 0.123 | 0.079 | 0.072 |
| AE-TAEA | 3.397 | 4.484 | 2.580 | 3.922 | 2.727 | 4.290 | 3.863 | 4.417 | 3.624 | 3.540 |
| 1-TEPA | 7.003 | 8.450 | 5.015 | 7.390 | 5.407 | 8.840 | 7.583 | 9.218 | 7.097 | 6.990 |
| AE-DAEP | 0.928 | 0.694 | 0.198 | 0.427 | 0.351 | 0.189 | 0.411 | 0.892 | 0.342 | 0.038 |

TABLE XXXIV-continued

| | | | | | | | | | | |
|---|---|---|---|---|---|---|---|---|---|---|
| AE-PEEDA | 0.153 | 0.085 | 0.045 | 0.079 | 0.059 | 0.132 | 0.052 | 0.135 | 0.036 | 0.038 |
| iAE-PEEDA | 0.000 | 0.000 | 0.000 | 0.000 | 0.000 | 0.000 | 0.000 | 0.000 | 0.000 | 0.000 |
| AE-DPE | 0.287 | 0.093 | 0.051 | 0.166 | 0.042 | 0.411 | 0.073 | 0.390 | 0.091 | 0.061 |
| BPEA | 0.510 | 0.761 | 0.054 | 0.563 | 0.330 | 0.822 | 0.597 | 0.843 | 0.577 | 0.535 |
| Others | 7.302 | 7.358 | 3.390 | 6.493 | 3.912 | 10.339 | 5.881 | 9.704 | 5.473 | 5.321 |
| Conversion, % | 64.82 | 74.69 | 45.65 | 63.83 | 48.59 | 76.20 | 64.94 | 80.41 | 63.82 | 62.91 |
| DETA conversion, % | 38.19 | 40.86 | 25.81 | 36.20 | 27.88 | 43.50 | 36.22 | 45.35 | 34.58 | 34.25 |
| Acyclic(N4), wt. % | 91.77 | 89.15 | 96.47 | 94.16 | 94.46 | 89.61 | 93.83 | 89.12 | 94.28 | 94.72 |
| Acyclic(N5), wt. % | 84.70 | 88.79 | 95.62 | 90.16 | 91.23 | 89.42 | 91.00 | 85.78 | 91.11 | 91.63 |
| Σ(N5)/Σ(N4), weight ratio | 0.80 | 0.83 | 0.62 | 0.82 | 0.68 | 0.91 | 0.79 | 0.91 | 0.76 | 0.74 |
| Acyclic(N4)/cyclic(< = N4), weight ratio | 4.03 | 3.20 | 6.65 | 5.11 | 5.37 | 3.16 | 4.63 | 3.17 | 4.66 | 5.09 |

TABLE XXXV

| | Example No. | | | | | | | | |
|---|---|---|---|---|---|---|---|---|---|
| | 377 | 378 | 379 | 380 | 381 | 382 | 383 | 384 | 385 |
| Catalyst Type | II | II | II | II | II | II | II | II | II |
| Catalyst weight, gm | 70.6 | 70.6 | 70.6 | 70.6 | 70.6 | 70.6 | 70.6 | 70.6 | 70.6 |
| Pressure, psig | 600 | 600 | 600 | 600 | 600 | 600 | 600 | 600 | 600 |
| Temperature, °C. | 267.7 | 267.9 | 278 | 257.8 | 269.6 | 259.3 | 279.3 | 269.8 | 270.1 |
| Time on organics, hrs. | 4 | 6.5 | 30.5 | 49.5 | 54.5 | 73 | 78.5 | 98 | 101 |
| Duration of run, hrs. | 2 | 2 | 2 | 2 | 2 | 2 | 2 | 2 | 2 |
| MEA SV, gmol/hr/kgcat | 4.23 | 4.29 | 4.10 | 4.04 | 4.14 | 4.15 | 3.89 | 3.94 | 3.95 |
| DETA/MEA mole ratio | 1.00 | 1.00 | 1.00 | 1.00 | 1.00 | 1.00 | 1.00 | 1.00 | 1.00 |
| NH₃/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 0.162 | 0.169 | 0.783 | 0.192 | 0.397 | 0.176 | 1.073 | 0.529 | 0.553 |
| MEA | 29.144 | 31.908 | 24.483 | 32.053 | 27.952 | 31.487 | 22.456 | 25.861 | 26.009 |
| PIP | 0.349 | 0.340 | 1.209 | 0.251 | 0.651 | 0.248 | 1.406 | 0.768 | 0.760 |
| DETA | 59.742 | 58.534 | 56.565 | 58.955 | 59.279 | 59.506 | 54.811 | 57.648 | 57.364 |
| AEEA | 0.310 | 0.929 | 0.200 | 0.321 | 0.342 | 0.351 | 0.776 | 0.366 | 0.370 |
| AEP | 0.544 | 0.498 | 1.287 | 0.436 | 0.711 | 0.471 | 1.454 | 0.793 | 0.801 |
| HEP | 0.000 | 0.000 | 0.000 | 0.000 | 0.000 | 0.000 | 0.000 | 0.000 | 0.000 |
| TAEA | 0.578 | 0.706 | 0.873 | 0.618 | 0.733 | 0.669 | 1.573 | 0.874 | 1.310 |
| 1-TETA | 4.153 | 2.968 | 6.200 | 2.623 | 4.926 | 2.835 | 6.907 | 5.628 | 5.841 |
| DAEP | 0.177 | 0.175 | 0.342 | 0.144 | 0.238 | 0.180 | 0.520 | 0.239 | 0.184 |
| PEEDA | 0.076 | 0.000 | 0.220 | 0.000 | 0.135 | 0.000 | 0.347 | 0.085 | 0.125 |
| DPE | 0.000 | 0.000 | 0.000 | 0.000 | 0.000 | 0.000 | 0.060 | 0.000 | 0.000 |
| AE-TAEA | 0.000 | 0.000 | 0.000 | 0.000 | 0.000 | 0.000 | 0.236 | 0.000 | 0.000 |
| 1-TEPA | 0.000 | 0.000 | 0.463 | 0.000 | 0.000 | 0.000 | 0.848 | 0.318 | 0.401 |
| AE-DAEP | 0.000 | 0.000 | 0.000 | 0.000 | 0.000 | 0.000 | 0.181 | 0.000 | 0.000 |
| AE-PEEDA | 0.000 | 0.000 | 0.000 | 0.000 | 0.000 | 0.000 | 0.000 | 0.000 | 0.000 |
| iAE-PEEDA | 0.000 | 0.000 | 0.000 | 0.000 | 0.000 | 0.000 | 0.000 | 0.000 | 0.000 |
| AE-DPE | 0.000 | 0.000 | 0.000 | 0.000 | 0.000 | 0.000 | 0.279 | 0.000 | 0.000 |
| BPEA | 0.000 | 0.000 | 0.000 | 0.000 | 0.000 | 0.000 | 0.000 | 0.000 | 0.000 |
| Others | 0.976 | 0.215 | 1.483 | 1.078 | 1.416 | 1.247 | 1.734 | 1.491 | 2.212 |
| MEA conversion, % | 20.13 | 12.23 | 32.26 | 12.02 | 24.15 | 14.16 | 38.70 | 28.47 | 29.14 |
| DETA conversion, % | 2.69 | 4.31 | 6.99 | 3.83 | 4.40 | 3.59 | 11.07 | 5.24 | 7.12 |
| Acyclic(N4), wt. % | 94.94 | 95.46 | 92.64 | 95.76 | 93.82 | 95.11 | 90.14 | 95.25 | 95.85 |
| Acyclic(N5), wt. % | — | — | 100.00 | — | — | — | 70.20 | 100.00 | 100.00 |
| Σ(N5)/Σ(N4), weight ratio | 0.00 | 0.00 | 0.00 | 0.00 | 0.00 | 0.00 | 0.16 | 0.05 | 0.05 |
| Acyclic(N4)/cyclic(< = N4), weight ratio | 4.13 | 3.63 | 2.31 | 3.90 | 3.26 | 3.90 | 2.24 | 3.45 | 3.82 |

TABLE XXXVI

| | Example No. | | | | | | | | |
|---|---|---|---|---|---|---|---|---|---|
| | 386 | 387 | 388 | 389 | 390 | 391 | 392 | 393 | 394 |
| Catalyst Type | JJ | JJ | JJ | JJ | JJ | JJ | JJ | JJ | JJ |
| Catalyst weight, gm | 67.5 | 67.5 | 67.5 | 67.5 | 67.5 | 67.5 | 67.5 | 67.5 | 67.5 |
| Pressure, psig | 598 | 597 | 597 | 598 | 598 | 598 | 598 | 600 | 600 |
| Temperature, °C. | 270 | 270 | 280 | 260 | 270 | 260 | 280 | 280 | 270 |
| Time on organics, hrs. | 7 | 26 | 30.5 | 50 | 55 | 74 | 79 | 98.8 | 123 |
| Duration of run, hrs. | 2 | 2 | 1 | 2 | 2 | 2 | 2 | 2 | 2 |
| MEA SV, gmol/hr/kgcat | 3.62 | 3.73 | 3.53 | 3.46 | 3.70 | 3.56 | 3.47 | 3.46 | 3.40 |
| DETA/MEA mole ratio | 1.00 | 1.00 | 1.00 | 1.00 | 1.00 | 1.00 | 1.00 | 1.00 | 1.00 |
| NH₃/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 0.294 | 0.424 | 0.706 | 0.273 | 0.506 | 0.342 | 0.979 | 1.001 | 0.624 |
| MEA | 25.314 | 22.475 | 18.589 | 26.092 | 22.747 | 25.743 | 18.317 | 16.142 | 21.635 |
| PIP | 0.421 | 0.496 | 0.707 | 0.266 | 0.485 | 0.297 | 0.712 | 0.692 | 0.469 |
| DETA | 54.036 | 51.203 | 48.723 | 54.115 | 52.329 | 54.167 | 48.580 | 42.653 | 47.745 |
| AEEA | 1.899 | 2.033 | 1.670 | 2.115 | 2.193 | 2.258 | 1.799 | 1.403 | 1.963 |
| AEP | 0.488 | 0.616 | 0.869 | 0.374 | 0.614 | 0.438 | 0.855 | 0.848 | 0.588 |
| HEP | 0.000 | 0.000 | 0.000 | 0.000 | 0.000 | 0.000 | 0.000 | 0.000 | 0.000 |
| TAEA | 1.340 | 1.728 | 1.888 | 1.215 | 1.590 | 1.290 | 1.768 | 1.764 | 1.551 |
| 1-TETA | 6.203 | 8.239 | 9.101 | 5.680 | 7.515 | 6.023 | 8.740 | 9.202 | 7.737 |

TABLE XXXVI-continued

| | | | | | | | | | |
|---|---|---|---|---|---|---|---|---|---|
| DAEP | 0.091 | 0.205 | 0.282 | 0.096 | 0.157 | 0.110 | 0.267 | 0.415 | 0.216 |
| PEEDA | 0.093 | 0.162 | 0.229 | 0.076 | 0.133 | 0.090 | 0.209 | 0.313 | 0.172 |
| DPE | 0.048 | 0.111 | 0.178 | 0.076 | 0.126 | 0.084 | 0.220 | 0.387 | 0.232 |
| AE-TAEA | 1.230 | 1.884 | 2.347 | 1.338 | 1.704 | 1.006 | 1.902 | 2.806 | 1.832 |
| 1-TEPA | 2.363 | 3.385 | 4.197 | 1.841 | 2.798 | 1.882 | 3.504 | 5.099 | 3.159 |
| AE-DAEP | 0.139 | 0.145 | 0.257 | 0.143 | 0.273 | 0.114 | 0.392 | 0.812 | 0.539 |
| AE-PEEDA | 0.066 | 0.034 | 0.101 | 0.042 | 0.061 | 0.024 | 0.100 | 0.168 | 0.078 |
| iAE-PEEDA | 0.000 | 0.000 | 0.000 | 0.000 | 0.000 | 0.000 | 0.000 | 0.000 | 0.000 |
| AE-DPE | 0.000 | 0.043 | 0.117 | 0.077 | 0.157 | 0.090 | 0.062 | 0.343 | 0.035 |
| BPEA | 0.110 | 0.211 | 0.290 | 0.056 | 0.110 | 0.069 | 0.063 | 0.209 | 0.048 |
| Others | 2.415 | 3.286 | 4.610 | 2.509 | 3.660 | 2.432 | 4.633 | 8.202 | 4.835 |
| MEA conversion, % | 31.77 | 40.08 | 50.03 | 29.37 | 39.57 | 30.42 | 49.72 | 55.92 | 40.42 |
| DETA conversion, % | 13.44 | 18.87 | 22.15 | 12.94 | 17.39 | 12.99 | 20.75 | 30.77 | 21.85 |
| Acyclic(N4), wt. % | 97.01 | 95.43 | 94.10 | 96.54 | 95.63 | 96.27 | 93.80 | 90.77 | 93.73 |
| Acyclic(N5), wt. % | 91.93 | 92.41 | 89.53 | 90.91 | 88.22 | 90.67 | 89.75 | 83.77 | 87.68 |
| Σ(N5)/Σ(N4), weight ratio | 0.50 | 0.55 | 0.63 | 0.49 | 0.54 | 0.42 | 0.54 | 0.78 | 0.57 |
| Acyclic(N4)/cyclic(< = N4), weight ratio | 6.61 | 6.27 | 4.85 | 7.78 | 6.01 | 7.18 | 4.65 | 4.13 | 5.53 |

| | Example No. | | | | | | | | | |
|---|---|---|---|---|---|---|---|---|---|---|
| | 395 | 396 | 397 | 398 | 399 | 400 | 401 | 402 | 403 | 404 |
| Catalyst Type | JJ | JJ | JJ | JJ | JJ | JJ | JJ | JJ | JJ | JJ |
| Catalyst weight, gm | 67.5 | 67.5 | 67.5 | 67.5 | 67.5 | 67.5 | 67.5 | 67.5 | 67.5 | 67.5 |
| Pressure, psig | 585 | 598 | 598 | 598 | 598 | 598 | 598 | 598 | 598 | 598 |
| Temperature, °C. | 271 | 282 | 260 | 270 | 260 | 281 | 272 | 280 | 272 | 271 |
| Time on organics, hrs. | 158 | 163 | 182 | 187 | 206 | 211 | 272 | 235 | 254 | 257.5 |
| Duration of run, hrs. | 2 | 2 | 2 | 2 | 2 | 2 | 2 | 2 | 2 | 2 |
| MEA SV, gmol/hr/kgcat | 2.97 | 3.69 | 3.58 | 3.41 | 3.41 | 3.54 | 3.99 | 3.53 | 3.50 | 3.70 |
| DETA/MEA mole ratio | 1.00 | 1.00 | 1.00 | 1.00 | 1.00 | 1.00 | 1.00 | 1.00 | 1.00 | 1.00 |
| NH3/MEA mole ratio | 5.97 | 5.97 | 5.97 | 5.97 | 5.97 | 5.97 | 5.97 | 5.97 | 5.97 | 5.97 |
| Crude product composition, wt. % | | | | | | | | | | |
| EDA | 0.764 | 1.129 | 0.479 | 0.786 | 0.509 | 1.756 | 1.803 | 1.993 | 1.749 | 1.597 |
| MEA | 20.571 | 16.885 | 25.262 | 21.504 | 25.342 | 18.397 | 20.631 | 15.100 | 20.996 | 22.350 |
| PIP | 0.531 | 0.826 | 0.351 | 0.538 | 0.352 | 0.865 | 0.634 | 0.781 | 0.638 | 0.567 |
| DETA | 47.941 | 46.768 | 52.656 | 48.687 | 51.138 | 47.357 | 46.647 | 42.162 | 46.440 | 48.370 |
| AEEA | 1.707 | 1.530 | 2.132 | 1.979 | 2.129 | 1.620 | 1.738 | 1.446 | 1.730 | 1.824 |
| AEP | 0.697 | 1.034 | 0.470 | 0.636 | 0.432 | 0.927 | 0.707 | 0.935 | 0.676 | 0.626 |
| HEP | 0.000 | 0.000 | 0.000 | 0.000 | 0.000 | 0.000 | 0.000 | 0.000 | 0.000 | 0.000 |
| TAEA | 1.641 | 1.964 | 1.408 | 1.541 | 1.337 | 1.743 | 1.648 | 1.942 | 1.596 | 1.530 |
| 1-TETA | 8.006 | 9.717 | 6.641 | 7.305 | 6.278 | 8.432 | 8.037 | 9.595 | 7.922 | 7.422 |
| DAEP | 0.239 | 0.408 | 0.135 | 0.174 | 0.125 | 0.291 | 0.359 | 0.442 | 0.295 | 0.232 |
| PEEDA | 0.186 | 0.297 | 0.101 | 0.138 | 0.094 | 0.224 | 0.234 | 0.314 | 0.215 | 0.169 |
| DPE | 0.211 | 0.069 | 0.110 | 0.183 | 0.114 | 0.089 | 0.099 | 0.103 | 0.182 | 0.107 |
| AE-TAEA | 1.858 | 2.661 | 1.266 | 1.659 | 1.462 | 2.013 | 2.165 | 2.975 | 2.063 | 1.905 |
| 1-TEPA | 3.247 | 5.154 | 2.314 | 2.935 | 2.396 | 3.688 | 3.984 | 5.395 | 3.860 | 3.394 |
| AE-DAEP | 0.401 | 0.342 | 0.130 | 0.223 | 0.173 | 0.261 | 0.335 | 0.507 | 0.256 | 0.234 |
| AE-PEEDA | 0.057 | 0.062 | 0.025 | 0.068 | 0.063 | 0.045 | 0.076 | 0.117 | 0.056 | 0.042 |
| iAE-PEEDA | 0.000 | 0.000 | 0.000 | 0.000 | 0.000 | 0.000 | 0.000 | 0.000 | 0.000 | 0.000 |
| AE-DPE | 0.053 | 0.067 | 0.086 | 0.211 | 0.083 | 0.034 | 0.229 | 0.080 | 0.055 | 0.040 |
| BPEA | 0.051 | 0.390 | 0.040 | 0.087 | 0.037 | 0.225 | 0.294 | 0.465 | 0.272 | 0.231 |
| Others | 4.459 | 5.997 | 2.874 | 5.176 | 3.565 | 5.035 | 6.180 | 8.307 | 5.107 | 4.381 |
| MEA conversion, % | 42.93 | 55.07 | 31.89 | 40.98 | 31.07 | 49.41 | 44.79 | 58.84 | 42.66 | 39.29 |
| DETA conversion, % | 20.95 | 26.04 | 15.63 | 20.58 | 17.33 | 22.60 | 25.81 | 31.71 | 24.63 | 31.91 |
| Acyclic(N4), wt. % | 93.81 | 93.79 | 95.88 | 94.70 | 95.80 | 94.40 | 93.33 | 93.06 | 93.21 | 94.64 |
| Acyclic(N5), wt. % | 90.08 | 90.08 | 92.72 | 88.64 | 91.56 | 90.98 | 86.82 | 87.74 | 90.25 | 90.67 |
| Σ(N5)/Σ(N4), weight ratio | 0.55 | 0.70 | 0.46 | 0.55 | 0.53 | 0.58 | 0.68 | 0.77 | 0.64 | 0.62 |
| Acyclic(N4)/cyclic(< = N4), weight ratio | 5.17 | 4.43 | 6.90 | 5.30 | 6.82 | 4.25 | 4.76 | 4.48 | 4.74 | 5.26 |

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

We claim:

1. A process of making polyalkylene polyamines which comprises condensing an amino compound, said amino compound comprising ammonia, one or more compounds containing nitrogen to which is bonded an active hydrogen or mixtures thereof, in the presence of a metallic phosphate condensation catalyst having a cyclic structure, said condensation catalyst being selected from the group consisting of one or more metallic metaphosphates, metallic ultraphosphates, metallic metaphosphimates, metallic imidophosphates and mixtures thereof.

2. The process of claim 1 wherein the metal portion of the metallic phosphate condensation catalyst is selected from the group consisting of Group IA, Group IIA, Group IIIB, Group IVB, Group VB, Group VIB, Group VIIB, Group VIII, Group IB, Group IIB, Group IIIA, Group IVA, Group VA, and Group VIA metals and mixtures thereof.

3. The process of claim 1 wherein the metallic phosphate condensation catalyst comprises a metallic metaphosphate.

4. The process of claim 3 wherein the metallic metaphosphate comprises sodium trimetaphosphate.

5. The process of claim 3 wherein the metallic metaphosphate comprises a mixture of sodium trimetaphosphate and sodium tripolyphosphate.

6. The process of claim 1 wherein the metallic phosphate condensation catalyst is associated with a Group IVB metal oxide or a Group IVA metal oxide.

7. The process of claim 6 wherein the Group IVB metal oxide comprises a high surface area titanium oxide or zirconium oxide.

8. The process of claim 6 wherein the Group IVA metal oxide comprises a high surface area silicon oxide.

9. The process of claim 1 wherein the catalyst has a surface area greater than about 70 m²/gm.

10. The process of claim 7 wherein the titanium oxide comprises titanium dioxide and the zirconium oxide comprises zirconium dioxide.

11. The process of claim 8 wherein the silicon oxide comprises silica.

12. The process of claim 6 wherein the Group IVB metal oxide comprises a mixture of titanium oxide and zirconium oxide.

13. The process of claim 12 wherein the mixture of titanium oxide and zirconium oxide comprises titanium dioxide and zirconium dioxide.

14. The process of claim 13 wherein the catalyst has a surface area greater than about 140 m²/gm.

15. The process of claim 8 wherein the catalyst has a surface area greater than about 70 m²/gm.

16. The process of claim 1 wherein the catalyst is associated with a support material.

17. The process of claim 7 wherein the catalyst is associated with a support material.

18. The process of claim 8 wherein the catalyst is associated with a support material.

19. The process of claim 16 wherein the support comprises an alumina material or an alumina-silica material.

20. The process of claim 16 wherein the support comprises a silica material or a silica-alumina material.

21. The process of claim 17 wherein the support comprises an alumina material or an alumina-silica material.

22. The process of claim 17 wherein the support comprises a silica material or a silica-alumina material.

23. The process of claim 18 wherein the support comprises an alumina material or an alumina-silica material.

24. The process of claim 18 wherein the support comprises a silica material or a silica-alumina material.

25. The process of claim 16 wherein the support comprises from about 2 to about 60 percent by weight of the catalyst.

26. The process of claim 17 wherein the support comprises from about 2 to about 60 percent by weight of the catalyst.

27. The process of claim 18 wherein the support comprises from about 2 to about 60 percent by weight of the catalyst.

28. The process of claim 1 wherein the catalyst contains a performance moderator.

29. The process of claim 7 wherein the catalyst contains a performance moderator.

30. The process of claim 8 wherein the catalyst contains a performance moderator.

31. The process of claim 28 wherein the performance moderator comprises one or more metal oxides.

32. The process of claim 29 wherein the performance moderator comprises one or more metal oxides.

33. The process of claim 30 wherein the performance moderator comprises one or more metal oxides.

34. The process of claim 31 wherein the performance moderator is selected from the group consisting of one or more Group IA metal oxides, Group IIA metal oxides, Group IIIB metal oxides, Group VB metal oxides, Group VIB metal oxides, Group VIIB metal oxides, Group VIII metal oxides, Group IB metal oxides, Group IIB metal oxides, Group IIIA metal oxides, Group IVA metal oxides, Group VA metal oxides, Group VIA metal oxides, Group IVB metal oxides and mixtures thereof.

35. The process of claim 34 wherein the performance moderator is selected from the group consisting of one or more oxides of scandium, yttrium, lanthanum, cerium, gadolinium, lutetium, ytterbium, niobium, tantalum, chromium, molybdenum, tungsten, titanium, zirconium, iron, cobalt, nickel, zinc, cadmium, boron, aluminum, gallium, indium, silicon, germanium, tin, lead, arsenic, antimony and bismuth.

36. The process of claim 32 wherein the performance moderator is selected from the group consisting of one or more Group IA metal oxides, Group IIA metal oxides, Group IIIB metal oxides, Group VB metal oxides, Group VIB metal oxides, Group VIIB metal oxides, Group VIII metal oxides, Group IB metal oxides, Group IIB metal oxides, Group IIIA metal oxides, Group IVA metal oxides, Group VA metal oxides, Group VIA metal oxides, Group IVB metal oxides and mixtures thereof.

37. The process of claim 36 wherein the performance moderator is selected from the group consisting of one or more oxides of scandium, yttrium, lanthanum, cerium, gadolinium, lutetium, ytterbium, niobium, tantalum, chromium, molybdenum, tungsten, titanium, zirconium, iron, cobalt, nickel, zinc, cadmium, boron, aluminum, gallium, indium, silicon, germanium, tin, lead, arsenic, antimony and bismuth.

38. The process of claim 33 wherein the performance moderator is selected from the group consisting of one or more Group IA metal oxides, Group IIA metal oxides, Group IIIB metal oxides, Group VB metal oxides, Group VIB metal oxides, Group VIIB metal oxides, Group VIII metal oxides, Group IB metal oxides, Group IIB metal oxides, Group IIIA metal oxides, Group IVA metal oxides, Group VA metal oxides, Group VIA metal oxides, Group IVB metal oxides and mixtures thereof.

39. The process of claim 38 wherein the performance moderator is selected from the group consisting of one or more oxides of scandium, yttrium, lanthanum, cerium, gadolinium, lutetium, ytterbium, niobium, tantalum, chromium, molybdenum, tungsten, titanium, zirconium, iron, cobalt, nickel, zinc, cadmium, boron, aluminum, gallium, indium, silicon, germanium, tin, lead, arsenic, antimony and bismuth.

40. The process of claim 28 wherein the performance moderator is selected from the group consisting of a metallic orthophosphate, a metallic pyrophosphate, a metallic polyphosphate, a metallic phosphoramidate, a metallic amidophosphate, and mixtures thereof.

41. The process of claim 29 wherein the performance moderator is selected from the group consisting of a metallic orthophosphate, a metallic pyrophosphate, a metallic polyphosphate, a metallic phosphoramidate, a metallic amidophosphate, and mixtures thereof.

42. The process of claim 30 wherein the performance moderator is selected from the group consisting of a metallic orthophosphate, a metallic pyrophosphate, a metallic polyphosphate, a metallic phosphoramidate, a metallic amidophosphate, and mixtures thereof.

43. The process of claim 28 wherein the performance moderator comprises a mineral acid or a compound derived from a mineral acid.

44. The process of claim 29 wherein the performance moderator comprises a mineral acid or a compound derived from a mineral acid.

45. The process of claim 30 wherein the performance moderator comprises a mineral acid or a compound derived from a mineral acid.

46. The process of claim 43 wherein the performance moderator comprises phosphoric acid or a salt of phosphoric acid.

47. The process of claim 44 wherein the performance moderator comprises phosphoric acid or a salt of phosphoric acid.

48. The process of claim 45 wherein the performance moderator comprises phosphoric acid or a salt of phosphoric acid.

49. The process of claim 43 wherein the performance moderator comprises hydrogen fluoride, hydrofluoric acid or a fluoride salt.

50. The process of claim 44 wherein the performance moderator comprises hydrogen fluoride, hydrofluoric acid or a fluoride salt.

51. The process of claim 45 wherein the performance moderator comprises hydrogen fluoride, hydrofluoric acid or a fluoride salt.

52. The process of claim 43 wherein the performance moderator comprises sulfuric acid or a salt of sulfuric acid.

53. The process of claim 44 wherein the performance moderator comprises sulfuric acid or a salt or sulfuric acid.

54. The process of claim 45 wherein the performance moderator comprises sulfuric acid or a salt or sulfuric acid.

55. The process of claim 6 wherein the Group IVB metal oxide comprises a mixed oxide of a Group IVB metal oxide and one or more other metal oxides.

56. The process of claim 55 wherein the metal oxide is selected from the group consisting of one or more Group IA metal oxides, Group IIA metal oxides, Group IIIB metal oxides, Group VB metal oxides, Group VIB metal oxides, Group VIIB metal oxides, Group VIII metal oxides, Group IB metal oxides, Group IIB metal oxides, Group IIIA metal oxides, Group IVA metal oxides, Group VA metal oxides, Group VIA metal oxides, other Group IVB metal oxides and mixtures thereof.

57. The process of claim 55 wherein the metal oxide is selected from the group consisting of one or more oxides of scandium, yttrium, lanthanum, cerium, gadolinium, lutetium, ytterbium, niobium, tantalum, chromium, molybdenum, tungsten, titanium, zirconium, iron, cobalt, nickel, zinc, cadmium, boron, aluminum, gallium, indium, silicon, germanium, tin, lead, arsenic, antimony and bismuth.

58. The process of claim 1 wherein the Group IVB metal oxide comprises from about 25 weight percent to about 90 weight percent of the weight of the catalyst.

59. The process of claim 6 wherein the Group IVB metal oxide comprises from about 50 weight percent to about 90 weight percent of the weight of the catalyst, 60. The process of claim 6 wherein the Group IVB metal oxide comprises from about 75 weight percent to about 90 weight percent of the weight of the catalyst.

61. The process of claim 1 wherein the amino compound comprises an alkyleneamine.

62. The process of claim 1 further comprising the addition of an alcohol.

63. The process of claim 62 wherein the alcohol comprises an alkanolamine or an alkylene glycol.

64. The process of claim 63 wherein the alkanolamine comprises aminoethylethanolamine.

65. The process of claim 1 wherein the amino compound comprises a mixture of monoethanolamine and ethylenediamine.

66. The process of claim 1 wherein the amino compound comprises a mixture of monoethanolamine and diethylenetriamine.

67. The process to claim 1 wherein the amino compound comprises a mixture of monoethanolamine, ethylenediamine and ammonia.

68. The process of claim 1 wherein the amino compound comprises a mixture of monoethanolamine, diethylenetriamine and ammonia.

69. The process of claim 1 wherein the amino compound comprises a mixture of aminoethylethanolamine and ethylenediamine.

70. The process of claim 1 wherein the amino compound comprises a mixture of aminoethylethanolamine and diethylenetriamine.

71. The process of claim 1 wherein the amino compound comprises a mixture of aminoethylethanolamine, ethylenediamine and ammonia.

72. The process of claim 1 wherein the amino compound comprises a mixture of aminoethyl ethanolamine, diethylenetriamine and ammonia.

73. The process of claim 1 wherein the polyalkylene polyamines product has a TETA+TAEA to PIP+AEP+PEEDA+DAEP+DPE weight ratio of greater than about 0.5, a TETA to TAEA weight ratio of greater than about 2.0 and a TEPA to AETAEA weight ratio of greater than about 2.0.

74. The polyalkylene polyamines product prepared by the process of claim 1.

75. The process of claim 1 in which the amines product comprises, based on 100 percent of the weight of the product and exclusive of any water and/or ammonia present,
   a) greater than about 3.0 weight percent of the combination of TETA and TEPA,
   b) greater than about 0.1 weight percent of TEPA,
   c) greater than about 3.0 weight percent of TETA,
   d) less than about 90.0 weight percent of DETA and/or EDA,
   e) less than about 90.0 weight percent of MEA and/or AEEA,
   f) less than about 12.5 weight percent of the combination of PIP and AEP,
   g) less than about 15.0 weight percent of other polyalkylene polyamines,
   h) a TETA+TAEA to PIP+AEP+PEEDA+DAEP+DPE weight ratio of greater than about 0.5,
   i) a TEPA+AETAEA to PIP+AEP+PEEDA+DAEP+DPE+AEPEEDA+iAEPEEDA+AEDAEP+AEDPE+BPEA weight ratio of greater than about 0.5,
   j) a TETA to TAEA weight ratio of greater than about 2.0, and
   k) a TEPA to AETAEA weight ratio of greater than about 2.0.

76. The process of claim 1 wherein the amino compound comprises ethylenediamine in association with ethylene glycol or diethylenetriamine in association with ethylene glycol.

77. The process of claim 1 wherein the amino compound comprises a mixture of diethanolamine and ethylenediamine or a mixture of diethanolamine and diethylenetriamine.

78. The process of claim 1 wherein the amino compound comprises a mixture of dihydroxyethylethylenediamine and ethylenediamine or a mixture of dihydroxyethylethylendiamine and diethylenetriamine.

79. The process of claim 1 wherein the amino compound comprises a mixture of dihydroxyethyldiethylenetriamine and ethylenediamine or a mixture of dihydroxyethyldiethylenetriamine and diethylenetriamine.

80. The process of claim 1 wherein the amino compound comprises a mixture of dihydroxyethyltriethylenetramine and ethylenediamine or a mixture of dihydroxyethyltriethylenetramine and diethylenetriamine.

81. The process of claim 3 wherein the metallic metaphosphate comprises sodium tetrametaphosphate.

82. The process of claim 1 which is effected in the liquid phase, vapor phase, supercritical liquid phase or mixtures thereof.

83. A process of making alkylamines which comprises contacting an alcohol and at least one of a primary amine, a secondary amine or a tertiary amine in the presence of a metallic phosphate condensation catalyst having a cyclic structure.

* * * * *

UNITED STATES PATENT AND TRADEMARK OFFICE
CERTIFICATE OF CORRECTION

PATENT NO. : 5,202,492                                          Page 1 of 2

DATED : April 13, 1993

INVENTOR(S) : Arthur R. Doumaux, Jr. and David J. Schreck

It is certified that error appears in the above-identified patent and that said Letters Patent is hereby corrected as shown below:

Column 75,

Claim 14, line 1, change "13" to --7--.

Column 79,

Claim 79, line 2, change "dihydroxyethyldiethylenetriamine" to --hydroxyethyldiethylenetriamine--.

Claim 79, line 4, change "dihydroxyethyldiethylenetriamine" to --hydroxyethyldiethylenetriamine--.

Claim 80, line 2, change "dihydroxyethyltriethylenetriamine" to --hydroxyethyltriethylenetriamine--.

UNITED STATES PATENT AND TRADEMARK OFFICE
CERTIFICATE OF CORRECTION

PATENT NO. : 5,202,492

DATED : April 13, 1993

INVENTOR(S) : Arthur R. Doumaux, Jr. and David J. Schreck

It is certified that error appears in the above-indentified patent and that said Letters Patent is hereby corrected as shown below:

Column 80, line 4, claim 80, change "dihydroxyethyltriethylenetriamine" to --hydroxyethyltriethylenetriamine--.

Signed and Sealed this

Twenty-second Day of March, 1994

Attest:

BRUCE LEHMAN

Attesting Officer

Commissioner of Patents and Trademarks